(12) United States Patent
Tran et al.

(10) Patent No.: US 10,252,145 B2
(45) Date of Patent: Apr. 9, 2019

(54) SMART DEVICE

(71) Applicant: Bao Tran, Saratoga, CA (US)

(72) Inventors: Bao Tran, Saratoga, CA (US); Ha Tran, Saratoga, CA (US)

(*) Notice: Subject to any disclaimer, the term of this patent is extended or adjusted under 35 U.S.C. 154(b) by 0 days.

(21) Appl. No.: 15/624,927

(22) Filed: Jun. 16, 2017

(65) Prior Publication Data
US 2018/0001184 A1    Jan. 4, 2018

Related U.S. Application Data

(63) Continuation-in-part of application No. 15/407,253, filed on Jan. 17, 2017, now Pat. No. 9,713,756, which
(Continued)

(51) Int. Cl.
*G06F 19/00* (2018.01)
*A63B 71/14* (2006.01)
(Continued)

(52) U.S. Cl.
CPC .......... *A63B 71/145* (2013.01); *A63B 43/004* (2013.01); *A63B 60/46* (2015.10); *A63B 69/36* (2013.01); *A63B 69/38* (2013.01); *A63B 71/06* (2013.01); *A63F 13/211* (2014.09); *B33Y 10/00* (2014.12); *G01L 5/0052* (2013.01); *G01N 29/14* (2013.01); *G01N 29/4436* (2013.01); *G06F 1/163* (2013.01); *G06F 3/00* (2013.01); *G06F 3/017* (2013.01); *G06F 19/00* (2013.01); *G06K 9/00342* (2013.01); *G06K 9/00355* (2013.01); *G09B 19/003* (2013.01); *G09B 19/0038* (2013.01); *G16H 50/20* (2018.01); *H04N 5/2257* (2013.01); *H04Q 9/00* (2013.01); *H04W 4/027* (2013.01); *H04W 4/38* (2018.02); *H04W 84/18* (2013.01); *A42B 3/046* (2013.01); *A42B 3/0433* (2013.01); *A61B 5/0205* (2013.01); *A61B 5/11* (2013.01); *A61B 5/681* (2013.01); *A61B 5/6804* (2013.01); *A61B 5/6895* (2013.01); *A63B 21/072* (2013.01); *A63B 21/0724* (2013.01); *A63B 21/0726* (2013.01); *A63B 69/0002* (2013.01);
(Continued)

(58) Field of Classification Search
USPC ...................................... 463/16–42
See application file for complete search history.

(56) References Cited

U.S. PATENT DOCUMENTS 6,720,984 B1 * 4/2004 Jorgensen ............... G06F 3/015
                                                          600/300
8,069,055 B2   11/2011 Keen
(Continued)

FOREIGN PATENT DOCUMENTS

WO    WO2015063376    5/2015

OTHER PUBLICATIONS

Tatonetti et al, Data-Driven Prediction of Drug Effects and Interactions, Sci Transl Med. Mar. 14, 2012; 4(125): 125ra31.
(Continued)

*Primary Examiner* — Masud Ahmed
(74) *Attorney, Agent, or Firm* — Tran & Associates

(57) ABSTRACT

An Internet of Thing (IoT) device includes a camera coupled to a processor; and a wireless transceiver coupled to the processor. Blockchain smart contracts can be used with the device to facilitate secure operation.

3 Claims, 23 Drawing Sheets

Related U.S. Application Data is a continuation of application No. 15/144,773, filed on May 2, 2016, now Pat. No. 9,610,476.

(51) Int. Cl.

| | |
|---|---|
| *B33Y 10/00* | (2015.01) |
| *G09B 19/00* | (2006.01) |
| *G06K 9/00* | (2006.01) |
| *G06F 3/00* | (2006.01) |
| *A63B 69/36* | (2006.01) |
| *H04W 84/18* | (2009.01) |
| *G01L 5/00* | (2006.01) |
| *G06F 1/16* | (2006.01) |
| *A63B 69/38* | (2006.01) |
| *A63B 71/06* | (2006.01) |
| *A63B 43/00* | (2006.01) |
| *G06F 3/01* | (2006.01) |
| *H04Q 9/00* | (2006.01) |
| *A63F 13/211* | (2014.01) |
| *A63B 60/46* | (2015.01) |
| *G16H 50/20* | (2018.01) |
| *H04N 5/225* | (2006.01) |
| *H04W 4/02* | (2018.01) |
| *H04W 4/38* | (2018.01) |
| *G01N 29/14* | (2006.01) |
| *G01N 29/44* | (2006.01) |
| *A63B 21/072* | (2006.01) |
| *A63B 71/12* | (2006.01) |
| *A61B 5/00* | (2006.01) |
| *A61B 5/11* | (2006.01) |
| *A63B 71/10* | (2006.01) |
| *A63B 71/08* | (2006.01) |
| *A63B 69/16* | (2006.01) |
| *A63B 69/06* | (2006.01) |
| *A63B 69/02* | (2006.01) |
| *A63B 69/00* | (2006.01) |
| *A42B 3/04* | (2006.01) |
| *H04B 1/04* | (2006.01) |
| *H04N 7/18* | (2006.01) |
| *H04L 29/08* | (2006.01) |
| *A61B 5/0205* | (2006.01) |

(52) U.S. Cl.
CPC ....... *A63B 69/0026* (2013.01); *A63B 69/0028* (2013.01); *A63B 69/0048* (2013.01); *A63B 69/0071* (2013.01); *A63B 69/02* (2013.01); *A63B 69/06* (2013.01); *A63B 69/16* (2013.01); *A63B 69/3632* (2013.01); *A63B 71/085* (2013.01); *A63B 71/10* (2013.01); *A63B 71/1216* (2013.01); *A63B 71/1291* (2013.01); *A63B 71/141* (2013.01); *A63B 2071/125* (2013.01); *A63B 2071/1233* (2013.01); *A63B 2071/1283* (2013.01); *A63B 2207/02* (2013.01); *A63B 2220/12* (2013.01); *A63B 2220/13* (2013.01); *A63B 2220/16* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/53* (2013.01); *A63B 2220/56* (2013.01); *A63B 2220/72* (2013.01); *A63B 2220/74* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/30* (2013.01); *A63B 2225/50* (2013.01); *A63B 2225/54* (2013.01); *A63B 2230/06* (2013.01); *A63B 2230/60* (2013.01); *A63B 2230/70* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *A63B 2243/0095* (2013.01); *A63B 2244/102* (2013.01); *A63B 2244/18* (2013.01); *A63B 2244/19* (2013.01); *A63B 2244/20* (2013.01); *A63B 2244/203* (2013.01); *G01N 2291/0258* (2013.01); *G01N 2291/044* (2013.01); *H04B 1/04* (2013.01); *H04L 67/10* (2013.01); *H04N 7/18* (2013.01); *H04Q 2209/40* (2013.01)

(56) References Cited

U.S. PATENT DOCUMENTS

| | | | |
|---|---|---|---|
| 8,155,887 B2 | 4/2012 | Rothschild | |
| 8,606,761 B2 | 12/2013 | Kenedy | |
| 8,620,594 B2 | 12/2013 | Silver | |
| 8,747,336 B2* | 6/2014 | Tran | G06F 19/3418 600/300 |
| 9,011,834 B1 | 4/2015 | Mckenzie | |
| 2002/0065121 A1* | 5/2002 | Fukunaga | A63F 13/08 463/8 |
| 2006/0085230 A1 | 5/2006 | Brill | |
| 2006/0160616 A1* | 7/2006 | Kato | A63F 13/10 463/30 |
| 2006/0166737 A1* | 7/2006 | Bentley | A61B 5/1122 463/30 |
| 2010/0113892 A1 | 5/2010 | Kaput | |
| 2010/0144414 A1* | 6/2010 | Edis | A63B 24/0006 463/8 |
| 2010/0160172 A1 | 6/2010 | Erlich | |
| 2010/0274586 A1 | 10/2010 | Choi | |
| 2012/0144554 A1* | 6/2012 | Thellmann | A63B 21/065 2/161.1 |
| 2013/0066448 A1* | 3/2013 | Alonso | H04Q 9/00 700/91 |
| 2013/0144916 A1 | 6/2013 | Lum | |
| 2013/0179375 A1 | 7/2013 | Tatonetti | |
| 2014/0072278 A1* | 3/2014 | Kramer | H04N 5/23296 386/240 |
| 2014/0073481 A1* | 3/2014 | Aibara | A63B 24/0084 482/1 |
| 2014/0089399 A1 | 3/2014 | Chun | |
| 2014/0188994 A1 | 7/2014 | Patterson | |
| 2015/0066824 A1 | 3/2015 | Harris | |
| 2015/0252428 A1 | 9/2015 | Comper | |
| 2015/0283450 A1* | 10/2015 | McRoberts | G06Q 10/10 473/470 |
| 2015/0324693 A1 | 11/2015 | Hu | |
| 2015/0356661 A1 | 12/2015 | Rousay | |
| 2015/0360080 A1* | 12/2015 | Hadaschik | G01P 7/00 73/865.4 |
| 2015/0370963 A9 | 12/2015 | Dewey | |
| 2016/0019335 A1 | 1/2016 | Dehaven | |
| 2016/0055422 A1* | 2/2016 | Li | G05B 15/02 706/12 |
| 2016/0077593 A1* | 3/2016 | Zuger | G06F 1/163 345/173 |
| 2016/0331319 A1* | 11/2016 | Kozloski | A61B 5/6803 |
| 2017/0310747 A1* | 10/2017 | Cohn | H04L 67/1068 |

OTHER PUBLICATIONS

Vilar et al, Drug—drug interaction through molecular structure similarity analysis, J Am Med Inform Assoc. Nov.-Dec. 2012; 19(6): 1066-1074.

Quillen, Unpacking Human Evolution to Find the Genetic Determinants of Human Skin Pigmentation, Nov. 17, 2011 | doi:10.1038/skinbio.2011.3.

(56) References Cited

OTHER PUBLICATIONS

Wurmback, DNA Assay Development and Validation for Pigment-Related Features to Assist in the Identification of Missing Persons and Human Remains, 2013.
Barsch, What Controls Variation in Human Skin Color? Public Library of Science. Oct. 13, 2003.
Chen et al, Personal Omics Profiling Reveals Dynamic Molecular and Medical Phenotypes, Cell 148, 1293-1307, Mar. 16, 2012.
Lanman et al, Analytical and Clinical Validation of a Digital Sequencing Panel for Quantitative, Highly Accurate Evaluation of Cell-Free Circulating Tumor DNA, PLOS ONE | DOI:10.1371/journal.pone.0140712 Oct. 16, 2015.
Edwards, Protein Identification from Tandem Mass Spectra by Database Searching, 2014.
Kaput, Nutritional genomics: the next frontier in the postgenomic era, Physiol Genomics 16: 166-177, 2004; 10.1152/physiolgenomics.00107.2003.
Vaseghi, Advanced Digital Signal Processing and Noise Reduction 2008.

\* cited by examiner

FIG. 1B                    FIG. 1C

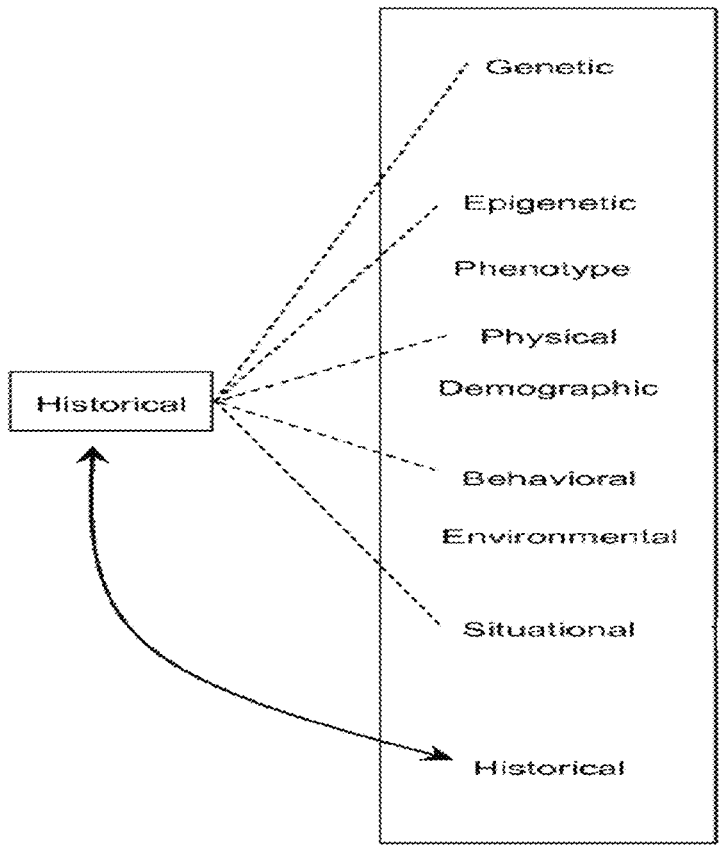

FIG. 13A

| |
|---|
| 110 - image of a substance such as a drug can be acquired |
| 120 - identify content for the substance can be retrieved from the image |
| 130 - substance can be identified according to the identifying content |
| 140 - identified substance can be added to an interaction list |
| 150 - if additional substances remain to be imaged, loop back to 310 |
| 160 - receive genetic scans for subjects |
| 170 – retrieve drug data and drug interaction data for each of the imaged substances and determine relative interactions between substances |
| 180 – apply pharmacogenomic information to the drug-drug interaction data and select the best medication |
| 190 - relative interactions can be rendered within a report such as a paper report or a graphical user interface display |

FIG. 13B

| |
|---|
| 310 - construct a comprehensive gene-drug-drug interactions (GDDIs) training dataset that includes all pharmaceutical, pharmacokinetic (PK), pharmacogenetic (PG),and pharmacodynamic (PD) GDDIs from multiple data sources for each drug in a set of drugs used by a plurality of subjects |
| 320 - construct side effect features for each of the drugs in the set from genetic panels for an individual and side effects associated with the drugs in the set |
| 330 - build, using the GDDIs training dataset, a GDDIs classifier for predicting whether or not a given drug pair derived from the set of drugs results in adverse interactions, and repeat this process for all possible drug pairs derivable from the set of drugs |
| 340 - obtain predicted GDDIs a trained classifier such as a deep learning machine (FIG. 4) |
| 350 - for each side effect, build data structure with side effect features and perform test to determine whether that side effect is differentially shown between positive predicted GDDIs and negative predicted GDDIs |
| 380 – determine relative interactions between the different drug substances by locating references in the interaction data for each of the drug substances to others of the substances |
| 390 render the relative interactions within a report such as a paper report or a graphical user interface display |

FIG. 13D

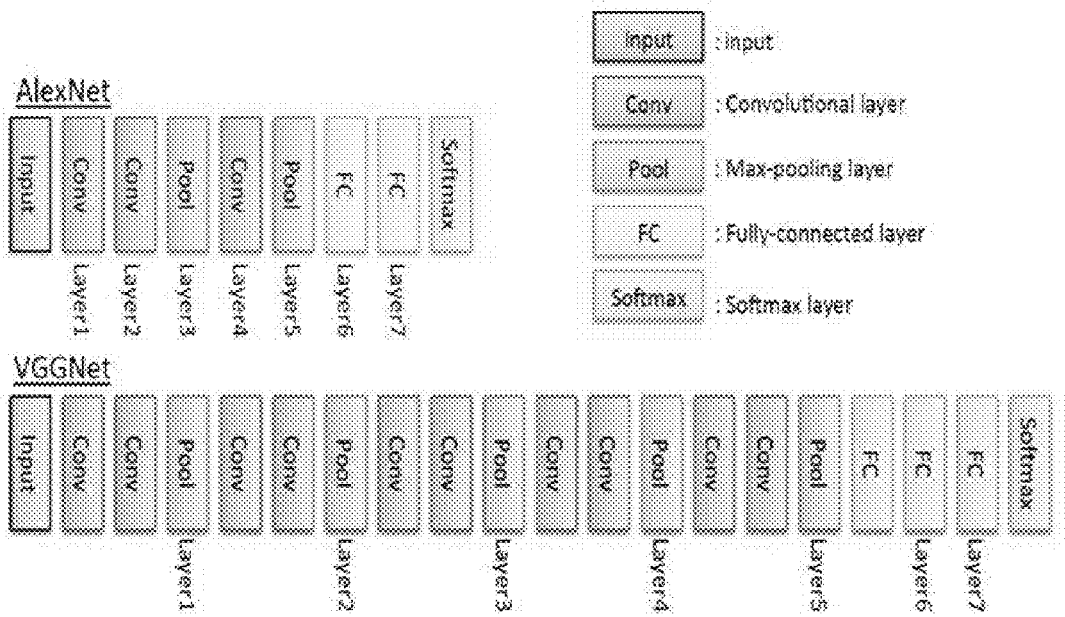

Treating physician/doctor logs into a consultation system and "Create New Case" (500).
Initiates "New Case Wizard" with guided "Initial Assessment" form (501).
    enter Patient Information (502)
    enter Initial Assessment of patient/case (504)
    upload Test Results, Patient Photographs and X-Rays (506)
    accept Payment and Service Terms and Conditions (508)
    review Summary of Case (510)
    submit Forms to a consultant such as an Oncology Service Provider (512).
After the case has been submitted, the Service Provider Consultant can log into the system 1 and consult/process the case (520).
    Using the Treating Doctors Initial Assessment and Photos/X-Rays, the Consultant will click on "Case Consultation" to initiate the "Case Consultation Wizard" (522).
    Consultant can fill out the "Consultant Record Analysis" form (524).
    Consultant can also complete the "Prescription Form" (526)
    Submit completed forms to the original Treating Doctor (528).
Treating Doctor accesses completed forms and either accept the consultation results (i.e. a pre-filled Prescription form) or communicate with the Consultant (530).
Treating Doctor can log into the system (532)
Click on Patient Name to review (534)
Review the Consultation Results (Summary Letter and pre-filled Prescription Form) (536).
If satisfied, the Treating Doctor can click "Approve Treatment" (538)
Mark the case as having being approved (540).
Treating Doctor can print a copy of the Prescription Form and the Summary Letter for submission to nurse or pharmacy (542).
If not satisfied, Treating Doctor can initiate a computer dialog with the Consultant by clicking "Send a Message" (544).
Treating Doctor will be presented with the "Send a Message" screen where a message about the case under consultation can be written (546).
Treating Doctor would click "Submit" to send the message to the appropriate Consultant (548).
Consultant can reply to the Treating Doctor's Message (550)

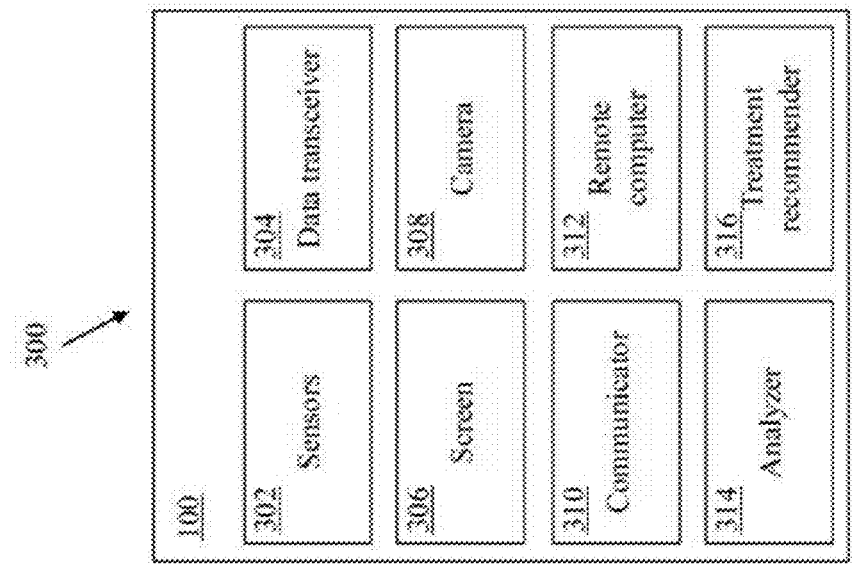
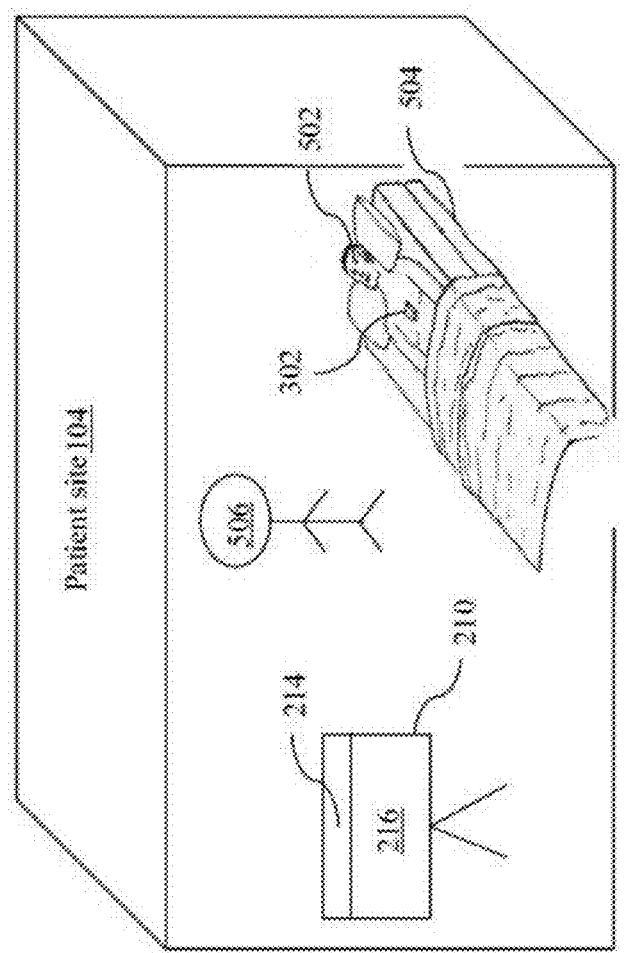
FIG. 15B
FIG. 15C

SMART DEVICE

BACKGROUND

The present invention relates to the Internet of Things (IoT).

SUMMARY

In one aspect, an Internet of Thing (IoT) device includes sensors such as a camera; a processor coupled to the light source and the sensor; and a wireless transceiver coupled to the processor.

In another aspect, systems and methods disclosed for recommending lifestyle modification for a subject by using a DNA sequencer to generate genetic information; aggregating genetic information, environmental information, treatment data, and treatment response from a patient population; deep learning with a computer to generate at least one computer implemented classifier that predicts disease risks based on the aggregated genetic information, treatment data, and treatment response from a patient population; and recommending lifestyle modification to mitigate the disease risks.

In another aspect, a system includes a substance to be consumed by a subject and one or more indicia labeling the substance with: genomic biomarkers; drug exposure and clinical response variability; risk for adverse events; genotype-specific dosing; polymorphic drug target and disposition genes; and treatment based on the biomarker.

Advantages of the system may include one or more of the following. The system may make medical trials more efficient. This will lower the costs that come about due to adverse drug side effects and prescription of drugs that have been proven ineffective in certain genotypes. Drug companies can develop and license a drug specifically intended for those who are the small population genetically at risk for adverse side effects.

These and other features of the present invention will become readily apparent upon further review of the following specification and drawings.

BRIEF DESCRIPTION OF THE DRAWINGS

FIG. 1B is a perspective view of an exemplary IoT fitness device system.

FIG. 1C is an exemplary process supported by the device according to the present invention.

FIG. 11A shows exemplary smart rackets while

FIG. 12A-12B show exemplary protective gears, while

FIG. 13A shows an exemplary system to collect lifestyle and genetic data from various populations for subsequent prediction and recommendation to similarly situated users.

FIG. 13B show exemplary substance interaction management processes;

FIG. 13E shows a big data learning machine to process genetic data and determine pharmacogenetics relationship among genes and drugs for drug interaction purposes.

FIGS. 14E-14F shows a system where expert oncologists collaborate with non-specialists in applying the DSS for genomic healthcare.

FIGS. 15A-15E show exemplary medical analysis system for IOT genomic and blockchain processing.

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION OF THE PREFERRED EMBODIMENTS

According to various embodiments of the present disclosure, an electronic device may include communication functionality. For example, an electronic device may be a smart phone, a tablet Personal Computer (PC), a mobile phone, a video phone, an e-book reader, a desktop PC, a laptop PC, a netbook PC, a Personal Digital Assistant (PDA), a Portable Multimedia Player (PMP), an MP3 player, a mobile medical device, a camera, a wearable device (e.g., a Head-Mounted Device (HMD), electronic clothes, electronic braces, an electronic necklace, an electronic accessory, an electronic tattoo, or a smart watch), and/or the like.

Figure 1A:
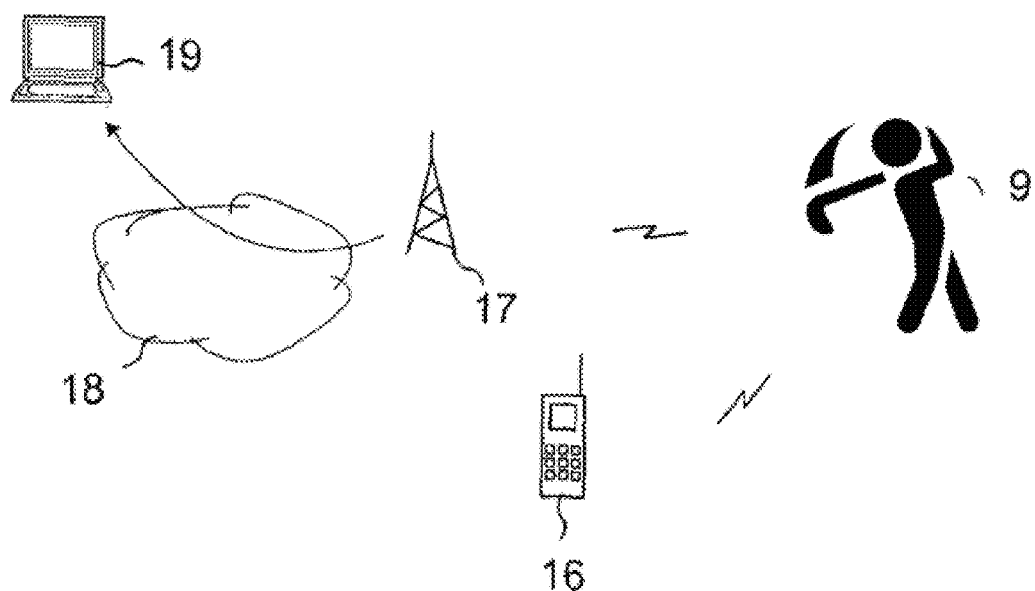
FIG. 1A illustrates an exemplary environment for communicating data from a monitoring device to external computers

FIG. 1A illustrates an exemplary environment for communicating data from a monitoring device to external computers. In FIG. 1A, the monitoring device used for a sport device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the sport device in a cradle or base. All parts of the monitoring device may be encapsulated with each other and/or may be integrated into or attached to the body of the sport device 9. Alternatively, a radio transmitter may be arranged separately from the other parts, for instance, in a battery charger, cradle or base of the sport device 9. In that example, the interface 7 may include contact terminals in the sport device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the sport device 9 has been used or the need to provide a replacement sport device. FIG. 1A also illustrates an alternate example of a transmitter, using an intermediate receiver 17 and a network 18, such as a cellular radio system. Also in this example, the radio transmitter may be located in connection with the sport device 9 or alternatively in connection, with a charger, cradle or base station of the sport device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the sport device 9 to the remote device 19, 16.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the sport device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user sport techniques.

Figure 2B:
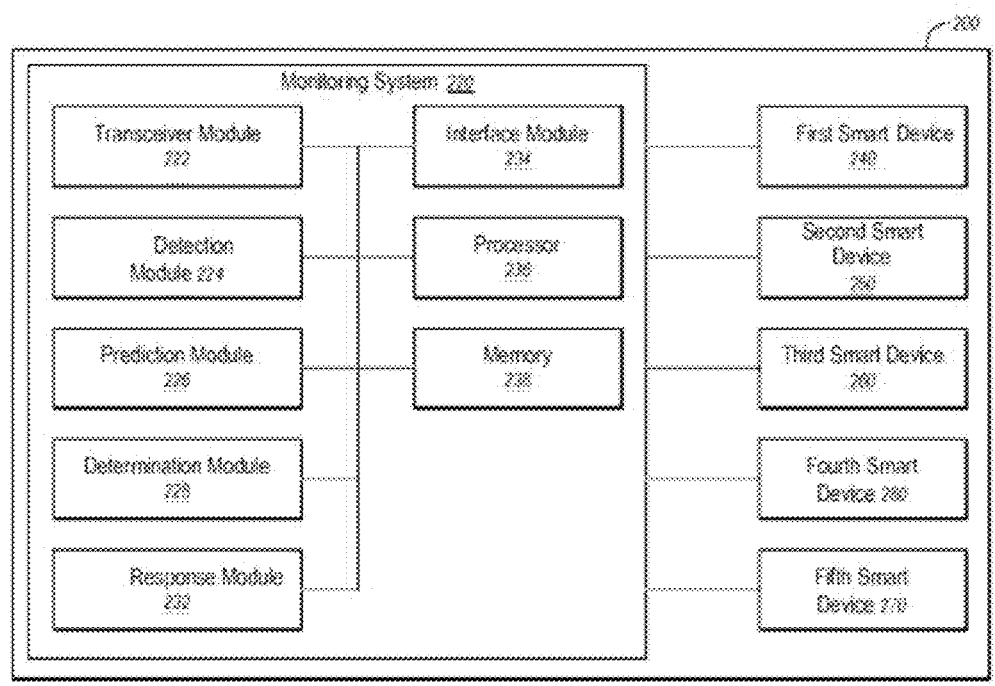
FIG. 2B is a block diagram of a big data system for predicting stress experienced by a structural unit such as a bridge, a building, or a plane, for example.
Figure 2A:
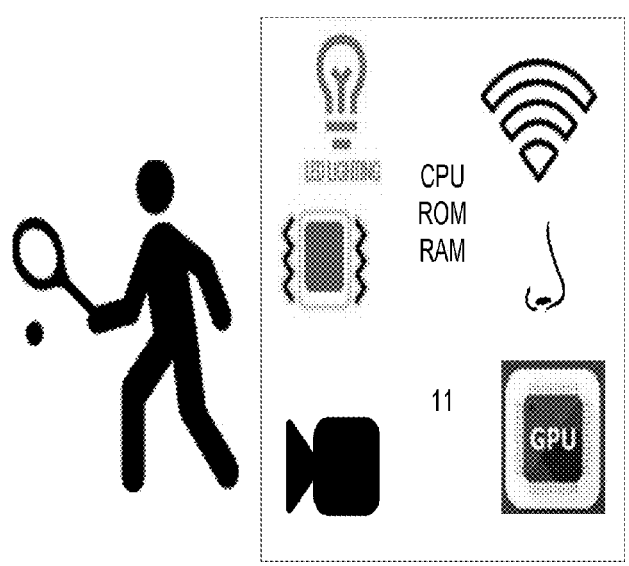
FIG. 2A is a block diagram of an electronic circuit for a smart device.
Figure 2A:
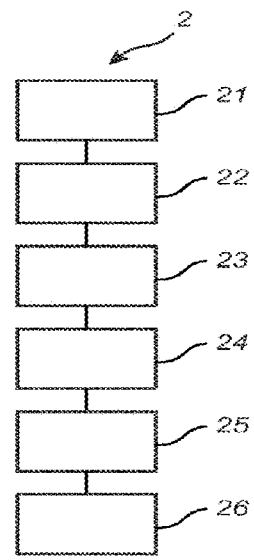
Figure 2A:
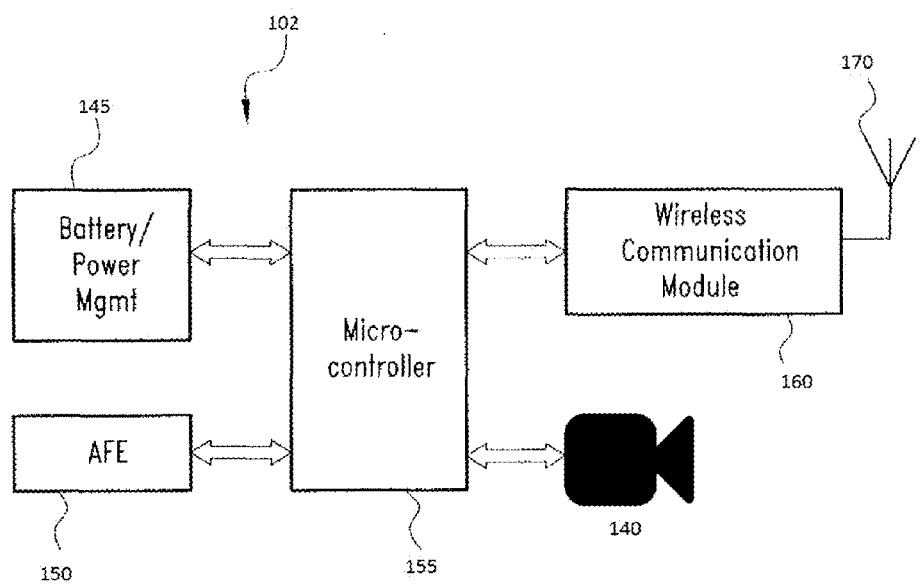

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides. Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/ Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third sport smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the sport object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
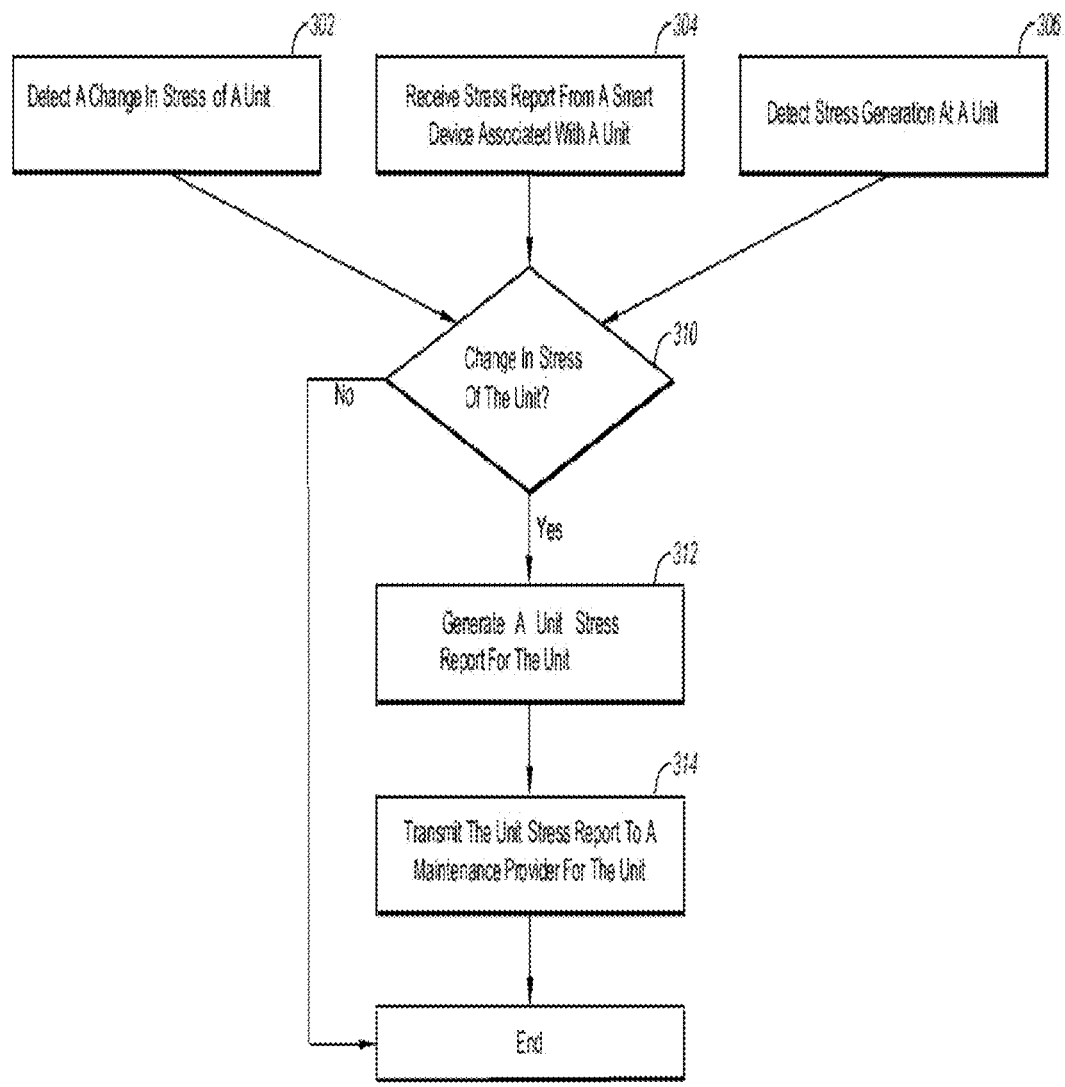
FIG. 3 is a flowchart illustrating one operation of the system of FIG. 2A-2B in detecting stress on a unit.

FIG. 3 is a flow chart of an example method 300 of monitoring stress of a sport or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, a stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, an stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
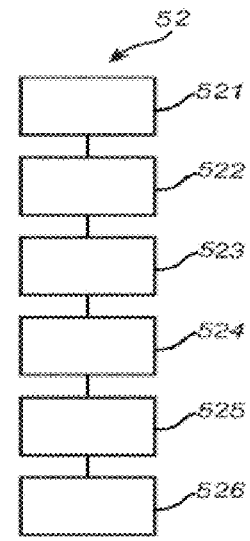
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:
- (51) capture 360 degree view of the live event
- (52) detect head position of the viewer
- (53) adjust viewing angle on screen based on head position and user posture
- (54) render view to simulate action based on user control rather than what the professional is doing
- (55) augment view with a simulated object that is powered by viewer action as detected by sensors on viewer body
- (56) compare professional result with simulated result and show result to a crowd of enthusiasts for social discussion.

Figure 4:
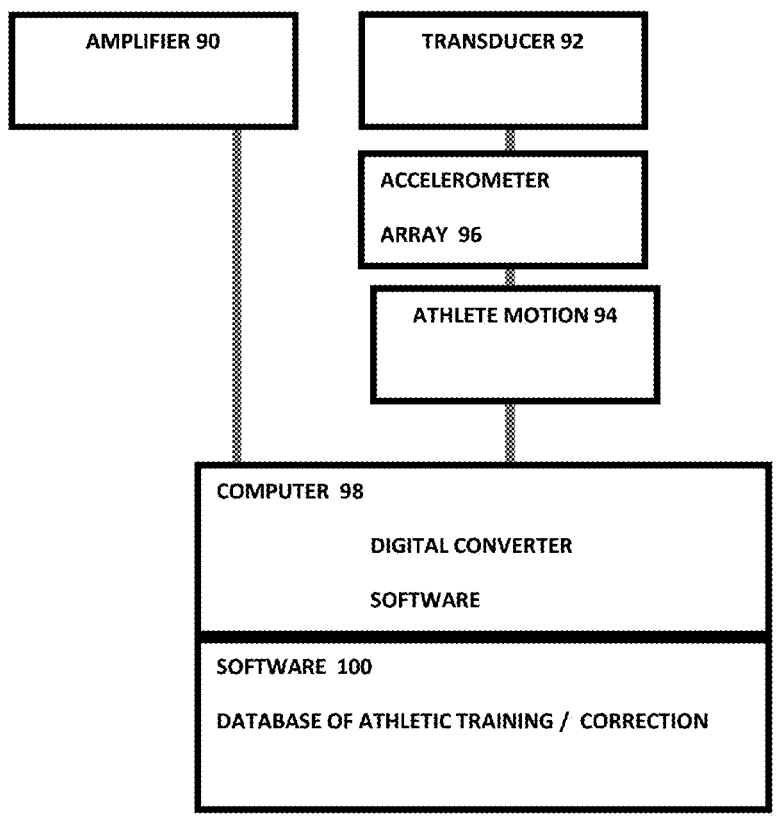
FIG. 4 shows an exemplary sports diagnosis and trainer system for augmented and/or virtual reality.
Figure 6:
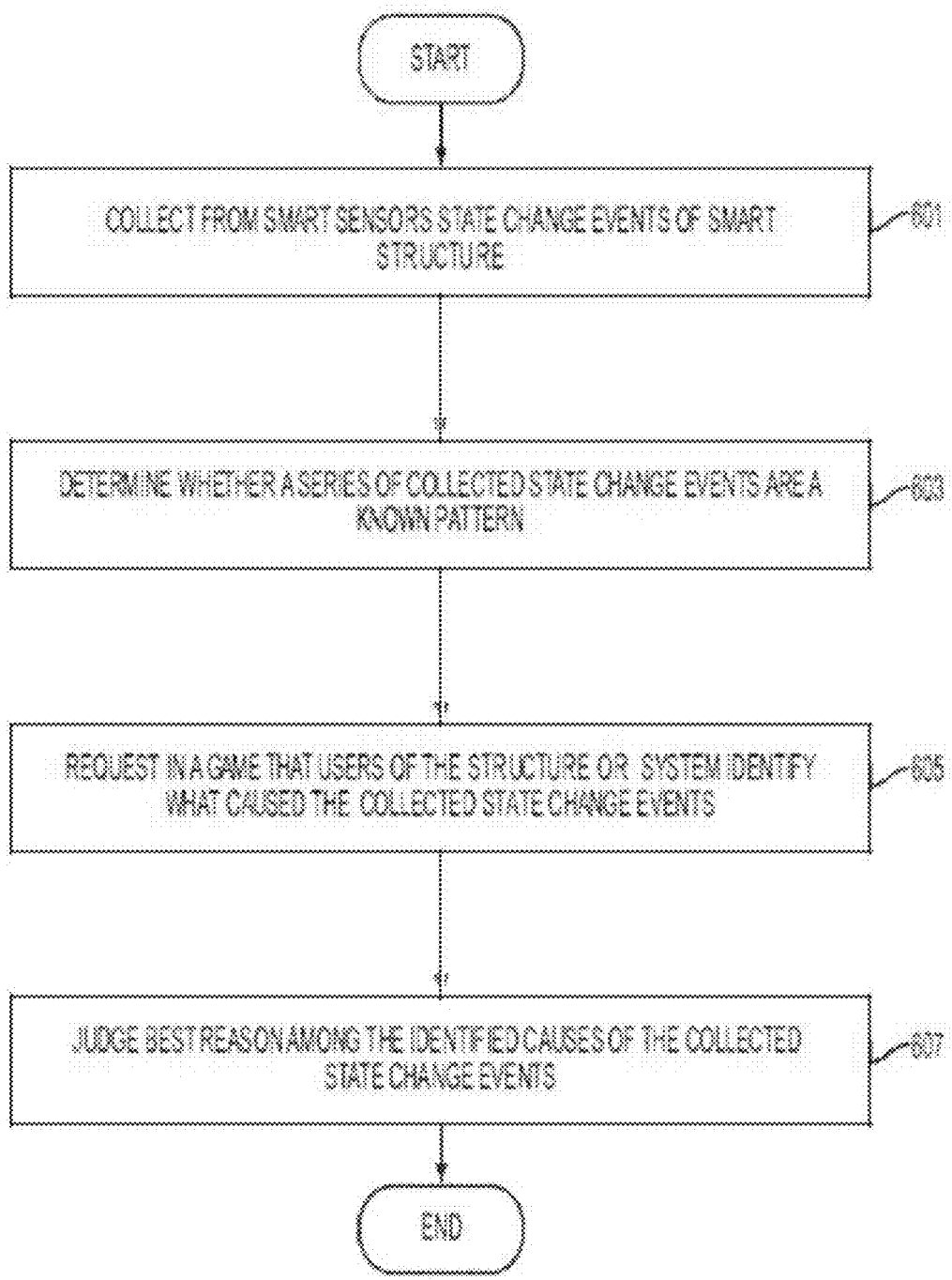
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart systems trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the each user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help sport enthusiasts improve dental care or maintain teeth hygiene. This may involve use of virtual tools, corresponding to such tools used in normal dental hygiene: sport device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Sport Glove

Figure 7:
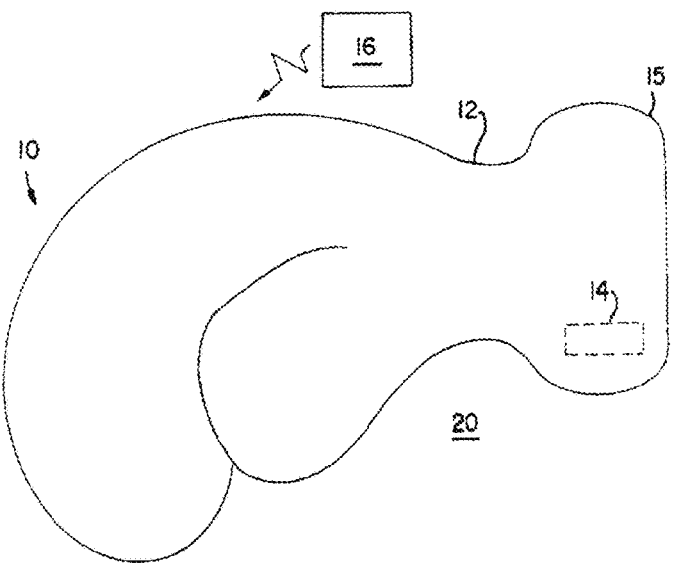
FIG. 7 shows an exemplary glove.

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. The impact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

Smart Sport Band

Figure 8:
FIG. 8 shows an exemplary smart band.

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bio-electrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

Figure 9:
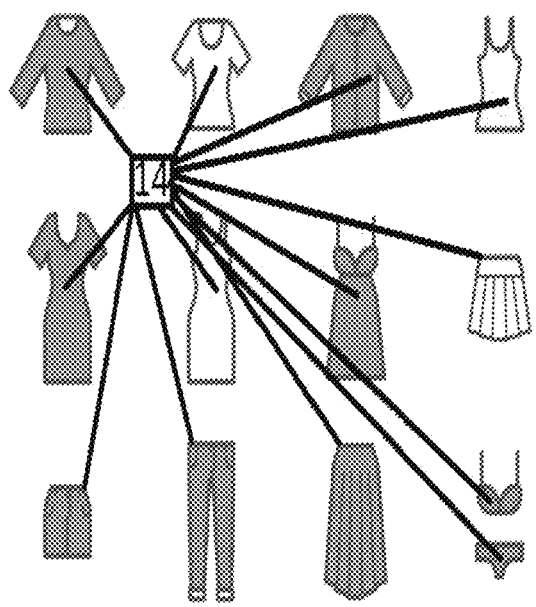
FIG. 9 shows exemplary smart clothing.
Figure 10:
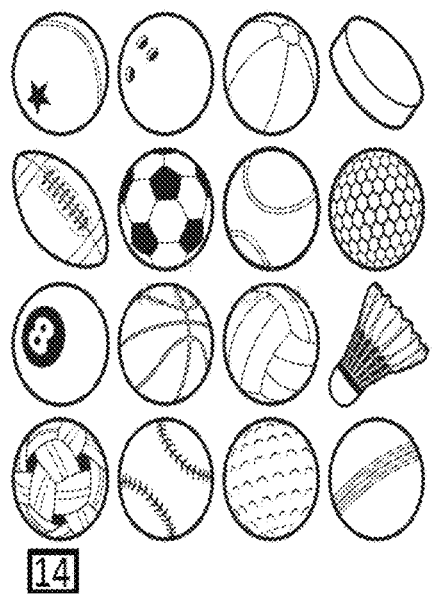
FIG. 10 shows exemplary smart balls.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable running conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multilayered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source)) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc Smart Clothing FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

1. A smart clothing, comprising:
    a shirt, underwear, pant or sock;
    a band to be secured to the a shirt, underwear, pant or sock;
    a processor in the band and coupled to a wireless transceiver;
    an EKG amplifier coupled to the band;
    a sensor disposed in the band; and
    an accelerometer disposed within the band to detect acceleration of the band.
2. The clothing of claim 1, comprising a plurality of bands forming a mesh network and communicating episodically to conserve power.
3. The clothing of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).
4. The clothing of claim 1 comprised for sensing and/or monitoring impact events where the sensors are accelerometers, gyroscopes, and/or pressure sensors.
5. The clothing of claim 1 comprised for sensing and/or monitoring and/or controlling ongoing events where the sensors monitor temperature, temperature gradients, motion, position, environmental or chemical levels, or other such information.
6. The clothing of claim 1 comprised for sensing events or other information including mounting multiple distributed sensors for obtaining spatial and/or temporal distribution in the data and/or multiple sensors sensing different information and data.
7. The clothing of claim 1 including wired or wireless communication, such as a Bluetooth module or a wi-fi module or other transmission module, transmitting and/or receiving information to/from another device.
8. The clothing of claim 1 with power and energy sources including batteries, wired or wireless rechargeable batteries, photovoltaics, thermoelectrics, or energy harvesters.
9. The clothing of claim 1 with an adhesive backing for directly adhering to a head, a body, or an object.
10. The clothing of claim 1 contained in an adhesive or a sleeve for adhering or attaching to a head, a body, or an object.
11. The clothing of claim 1 coated with a coating for protection against the elements (water, moisture, dirt, other) and/or for increased comfort to the wearer.
12. The clothing of claim 1, comprising a geometrically patterned substrate that contains regions of low strain domains (LSDs) bridged by hingable strain relief features (SRFs) which also contain low strain regions and enable the stretching, flexing and twisting of the patch while maintaining continuous low strain regions for mounting electronic components and routing traces.
13. The clothing of claim 1 for attachment to or on or an object, or embedded in an object.
14. The clothing of claim 1 in the form factor of a rectangular or a square or a triangular or other polygon or circular or elliptical or other geometric shape bandage.

15. The clothing of claim 1 in the form factor that is or contains any combination of rectangles, triangles, circles, ellipses or other form factors.
16. The clothing of claim 1 with different geometric patterning of different numbers and shapes and orientations of low strain domains, different numbers and orientation of geometrically structured hinge-like domains, and different geometries of hinge-like domains.
17. The clothing of claim 1 as a programmable circuit board for arbitrary applications.
18. The clothing of claim 1 fabricated using current flex circuit manufacturing methods and materials.
19. The clothing of claim 1 comprising a cloud storage to receive sensor data.
20. The clothing of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Handle

Figure 11A:
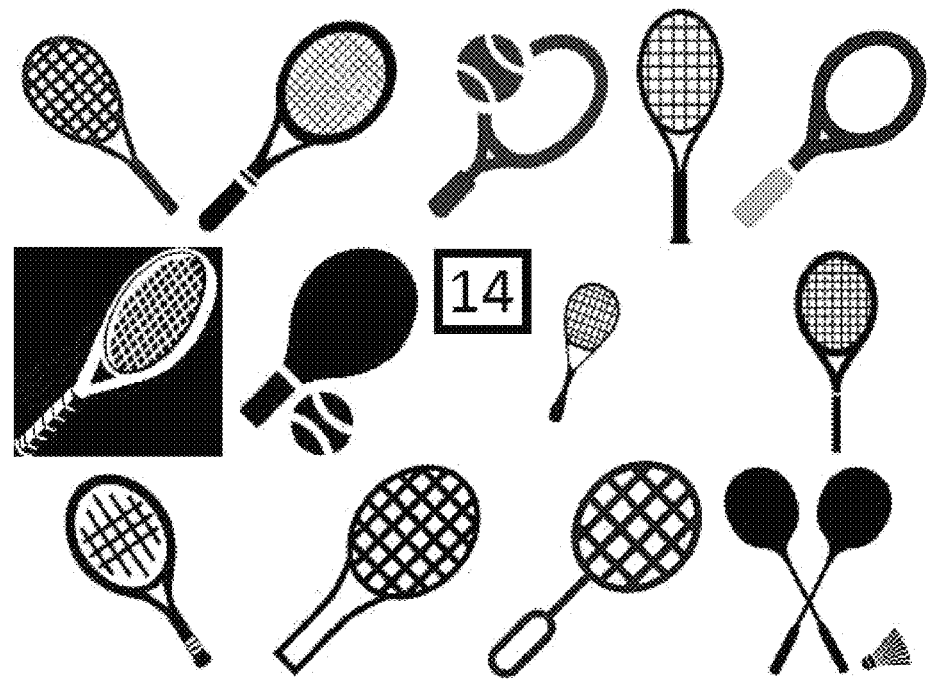
Figure 11B:
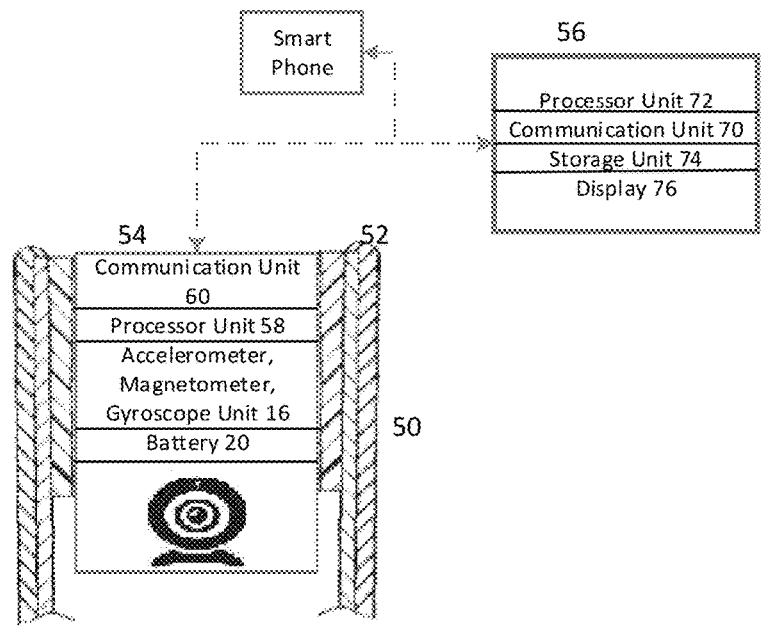
FIG. 11B shows electronics in the handle for toothbrush, golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Smart Protective Gear

Figure 12A:
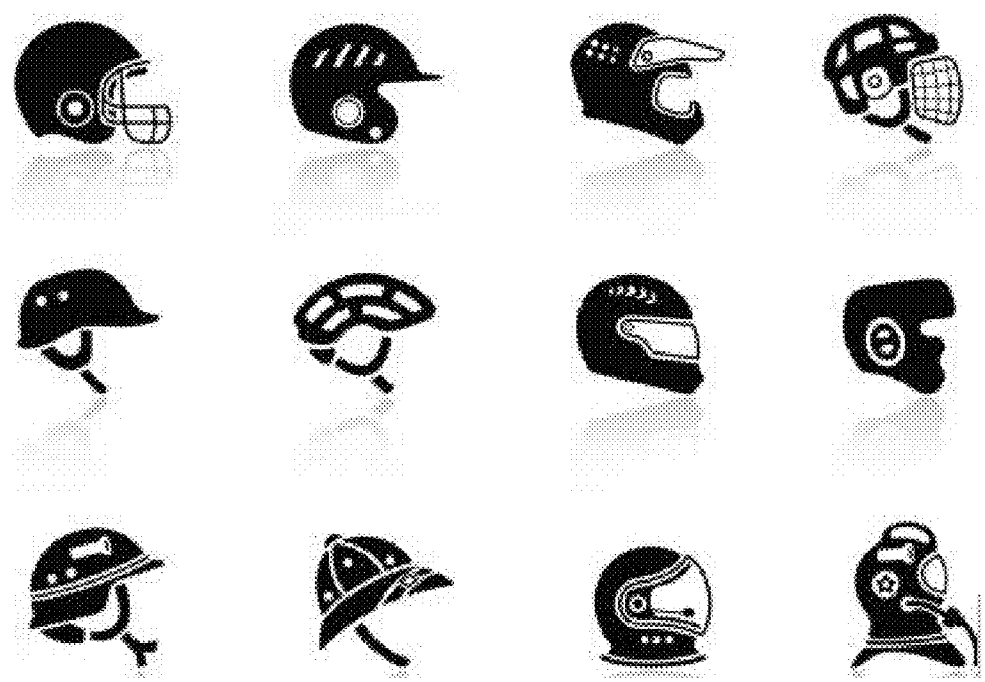
Figure 12C:
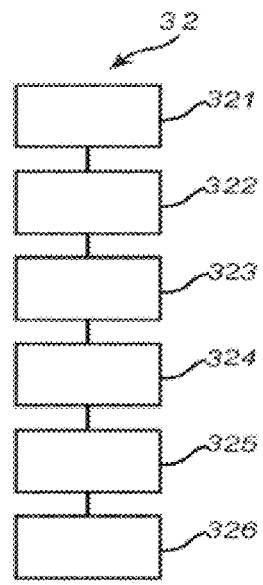
FIG. 12C shows an exemplary process to fabricate mass-customized protective gear.
Figure 12B:
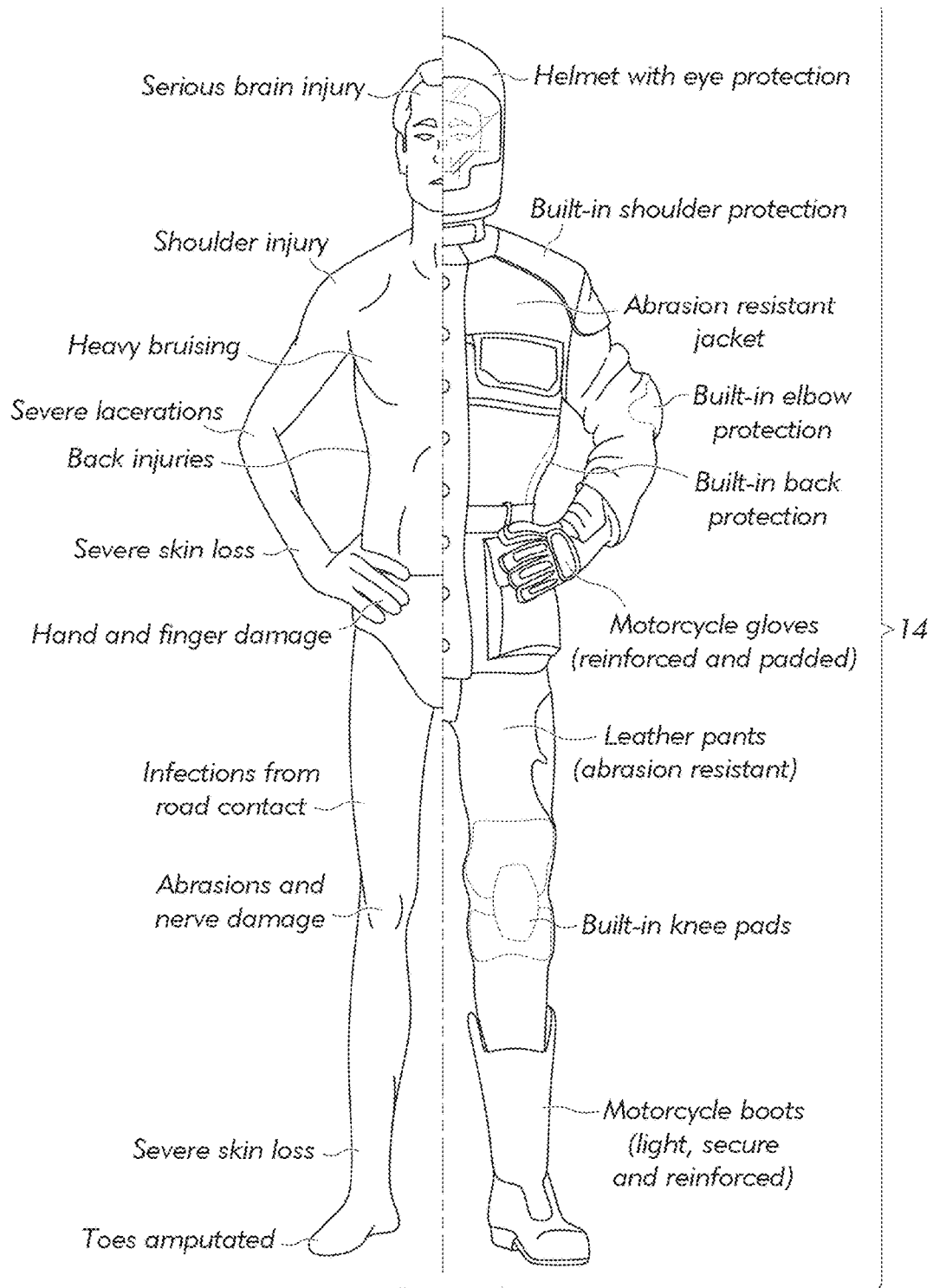

FIGS. 12A-12C illustrate smart protective gears embedded with the IoT sensors and instrumentations to report potential health issues. More details are in the incorporated by reference parent application. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others. In accordance with aspects of the subject matter disclosed herein through the use of reformable bed and a suitably programmed CNC tools, customized footwear with custom cut sole designs, can cost effectively be created in small quantities and yet scalable for mass-customization.

1. A method of producing a component of customized wearable protection gear, the method comprising:
    capturing the 3D model of a person and adjusting the 3D model to customize a shape to optimize protection or performance;
    using a rapid prototyping machine such as 3D printer or a bed of pins to render a positive model of the shape; and
    impressing the positive model into a reformable mold to form the component of the wearable protective gear.
2. The method of claim 1, wherein the component comprises a helmet, protective padding, shoulder padding, seat, shoe, or sole.
3. The method of claim 1, comprising fabricating a plurality of components in parallel.
4. The method of claim 1, wherein the component comprises shin guard, Helmet, Chin Strap, Chin Shields, Cup, Athletic Supporter, Elbow Sleeve, Arm Pad, Back Plate, Rib Protection, Facemask, Girdle, Helmet Visor, Shoulder Pad, Hip & Tail Pad, Mouthguard, Neck Roll, Knee Pad, Boot.
5. The method of claim 1, comprising joining the component with an upper to form a shoe.
6. The method of claim 5, wherein the shoe comprises a jogging shoe, basketball shoe, soccer shoe, miming shoe, climbing shoe, flip flop, sandal, or boot.
7. The method of claim 1, wherein the reformable mold comprises sand having a liquid state and a solid state.

FIG. 13A shows an exemplary system to collect lifestyle and genetic data from various populations for subsequent prediction and recommendation to similarly situated users. The system collects attributes associated with individuals that co-occur (i.e., co-associate, co-aggregate) with attributes of interest, such as specific disorders, behaviors and traits. The system can identify combinations of attributes that predispose individuals toward having or developing specific disorders, behaviors and traits of interest, determining the level of predisposition of an individual towards such attributes, and revealing which attribute associations can be added or eliminated to effectively modify his or her lifestyle to avoid medical complications. Details captured can be used for improving individualized diagnoses, choosing the most effective therapeutic regimens, making beneficial lifestyle changes that prevent disease and promote health, and reducing associated health care expenditures. It is also desirable to determine those combinations of attributes that promote certain behaviors and traits such as success in sports, music, school, leadership, career and relationships.

For example, the system captures information on epigenetic modifications that may be altered due to environmental conditions, life experiences and aging. Along with a collection of diverse nongenetic attributes including physical, behavioral, situational and historical attributes, the system can predict a predisposition of a user toward developing a specific attribute of interest. In addition to genetic and epigenetic attributes, which can be referred to collectively as pangenetic attributes, numerous other attributes likely influence the development of traits and disorders. These other attributes, which can be referred to collectively as non-pangenetic attributes, can be categorized individually as physical, behavioral, or situational attributes.

FIG. 13A displays one embodiment of the attribute categories and their interrelationships according to the present invention and illustrates that physical and behavioral attributes can be collectively equivalent to the broadest classical definition of phenotype, while situational attributes can be equivalent to those typically classified as environmental. In one embodiment, historical attributes can be viewed as a separate category containing a mixture of genetic, epigenetic, physical, behavioral and situational attributes that occurred in the past. Alternatively, historical attributes can be integrated within the genetic, epigenetic, physical, behavioral and situational categories provided they are made readily distinguishable from those attributes that describe the individual's current state. In one embodiment, the historical nature of an attribute is accounted for via a time stamp or other time based marker associated with the attribute. As such, there are no explicit historical attributes, but through use of time stamping, the time associated with the attribute can be used to make a determination as to whether the attribute is occurring in what would be considered the present, or if it has occurred in the past. Traditional demographic factors are typically a small subset of attributes derived from the phenotype and environmental categories and can be therefore represented within the physical, behavioral and situational categories.

An individual possesses many associated attributes which may be collectively referred to as an 'attribute profile' associated with that individual. In one embodiment, an attribute profile can be considered as attributes that are present (i.e., occur) in that profile, as well as being comprised of the various combinations (i.e., combinations and subcombinations) of those attributes. The attribute profile of an individual is preferably provided to embodiments of the present invention as a dataset record whose association with the individual can be indicated by a unique identifier contained in the dataset record. An actual attribute of an individual can be represented by an attribute descriptor in attribute profiles, records, datasets, and databases. Herein, both actual attributes and attribute descriptors may be referred to simply as attributes. In one embodiment, statistical relationships and associations between attribute descriptors are a direct result of relationships and associations between actual attributes of an individual. In the present disclosure, the term 'individual' can refer to a singular group, person, organism, organ, tissue, cell, virus, molecule, thing, entity or state, wherein a state includes but is not limited to a state-of-being, an operational state or a status. Individuals, attribute profiles and attributes can be real and/or measurable, or they may be hypothetical and/or not directly observable.

Since the system captures information from various diverse populations, the data can be mined to discover combinations of attributes regardless of number or type, in a population of any size, that cause predisposition to an attribute of interest. The ability to accurately detect predisposing attribute combinations naturally benefits from being supplied with datasets representing large numbers of individuals and having a large number and variety of attributes for each. Nevertheless, the present invention will function properly with a minimal number of individuals and attributes. One embodiment of the present invention can be used to detect not only attributes that have a direct (causal) effect on an attribute of interest, but also those attributes that do not have a direct effect such as instrumental variables (i.e., correlative attributes), which are attributes that correlate with and can be used to predict predisposition for the attribute of interest but are not causal. For simplicity of terminology, both types of attributes are referred to herein as predisposing attributes, or simply attributes, that contribute toward predisposition toward the attribute of interest, regardless of whether the contribution or correlation is direct or indirect.

In illustration, FIG. 13B show exemplary processes for computer detection of substances or drugs for drug interaction information retrieval. Turning now to FIG. 1B, a camera based drug identification and drug interaction management system is shown. In 110, images of a substance such as a drug can be acquired. In 120 the process identifies content for the substance can be retrieved from the image. In 130, substances can be identified according to the identifying content. In 140, the identified substance can be added to an interaction list. In 150 the process loops back to 110 if additional substances remain to be imaged and if not, the interaction list now populated by a list of imaged substances can be processed. In 160, the process receives genetic scans for subjects. In 170, the process retrieves drug data and drug interaction data for each of the imaged substances and determines relative interactions between substances, and in 180 pharmacogenomic information is applied to select the best medication and identify people who need an unusually high or low dose. In 190, the relative interactions can be rendered within a report such as a paper report or a graphical user interface display.

While FIG. 13B discusses capturing drug interaction, the process can be used to capture environmental factors of FIG. 13A. In yet other embodiments, the process cryptographically reads substance content from RF tag or barcode on a secure bottle and identifies content for the substance. Identified substances are added to an interaction list and the process determines if additional substances remain to be scanned (RF/Bar Code) and continues processing. The interaction list now populated by a list of scanned substances is processed. Next, the process retrieves drug data and drug interaction data for each of the scanned substances and determines relative interactions between substances. The process receives genetic scans for subjects. The process applies pharmacogenomic information to the drug-gene interaction data and selects the best medication and identify people who need an unusually high or low dose. Relative interactions can be rendered within a report such as a paper report or a graphical user interface display.

The process shown in FIG. 13B can be implemented within a data processing system. In further illustration, FIG. 213C schematically depicts a data processing system configured for computer visualization of drugs for drug interaction information retrieval. The system can include a host computing platform 202 coupled to a camera 220 such as a digital still camera or digital video camera. The camera 220 can be focused on a marshalling point 240 provided by a marshalling apparatus 230, for example gravity feed or isolation chamber or miniature conveyor belt. The host computing platform 202 also can be communicatively coupled a drug image data store 250 of known substances and corresponding known identifying content visually disposed on the known substances. The host computing platform 202 additionally can be communicatively coupled to a drug interaction data store 260 providing drug interaction data for different substances relative to other substances including prescription and over-the-counter drugs, vitamins and herbal remedies, and food products.

Figure 13C:
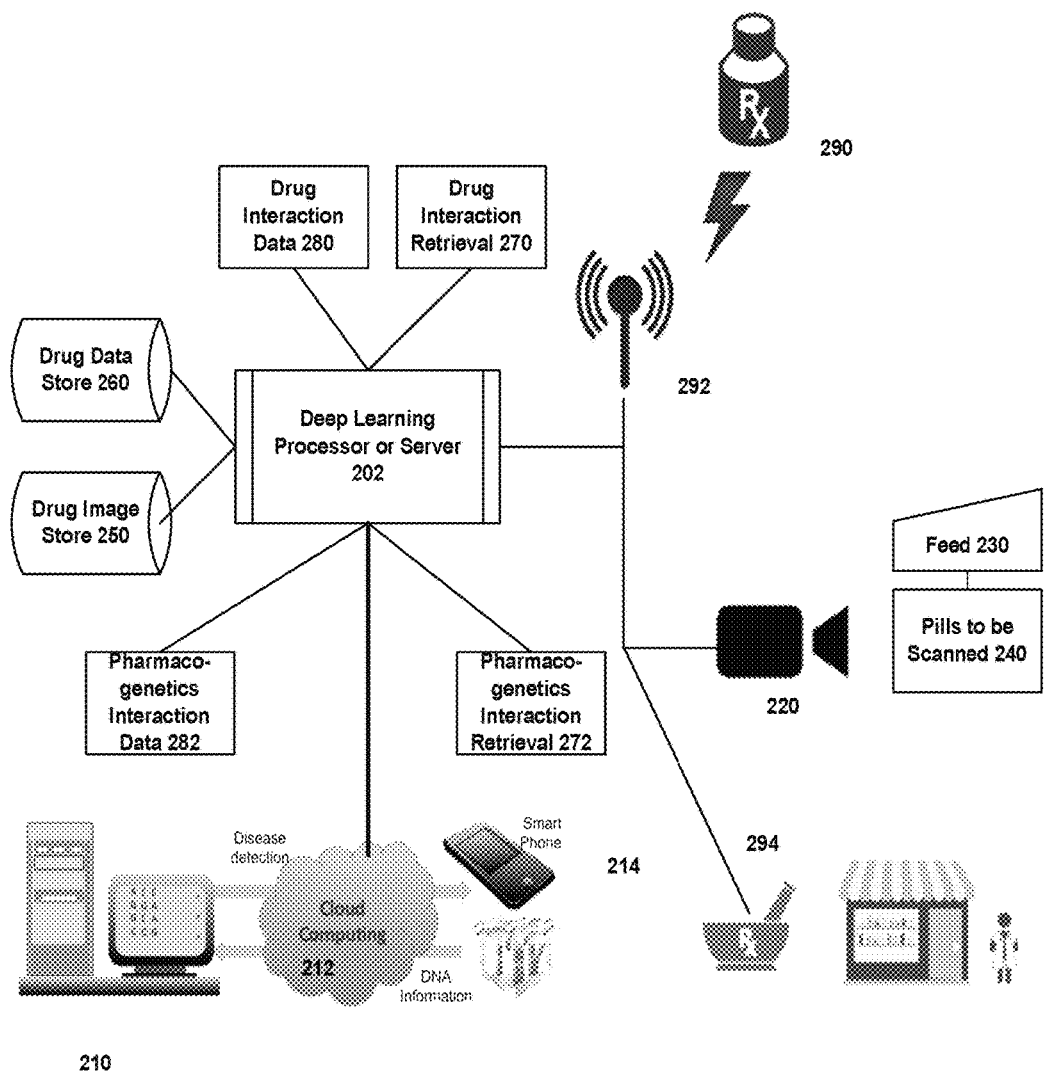
FIG. 13C is a schematic illustration of a data processing system configured for computer management genetic information, precision medication and drug interaction information retrieval; and, FIG. 13D is a flow chart illustrating a process for pharmacogenetics drug interaction information retrieval.

In one embodiment of FIG. 13C, multiple different substances such as prescription drugs, over-the-counter drugs or even vitamins and herbal remedies can be provided to a marshalling apparatus such as a gravity feed or miniature conveyor belt or even a chamber. The marshalling apparatus can isolate an individual one of the different substances for imaging by camera 220, for example a charge coupled device (CCD) driven digital camera or video recorder. The camera 220 can capture an image of each individual one of the different substances 110A, 110B, 110N and computer visualization for drug interaction information retrieval logic 300 can process each captured image to detect identifying content disposed on each of the different substances such as a pill marking or code. The computer visualization for drug interaction information retrieval logic 300 in turn can compare the identified content to a data store of known substances 140 to identify each of the different substances. The computer can lookup not only known drug interactions for each of the different substances, but also known drug interactions between the identified ones of the substances and pharmacogenetics impact on the individual patient. Thereafter, a drug interaction report can be produced indicating the known drug interactions between the identified ones of the substances.

The host computing platform 202 can support the execution of computer scanning or visualization for drug interaction information retrieval logic 270. The logic can include program code enabled to acquire imagery of different substances in the marshalling point 240. The program code further can be enabled to locate and retrieve identifying content disposed on the different substances and to look up the identifying content in the drug image data store 250 in order to identify each of the substances. The program code yet further can be enabled to retrieve from drug interaction data store 260 drug interactions for each of the identified substances and to particularly correlate the retrieved drug interactions to different ones of the substances so that relative drug interactions can be determined for the substances. Finally, the program code can be enabled to render a report of drug interaction data in a graphical user interface display 280 of drug interaction data.

The computing platform 202 also receives pharmacogenetics interaction 282. Notably, the host computing platform 202 can support the execution of computer visualization for pharmacogenetics interaction information retrieval logic 272. Genetic information is captured by high speed gene sequencing machine 210 that uploads gene data to a cloud computing network 212. The doctors, pharmacists, or consumers can access DNA information using mobile computers such as smart phone 214, for example.

The system can have wireless communication 292 with the medication's labels. For example, the labels can have RF tags or NFC tags that provide upon inquiry FDA required labeling contents. In one embodiment, the content can be genomic biomarkers; drug exposure and clinical response variability; risk for adverse events; genotype-specific dosing; polymorphic drug target and disposition genes; and treatment based on the biomarker. NFC tags are passive devices and operate without a power supply of their own and are reliant on an active device to come into range before they are activated. To power these NFC tags, electromagnetic induction is used to create a current in the passive device. Active devices, such as a reader or a smartphone, are responsible for generating the magnetic field with a simple coil of wire, which produces magnetic fields perpendicular to the flow of the alternating current in the wire. To reduce power, NFC operates over just a few inches, rather than the meters in other types of wireless communication.

The system can be used to provide personalized medicine through custom pharmacy compounding 294 or custom production of a drug whose various properties (e.g. dose level, ingredient selection, route of administration, etc.) are selected and crafted for an individual patient (in contrast to mass-produced unit doses or fixed-dose combinations).

The genetic scan in 70 can be generated by gene sequencing machines. DNA sequencing is the process of determining the precise order of nucleotides within a DNA molecule. It includes any method or technology that is used to determine the order of the four bases—adenine, guanine, cytosine, and thymine—in a strand of DNA. Various high speed sequencers can be used. For example, Nanopore DNA sequencing is based on the readout of electrical signals occurring at nucleotides passing by alpha-hemolysin pores covalently bound with cyclodextrin. The DNA passing through the nanopore changes its ion current. Oxford Nanopore Technologies offers a handheld sequencer capable of generating more than 150 megabases of sequencing data in one run.

Another approach uses measurements of the electrical tunneling currents across single-strand DNA as it moves through a channel. Depending on its electronic structure, each base affects the tunneling current differently, allowing differentiation between different bases. The use of tunneling currents has the potential to sequence orders of magnitude faster than ionic current methods and the sequencing of several DNA oligomers and micro-RNA has already been achieved. Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify its sequence in the DNA being sequenced. Mass spectrometry may be used to determine DNA sequences. Matrix-assisted laser desorption ionization time-of-flight mass spectrometry, or MALDI-TOF MS, has specifically been investigated as an alternative method to gel electrophoresis for visualizing DNA fragments. With this method, DNA fragments generated by chain-termination sequencing reactions are compared by mass rather than by size. The mass of each nucleotide is different from the others and this difference is detectable by mass spectrometry. Single-nucleotide mutations in a fragment can be more easily detected with MS than by gel electrophoresis alone. MALDI-TOF MS can more easily detect differences between RNA fragments, so researchers may indirectly sequence DNA with MS-based methods by converting it to RNA first. In microfluidic Sanger sequencing the entire thermocycling amplification of DNA fragments as well as their separation by electrophoresis is done on a single glass wafer (approximately 10 cm in diameter) thus reducing the reagent usage as well as cost. Microscopy-based technique directly visualizes the sequence of DNA molecules using electron microscopy. RNAP sequencing is based on use of RNA polymerase (RNAP), which is attached to a polystyrene bead. One end of DNA to be sequenced is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types, similarly to the Sanger method. Other high speed gene sequencers can be used.

The system applies pharmacogenomic information to select the best medication and identify people who need an unusually high or low dose. This is in addition to clinical factors, such as a patient's age, weight, sex, and liver and kidney function. Pharmacogenomics (sometimes called pharmacogenetics) is focused on understanding how genes affect individual responses to medications and to help doctors select the drugs and dosages best suited for each person. Pharmacogenomics looks at variations in genes for proteins that influence drug responses. Such proteins include a number of liver enzymes that convert medications into their active or inactive forms. Even small differences in the genetic sequences of these enzymes can have a big impact on a drug's safety or effectiveness. One example involves a liver enzyme known as CYP2D6. This enzyme acts on a quarter of all prescription drugs, including the painkiller codeine, which it converts into the drug's active form, morphine. The CYP2D6 gene exists in more than 160 different versions, many of which vary by only a single difference in their DNA sequence, although some have larger changes. The majority of these variants don't affect drug responses. Some people have hundreds or even thousands of copies of the CYP2D6 gene (typically, people have two copies of each gene). Those with extra copies of this gene manufacture an overabundance of CYP2D6 enzyme molecules and metabolize the drug very rapidly. As a result, codeine may be converted to morphine so quickly and completely that a standard dose of the drug can be an overdose. On the other end of the spectrum, some variants of CYP2D6 result in a nonfunctional enzyme. People with these variants metabolize codeine slowly, if at all, so they might not experience much pain relief. For these people, doctors might prescribe a different type of pain reliever. Pharmacogenomic information can cover dosage guidance, possible side effects or differences in effectiveness for people with certain genomic variations—can help doctors tailor their drug prescriptions for individual patients. The system applies pharmacogenomic data to develop and market drugs for people with specific genetic profiles. The system can identify the genetic basis for certain serious side effects, drugs could be prescribed only to people who are not at risk for them. As a result, potentially lifesaving medications, which otherwise might be taken off the market because they pose a risk for some people, could still be available to those who could benefit from them. For example, a few drug and gene associations are listed in the Appendix.

It will be recognized by the skilled artisan that while the computer visualization for drug interaction information retrieval logic 270 is shown to execute in a single host computing platform 202, the invention is not so limited and the computer visualization for drug interaction information retrieval logic 270 also can be distributed in form across multiple different computing platforms. Further, the camera 220 and marshalling apparatus 230 can be located remotely from the host computing platform 202 whilst providing acquired imagery to the host computing platform 210 over a computer communications network, whether wireless or wirebound. Yet further, either or both of the drug image data store 250 and the drug interaction data store 260 can be remotely disposed from the host computing platform 202 and accessible over a computer communications network, whether wireless or wirebound.

The system enables a medical model that separates patients into different groups—with medical decisions, practices, interventions and/or products being tailored to the individual patient based on their predicted response or risk of disease.

Having the ability to look at a patient on an individual basis will allow for a more accurate diagnosis and specific treatment plan. Genotyping is the process of obtaining an individual's DNA sequence by using biological assays. By having a detailed account of an individual's DNA sequence, their genome can then be compared to a reference genome, like that of the Human Genome Project, to assess the existing genetic variations that can account for possible diseases. An individual's genetic make-up also plays a large role in how well they respond to a certain treatment, and therefore, knowing their genetic content can change the type of treatment they receive. The system applies pharmacogenomics by using an individual's genome to provide a more informed and tailored drug prescription. Often, drugs are prescribed with the idea that it will work relatively the same for everyone, but in the application of drugs, there are a number of factors that must be considered. The detailed account of genetic information from the individual will help prevent adverse events, allow for appropriate dosages, and create maximum efficacy with drug prescriptions. The pharmacogenomic process for discovery of genetic variants that predict adverse events to a specific drug has been termed toxgnostics.

In addition to specific treatment, personalized medicine can greatly aid the advancements of preventive care. For instance, many women are already being genotyped for certain mutations in the BRCA1 and BRCA2 gene if they are predisposed because of a family history of breast cancer or ovarian cancer. As more causes of diseases are mapped out according to mutations that exist within a genome, the easier they can be identified in an individual. Measures can then be taken to prevent a disease from developing. Even if mutations were found within a genome, having the details of their DNA can reduce the impact or delay the onset of certain diseases. Having the genetic content of an individual will allow better guided decisions in determining the source of the disease and thus treating it or preventing its progression. This will be extremely useful for diseases like Alzheimer's or cancers that are thought to be linked to certain mutations in human DNA.

The system can be used to test efficacy and safety of a drug specific to a targeted patient group/sub-group is companion diagnostics. This technology is an assay that is developed during or after a drug is made available on the market and is helpful in enhancing the therapeutic treatment available based on the individual. These companion diagnostics have incorporated the pharmacogenomic information related to the drug into their prescription label in an effort to assist in making the most optimal treatment decision possible for the patient.

Having an individual's genomic information can be significant in the process of developing drugs as they await approval from the FDA for public use. Having a detailed account of an individual's genetic make-up can be a major asset in deciding if a patient can be chosen for inclusion or exclusion in the final stages of a clinical trial. Being able to identify patients who will benefit most from a clinical trial will increase the safety of patients from adverse outcomes caused by the product in testing, and will allow smaller and faster trials that lead to lower overall costs. In addition, drugs that are deemed ineffective for the larger population can gain approval by the FDA by using personal genomes to qualify the effectiveness and need for that specific drug or therapy even though it may only be needed by a small percentage of the population. Treatments can be more specifically tailored to an individual and give insight into how their body will respond to the drug and if that drug will work based on their genome. The personal genotype can allow physicians to have more detailed information that will guide them in their decision in treatment prescriptions, which will be more cost-effective and accurate.

The system next generates gene-environmental factor interactions to help lifestyle recommendations. The system creates a matrix that correlates gene and environmental impacts. One embodiment generates gene based drug-drug interactions that allow the physician or pharmacist to avoid health problems for the patient. FIG. 13D shows a method 300 for predicting drug-drug interactions based on genetic data and clinical side effects, in accordance with an embodiment of the present principles. The process includes the following: At 310, construct a comprehensive gene-drug-drug interactions (GDDIs) training dataset that includes all pharmaceutical, pharmacokinetic (PK), pharmacogenetic (PG), and pharmacodynamic (PD) GDDIs from multiple data sources for each drug in a set of drugs under consideration. In an embodiment, the multiple data sources can include, but are not limited to, the following: gene sequencers, clinical trials; drug development information; empirical information; a drug bank; drug label information; an adverse event reporting system (e.g., the FDA Adverse Event Reporting System information (FAERS)); and text mining from scientific documents (e.g., search tool for interactions of chemicals (STITCH)). At step 320, construct side effect features for each of the drugs in the set from genetic panels for an individual and side effects associated with the drugs in the set. In an embodiment, the genetic panels are generated by genetic sequencers, and all drugs' side effects, from which the side effect features are constructed, come from one or more of the following sources: clinical trials; drug development; empirical information; FDA drug label (SIDER and DAILYMED®); FDA Adverse Event Reporting System (FAERS); and real-world evidence. At 330, build, using the GDDIs training dataset, a GDDIs classifier for predicting whether or not a given drug pair derived from the set of drugs results in adverse interactions, and repeat this process for all possible drug pairs derivable from the set of drugs. In an embodiment, the features used for building the classifier can include, but are not limited to, the following: drug's clinical side effect keywords; and other drug properties (e.g., chemical structures, protein targets, and so forth).

At 340, obtain predicted GDDIs from the classifier. At 350, for each side effect, perform statistical test to determine whether that side effect is differentially shown between positive predicted GDDIs and negative predicted GDDIs. In one embodiment, the term "positive predicted GDDIs" refers to drugs pairs that cannot be taken together given a patient genetic profile. In contrast, the term "negative predicted GDDIs" refers to drugs pairs that may be safe to use together with a genetic profile.

Side effects are effects after taking a medicine, which are other than the intended therapeutic effects. Label side effects means the side effects are recorded in drug labels (for example, but not limited to, SIDER database, DAILYMED®, and so forth). FDA side effects means the side effects are recorded in, for example, but not limited to, the FDA Adverse Event Reporting System (FAERS). Consider, for example, the drug Ibuprofen as an example, DAILYMED® records its 249 types of label side effects (e.g., abdominal discomfort, confusion, dry mouth, vomiting, and weight loss), and FAERS records its 728 types of FDA side effects (e.g., anxiety, ear ache, fatigue, tooth loss, sleep disorder).

In 380, relative interactions between the different drug substances can be determined by locating references in the interaction data for each of the drug substances to others of the substances. Finally, in block 390, the relative interactions can be rendered within a report such as a paper report or a graphical user interface display. Optionally, an activatable link can be provided in the display for selected ones of the drug substances for reordering the selected ones of the drug substances. In this way, the relative drug interactions resulting from the dispensing of multiple different drug substances based on patient genetic data can be determined without requiring a tedious manual process of looking up drug interaction data for each substance and manually correlating the drug interaction data for the specific combination of dispensed substances.

The system can also perform GDDI discovery and prediction that uses molecular structure similarity information derived from fingerprint-based modeling. Identifying new GDDIs using structural similarity is based on the basic idea that if drug A interacts with drug B, and drug C is structurally similar to A, then C should also interact with B (the argument also follows if A is replaced with B). Hence, by combining knowledge of known interactions with structural similarity it is possible to identify new interactions. The process uses a list of drug-drug interactions from DrugBank (step 1), structural similarity computation was carried out using molecular fingerprints (step 2), apply gene-drug interaction to similar drugs, and a new list of gene-drug interactions can be inferred.

Structural similarity can be identified in three steps: 1) Collecting and processing drug structures: Information on the structures of the compounds in DrugBank is retrieved along with the SMILE code (a chemical notation representing a chemical structure in linear textual form). 2) Structural representation: BIT_MACCS (MACCS Structural Keys Bit packed) fingerprints are calculated for all molecules included in the study and each molecule is represented as a bit vector that codes the presence or absence of structural features where each feature is assigned a specific bit position. 3) Similarity measures, computation, and data representation: Different measures are used to compare similarity between two molecular fingerprints. In one embodiment, the molecular fingerprints were compared using Tanimoto coefficient (TC). The TC can span values between 0 and 1, where 0 means 'maximum dissimilarity' and 1 means 'maximum similarity.' The TC between two fingerprint representations A and B is defined as the number of features present in the intersection of both fingerprints A and B divided by the number of features present in the union of both fingerprints. Next, for each drug affected by a particular gene, the process predicts new gene based DDIs. One embodiment predicts new DDIs reduces to matrix multiplication of the matrices M1, which consists of the established interactions, and M2, which consists of the similarity matrix.

The pharmacogenomic information can be applied to drug labeling. One embodiment may contain information on genomic biomarkers and can describe:

Drug exposure and clinical response variability
Risk for adverse events
Genotype-specific dosing
Mechanisms of drug action
Polymorphic drug target and disposition genes The information may include specific actions to be taken based on the biomarker information. Pharmacogenomic information can appear in different sections of the labeling depending on the actions. Biomarkers in the table include but are not limited to germ-line or somatic gene variants, functional deficiencies, expression changes, and chromosomal abnormalities; selected protein biomarkers that are used to select patients for treatment are also included.

In one embodiment, the process includes constructing a gene-drug interactions training dataset that includes pharmaceutical, pharmacokinetic or pharmacodynamics, and pharmacogenomics drug-drug interactions for each drug; constructing side effect features for each of the plurality of drugs from side effects associated with the plurality of drugs; running a gene-drug-drug interactions classifier that predicts adverse drug-drug interactions for drug pairs and the genetic scan; and for each of the side effects, performing a Fisher's exact test to determine predicted gene-drug-drug interactions. Fisher's exact testis a statistical significance test used in the analysis of contingency tables. It is one of a class of exact tests, so called because the significance of the deviation from a null hypothesis (e.g., P-value) can be calculated exactly, rather than relying on an approximation that becomes exact in the limit as the sample size grows to infinity, as with many statistical tests.

FIG. 13E shows a deep learning machine using deep convolutionary neural networks for detecting genetic based drug-drug interaction. One embodiment uses an AlexNet: 8-layer architecture, while another embodiment uses a VGGNet: 16-layer architecture (each pooling layer and last 2 FC layers are applied as feature vector). For drugs, the indications of use and other drugs used capture most of many important covariates. One embodiment access data from SIDER (a text-mined database of drug package inserts), the Offsides database that contains information complementary to that found in SIDER and improves the prediction of protein targets and drug indications, and the Twosides database of mined putative DDIs also lists predicted adverse events, all available at the http://PharmGKB.org Web site.

The system of FIG. 13E receives data on adverse events strongly associated with indications for which the indication and the adverse event have a known causative relationship. A drug-event association is synthetic if it has a tight reporting correlation with the indication ($\rho \geq 0.1$) and a high relative reporting (RR) association score (RR$\geq$2). Drugs reported frequently with these indications were 80.0 (95% CI, 14.2 to 3132.8; P<0.0001, Fisher's exact test) times as likely to have synthetic associations with indication events. Disease indications are a significant source of synthetic associations. The more disproportionately a drug is reported with an indication (x axis), the more likely that drug will be synthetically associated. For example, adverse events strongly associated with drugs are retrieved from the drug's package insert. These drug-event pairs represent a set of known strong positive associations.

Adverse events related to sex and race are also analyzed. For example, for physiological reasons, certain events predominantly occur in males (for example, penile swelling and azoospermia). Drugs that are disproportionately reported as causing adverse events in males were more likely to be synthetically associated with these events. Similarly, adverse events that predominantly occur in either relatively young or relatively old patients are analyzed.

"Off-label" adverse event data is also analyzed, and off-label uses refer to any drug effect not already listed on the drug's package insert. For example, the SIDER database, extracted from drug package inserts, lists 48,577 drug-event associations for 620 drugs and 1092 adverse events that are also covered by the data mining. Offsides recovers 38.8% (18,842 drug-event associations) of SIDER associations from the adverse event reports. Thus, Offsides finds different associations from those reported during clinical trials before drug approval.

Polypharmacy side effects for pairs of drugs (Twosides) are also analyzed. These associations are limited to only those that cannot be clearly attributed to either drug alone (that is, those associations covered in Offsides). The database contains an significant associations for which the drug pair has a higher side-effect association score, determined using the proportional reporting ratio (PRR), than those of the individual drugs alone. The system determines pairwise similarity metrics between all drugs in the Offsides and SIDER databases. The system can predict shared protein targets using drug-effect similarities. The side-effect similarity score between two drugs is linearly related to the number of targets that those drugs share.

The system can determine relationships between the proportion of shared indications between a pair of drugs and the similarity of their side-effect profiles in Offsides. The system can use side-effect profiles to suggest new uses for old drugs. While the preferred system predicts existing therapeutic indications of known drugs, the system can recommend drug repurposing using drug-effect similarities in Offsides.

Corroboration of class-wide interaction effects with EMRs. The system can identify DDIs shared by an entire drug class. The class-class interaction analysis generates putative drug class interactions. The system analyzes laboratory reports commonly recorded in EMRs that may be used as markers of these class-specific DDIs.

The system can be used systematic drug surveillance. The FDA manages a collection of adverse drug event reports to monitor the safety of drugs. They rely on physicians, pharmaceutical companies, and patients to volunteer these reports. Since reporting is not mandatory, many adverse drug events that occur are never reported to the FDA. To address this issue, an embodiment of the present invention uses an algorithm to infer unreported adverse drug events. This embodiment relies on the fact that many adverse events occur together. For example, nausea and vomiting commonly manifest together. Therefore, if a drug is observed to causes nausea, it can be inferred that it also causes vomiting.

The successful prediction of side effects before a drug enters clinical trials can be done. Chemical informatics techniques can predict drug side effects by comparing the structural similarity of drugs. Protein structural similarity is learned by the deep learning system to predict drug side effects. More recently, network and chemical properties are used for predictive models of drug effects and leverage the system's comprehensive database of known drug effects.

In a parallel trend, anti-biotics and cancer treatments have lost their effect over time. As such, even though there is no adverse event, there is still a negative consequence for the patient when the virus/tumor develops resistance to the drug. Thus, the processor can analyze evolutions in the target of the treatment and recommend alternative treatment.

In one aspect, systems and methods includes analyzing a disease state of a subject by collecting genetic profile data on a population of tumors and original tumor treatment(s); identifying one or more evolutionary paths of escape and evolved tumor treatment(s); and based on a subject profile, predicting a probability of escape along the one or more evolutionary paths.

In another aspect, a method for analyzing a disease state of a subject includes capturing a first liquid biopsy from the subject; providing the liquid biopsy to a genetic analyzer to identify the subject's genetic information of a first disease state at a first time point; searching for genetically similar patients and predicting a mutation of the disease into a second disease state at a second time point; analyzing a treatment database and recommending a treatment given the first and second disease states; capturing a second liquid biopsy from the subject at a second time point; providing the second liquid biopsy to the genetic analyzer to identify the subject's genetic information; and if the genetic information from the second time point matches the predicted mutation, continuing the recommended treatment for the subject and otherwise changing the recommended treatment.

In yet another aspect, a method to detect abnormal cellular activities includes sequencing of cell-free nucleic acid with a genetic analyzer or a DNA sequencer; comparing current sequence reads with prior sequence reads from at least two time points; detecting a mutation of the cell-free nucleic acid and updating a diagnostic confidence indication accordingly; and detecting the presence or absence of genetic alteration and/or amount of genetic variation in an individual based on the diagnostic confidence indication of the sequence read.

In a further aspect, a method for analyzing a disease state of a subject includes capturing a first liquid biopsy from the subject; providing the liquid biopsy to a genetic analyzer to identify the subject's genetic information of a first disease state at a first time point; searching for genetically similar subject profiles and predicting a mutation of the disease into a second disease state at a second time point; capturing a second liquid biopsy from the subject; providing the second liquid biopsy to a genetic analyzer to identify the subject's genetic information at a second time point; and if the genetic information from the second time point matches the predicted mutation, continuing the recommended treatment for the subject and otherwise changing the recommended treatment.

In another aspect disclosed herein is a method for analyzing a disease state of a subject by characterizing the subject's genetic information at two or more time points with a genetic analyzer, e.g., a DNA sequencer; and using the information from the two or more time points to produce an adjusted test result in the characterization of the subject's genetic information.

In another aspect, a method detects a trend in the amount of mutation cancer polynucleotides in a sample from a subject over time by determining a frequency of the cancer polynucleotides at a plurality of time points; determining an error range for the frequency at each of the plurality of time points; determining, between an earlier and later time point, whether error ranges (1) overlap, indicating stability of frequency, (2) an increase at the later time point outside the error range, indicating increase in frequency or (3) a decrease at the later time point outside the error range, indicating decrease in frequency.

In yet another aspect, a method detects mutation cellular activities by sequencing of cell-free nucleic acid with a genetic analyzer, e.g., a DNA sequencer; comparing later (e.g., current) sequence reads with prior sequence reads from at least two time points and updating a diagnostic confidence indication accordingly; and detecting the presence or absence of genetic alteration and/or amount of genetic variation in an individual based on the diagnostic confidence indication of the sequence read. A genetic analyzer includes any system for genetic analysis, e.g., by sequencing (DNA sequencer) or hybridization (microarray, fluorescent in situ hybridization, bionanogenomics) or other.

In another aspect, a method detects a mutation in a cell-free or substantially cell free sample obtained from a subject by generating consensus sequences by comparing later (e.g., current) sequence reads by a genetic analyzer, e.g., a DNA sequencer, with prior sequence reads from a prior period and updating a diagnostic confidence indication based on the prior sequence reads, each consensus sequence corresponding to a unique polynucleotide among a set of tagged parent polynucleotides, and generating a genetic profile of extracellular polynucleotides in the subject, wherein the genetic profile comprises a plurality of data resulting from copy number variation or mutation analyses.

In another aspect disclosed herein is a method to detect mutation cellular activities by providing at least one set of tagged parent polynucleotides, and for each set of tagged parent polynucleotides; amplifying the tagged parent polynucleotides in the set to produce a corresponding set of amplified progeny polynucleotides; with a genetic analyzer, e.g., a DNA sequencer, sequencing a subset of the set of amplified progeny polynucleotides, to produce a set of sequencing reads; and collapsing the set of sequencing reads to generate a set of consensus sequences by comparing current sequence reads with prior sequence reads from at least one prior period and updating diagnostic confidence indication accordingly, each consensus sequence corresponding to a unique polynucleotide among the set of tagged parent polynucleotides.

In yet another aspect, a method detects a mutation in a cell-free or substantially cell free sample obtained from a subject by sequencing extracellular polynucleotides from a bodily sample from a subject with a genetic analyzer, e.g., a DNA sequencer; for each of the extracellular polynucleotide, generating a plurality of sequencing reads; filtering out reads that fail to meet a set threshold; mapping sequence reads derived from the sequencing onto a reference sequence; identifying a subset of mapped sequence reads that align with a variant of the reference sequence at each mappable base position; for each mappable base position, calculating a ratio of (a) a number of mapped sequence reads that include a variant as compared to the reference sequence, to (b) a number of total sequence reads for each mappable base position; and comparing current sequence reads with prior sequence reads from at least on other time point and updating a diagnostic confidence indication accordingly.

Figure 14A:
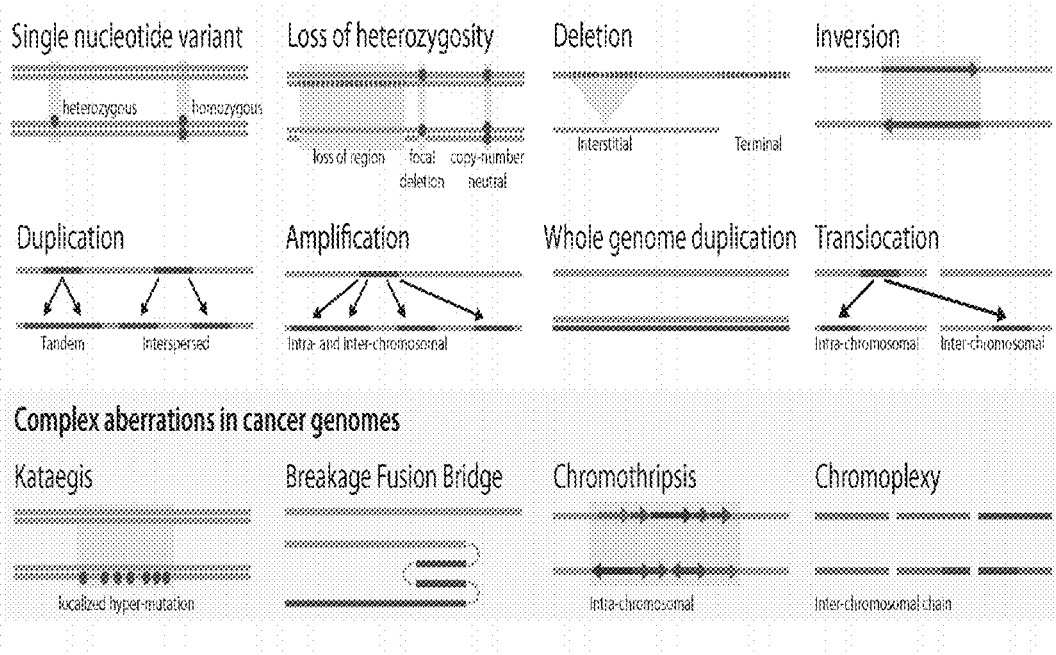
FIG. 14A shows various common aberrations in cancer genomes.
Figure 14B:
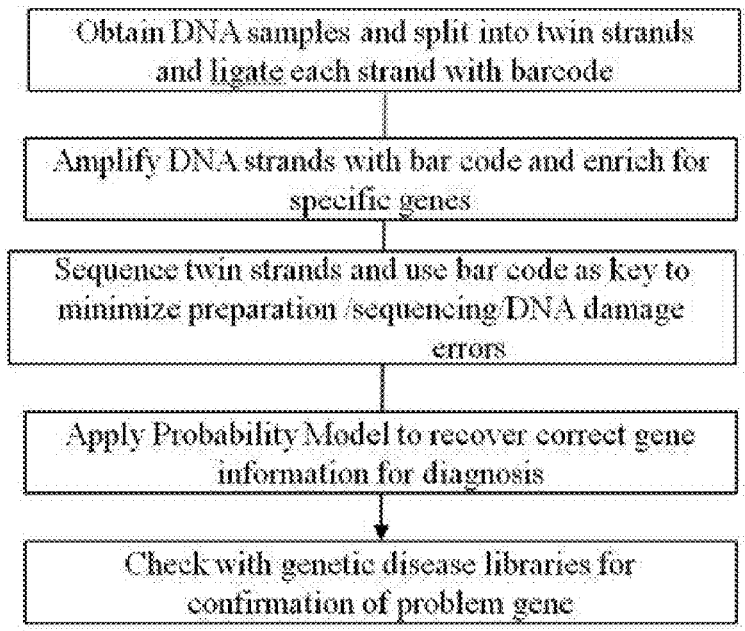
FIG. 14B shows an exemplary system to detect the evolutionary paths of escape.

The method identifies one or more evolutionary paths of escape and evolved tumor treatment(s). These paths are caused by various drivers. For example, as shown in FIG. 14A, common aberrations in cancer genomes can lead to the abnormal chromosome numbers (aneuploidy) and chromosome structures of a cancer genome. In FIG. 14A, lines indicate the genome with germline genome on top and cancer genome with somatic aberrations below. Double lines are used when differentiating heterozygous and homozygous changes is useful. Dots represent single nucleotide changes, whereas lines and arrows represent structural changes. FIG. 14B shows an exemplary system to detect correct gene information for use in evolutionary paths of escape analysis, among others. Mutations and genetic alterations including in copy number, for example, allelic imbalances, chromosomal copy number changes, such as amplifications, deletions, aneuploidy, loss of heterozygosity, and micro-satellite instability are often found to be associated with a disease state, for example, cancer. It has been observed that alterations in chromosomal copy number and loss of heterozygosity (LOH) are forms of genetic changes that often signal the activation of oncogenes and inactivation of tumor suppressor genes (anti-oncogenes). Variations in the form of copy number polymorphisms (CNP) can also occur in normal individuals. Identification of the loci implicated in these aberrations can generate anchor points which facilitate oncogenomics and toxicogenomics studies. Subsequently the shared LOH and aberrant CN regions can be used to partition the transcriptome data and track the differential transcript expression in the affected genomic segments. Locating and exploring such alteration events is an important research approach toward understanding the cause and progression of disease. For diploid organisms, the abnormal chromosomal state results when the normal diploid distribution is perturbed, resulting in changes that can include, for example, deletions, amplifications and translocations. Deletions can be of a partial chromosome ranging from micro-deletions on the order of several kb to macro-deletions of mega bases, entire arms of a chromosome or entire chromosomes. Amplifications can range from partial chromosomal amplifications to gains of a single copy of a chromosome to multiple copy gains of one or more chromosomes. Translocations generally comprise parts of a first chromosome being translocated to another chromosome.

FIG. 14B shows the general architecture of an instantiated HMM for mutation detection. Each oval shape X1, X2, X3 represents a random variable that can adopt any of a number of values. The random variable x(t) is the hidden state at time t ($x(t) \in \{x1, x2, x3\}$). The random variable y(t) is the observation at time t (with $y(t) \in \{y1, y2, y3, y4\}$). The arrows in the diagram (often called a trellis diagram) denote conditional dependencies. The conditional probability distribution of the hidden variable x(t) at time t, given the values of the hidden variable x at all times, depends only on the value of the hidden variable x(t−1): the values at time t−2 and before have no influence. This is called the Markov property. Similarly, the value of the observed variable y(t) representing the mutation conditions only depends on the value of the hidden variable x(t) (both at time t).

In FIG. 14B, the state space of the hidden variables is discrete, while the observations themselves can either be discrete (typically generated from a categorical distribution) or continuous (typically from a Gaussian distribution). The parameters of a hidden Markov model are of two types, transition probabilities and emission probabilities (also known as output probabilities). The transition probabilities control the way the hidden state at time is chosen given the hidden state at time. The hidden state space is assumed to consist of one of possible values, modeled as a categorical distribution. (See the section below on extensions for other possibilities.) This means that for each of the possible states that a hidden variable at time can be in, there is a transition probability from this state to each of the possible states of the hidden variable at time, for a total of transition probabilities. Note that the set of transition probabilities for transitions from any given state must sum to 1. Thus, the matrix of transition probabilities is a Markov matrix. Because any one transition probability can be determined once the others are known, there are a total of transition parameters.

In addition, for each of the possible states, there is a set of emission probabilities governing the distribution of the observed variable at a particular time given the state of the hidden variable at that time. The size of this set depends on the nature of the observed variable. For example, if the observed variable is discrete with possible values, governed by a categorical distribution, there will be separate parameters, for a total of emission parameters over all hidden states. On the other hand, if the observed variable is an -dimensional vector distributed according to an arbitrary multivariate Gaussian distribution, there will be parameters controlling the means and parameters controlling the covariance matrix, for a total of emission parameters. (In such a case, unless the value of is small, it may be more practical to restrict the nature of the covariances between individual elements of the observation vector, e.g. by assuming that the elements are independent of each other, or less restrictively, are independent of all but a fixed number of adjacent elements.). The HMM method can model a somatic evolution of cancer. The method includes modeling genetic instability, which results in abnormal numbers of chromosomes or aneuploidy, elevated mutation rates, and altered distributions of mutational patterns.

The method can identify one or more cancer mutation drivers. These drivers include those that disrupt cellular signaling pathways essential for multicellular organisms and possible mutations that increase somatic fitness of cancer cells. The method can include identifying dynamics of tumor progression in a population based on interactions with an environment. The method includes collecting repeated genetic observations to enhance statistical inference about the evolution of tumors.

The method includes recommending or providing a therapeutic regimen in anticipation of the one or more escape paths. Diagnosis of cancer can be done by analyzing the genetic variants, even in the presence of noise. The analysis can be based on the frequency of Sequence Variants or Level of CNV and a diagnosis confidence indication or level for detecting genetic variants in the noise range can be established. The process increases the diagnosis confidence using a plurality of measurements to increase confidence of Diagnosis (6), or alternatively using measurements at a plurality of time points to determine whether cancer is advancing, in remission or stabilized. The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden." Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

In one implementation, using measurements from a plurality of samples collected substantially at once or over a plurality of time points, the diagnostic confidence indication for each variant can be adjusted to indicate a confidence of predicting the observation of the CNV or mutation. The confidence can be increased by using measurements at a plurality of time points to determine whether cancer is advancing, in remission or stabilized. The diagnostic confidence indication can be assigned by any of a number of known statistical methods is assigned and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two time points can be separated by about a month to about a year, about a year to about 5 years, or no more than about three months.

The HMM detect with high sensitivity genetic variation in a sample of initial genetic material. The methods involve using one to three of the following tools: First, the efficient conversion of individual polynucleotides in a sample of initial genetic material into sequence-ready tagged parent polynucleotides, so as to increase the probability that individual polynucleotides in a sample of initial genetic material will be represented in a sequence-ready sample. This can produce sequence information about more polynucleotides in the initial sample. Second, high yield generation of consensus sequences for tagged parent polynucleotides by high rate sampling of progeny polynucleotides amplified from the tagged parent polynucleotides, and collapsing of generated sequence reads into consensus sequences representing sequences of parent tagged polynucleotides. This can reduce noise introduced by amplification bias and/or sequencing errors, and can increase sensitivity of detection. Third, the noise in the detection of mutations and copy number variations is reduced by comparing prior sample analysis with the current sample and increasing a diagnostic confidence indication if the same mutations and copy number variations have appeared in prior analysis and otherwise decreasing the diagnostic confidence indication if this is the first time the sequence is observed.

Figure 14C:
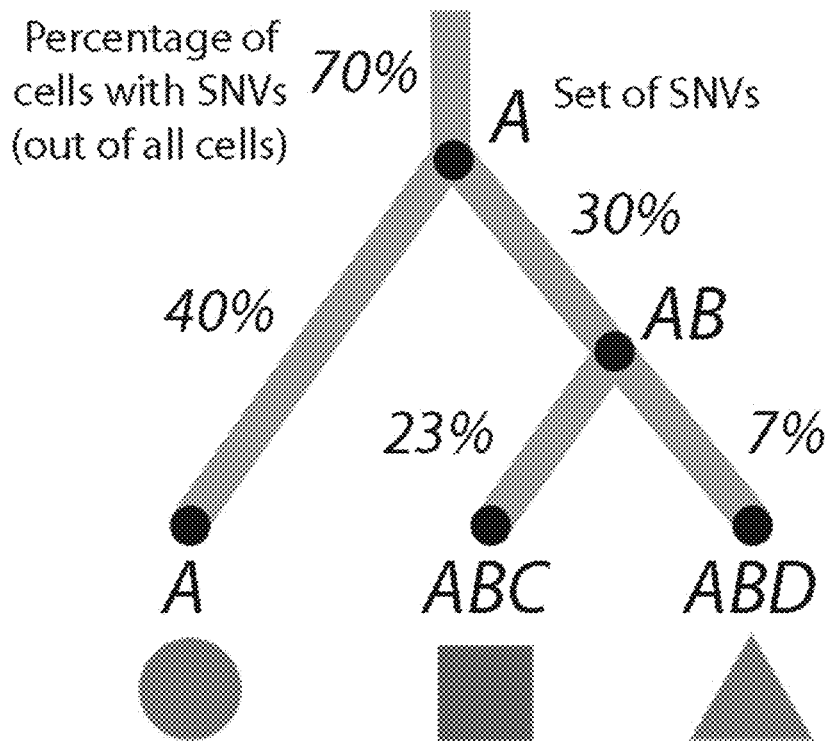
FIG. 14C shows an exemplary model generated by the system of FIG. 14B.

FIG. 14C shows an exemplary model generated b for inferring tumor phylogeny from next-generation sequencing data. The subclones are related to each other by an evolutionary process of acquisition of mutations. In this example, the three clones (leaf nodes) are characterized by different combinations of the four single nucleotide variant (SNV) sets A, B, C, and D. The percentages on the edges of the tree indicate the fraction of cells with this particular set of SNVs, e.g., 70% of all cells carry A, 40% additionally carry B, and only 7% carry A, B, and D.

Figure 14D:
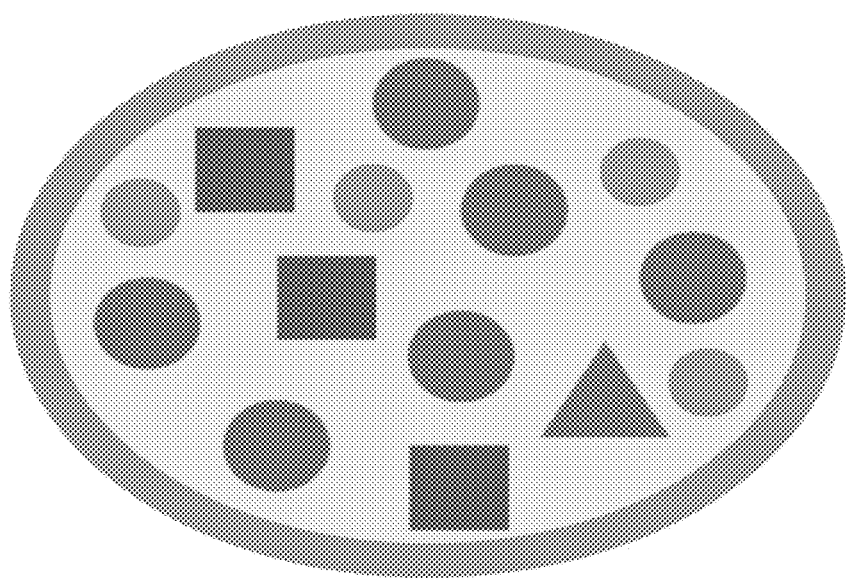
FIG. 14D shows an exemplary a heterogeneous collection of normal cells and cancer subclones developed during an evolutionary history of a tumor.

FIG. 14D shows an exemplary a heterogeneous collection of normal cells and cancer subclones developed during an evolutionary history of a tumor. The evolutionary history of a tumor gives rise to a heterogeneous collection of normal cells (small discs) and cancer subclones (large discs, triangles, squares). Internal nodes that have been fully replaced by their descendants (like the one carrying SNV sets A and B without C or D) are no longer part of the tumor.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

In one embodiment, the pattern recognizer may obtain a pattern definition in a simple format; predict several time steps in future by using Markov models; optimize results based on its predictions; detect transition between patterns; abstract data and extract information to infer higher levels of knowledge; combine higher and lower levels of information to understand about the patient and clinical behaviors; infer from multi-temporal (different time scales) data and associated information; using variable order Markov models, and/or reduce noise over time by employing clustering algorithms, such as k-means clustering.

For example, K vectors are randomly chosen and assigned as a cluster center for applying k-means clustering algorithms. In pattern recognition, the k-means is a method for classifying objects based on the closest training examples in the feature space. k-NN is a type of instance based learning, or lazy learning, where the function is only approximated locally and all computation is differed until classification. The Euclidian distance between different patterns in this vector space may be used to find clusters of patterns. The system may assign a new input vector to its closest cluster center and may move that cluster towards the input vector by a fraction of the Euclidean distance between them.

The system may use knowledge-based components such as a knowledge-based repository (KB). The repository may include clinical information. For example, it may include that "eating salt-rich food causes blood pressure to increase." The information may be stored in a variety of formats based on the type of inference employing them. The knowledge-based repository may act as a repository for some or all of the referenced knowledge. For example, it can include reference values for certain consents and variables used for inference. Accordingly, one or more layers (e.g. a hierarchical pattern processing layer or Pattern Engine) may subscribe to information from the knowledge-based repository. For example, one or more of the services may query the knowledge-based repository when making an inference.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'Asian male' and 'smartness', they may be connected using the relationship 'asian males are smart'. This relationship may be given a weight (e.g., 0.3). This relationship may vary from time to time (populations trend over years/decades). By leveraging the knowledge in the semantic web (e.g., all references and discussions on the web where 'asian male' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpora of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on patients with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

In one embodiment, the probability of a transition between two patterns may be used as the similarity between those patterns for the HC algorithm. The similarity metric may be used to cluster medical patterns that are likely to follow one another into the same cluster. The HC algorithm may be configured such that patterns that are unlikely to follow each other fall into different clusters. A cluster of a set of patterns that are likely to follow each other in time may be referred to as a temporal group. The HC algorithm may start with all store patterns and separate clusters and then recursively merge clusters with the greatest similarity. This may be used to obtain a treelike structure (e.g. a dendrogram) with a single cluster (which may contain all patterns) at the top of the tree and the individual patterns at the bottom (e.g. each pattern in its own cluster). The system may achieve the desired clustering for temporal grouping (e.g. somewhere between the bottom and a top of the dendrogram) by defining a suitable criteria. For example, one criterion could be to cut the tree at a level where the size of the largest cluster does not exceed a particular value. The node may have a design perimeter that sets the maximum number of clusters or temporal groups of the node. The desired temporal groups may be achieved by selecting a level of the dendrogram that gives the number of temporal groups closest to and less than the configured maximum number of temporal groups. These temporal groups may be updated as the Markov transition probabilities are updated. These steps may be performed periodically during the learning process. The learning process may be stopped once the temporal groups have sufficiently stabilized.

Once a node has completed its learning process, it may be used for sensing and/or inference. The characteristics of the input to the node in sensing may be identical to those used during learning. For example, objects may move under the field of view of the node and the node may see portions of those objects. The resulting patterns may be used as inputs to the node.

A node used for sensing and/or inference may produce an output for every input pattern. A node may also use a sequence of patents to produce an output. In one embodiment, it can be assumed that the outputs are produced based on instantaneous inputs. Under this assumption, the Markov graph may not be used during the sensing phase. For example, it may be discarded once the temporal groups within the node are completed.

For every input pattern, the node may produce an output factor that indicates the degree of membership of the input pattern and each of its temporal groups. However, the current input pattern may not perfectly match any of the patterns stored in memory. Accordingly, in one embodiment, the closeness of the input pattern to every pattern stored in memory will be determined. For example, let di be the distance of the ith(PLS CHECK?) stored pattern from the input pattern. The larger this distance is, the smaller the match between the input pattern and the stored pattern becomes. Assuming that the probability that an input pattern matches a stored pattern falls off as a Gaussian function of the Euclidean distance, the probability that the input pattern matches the ith(PLS CHECK?) stored pattern can be calculated as being proportional to $e-d2i/\alpha$, where $\alpha$ is a parameter of the node. Calculating this for every stored pattern may give the closeness of the current input pattern to all the vertices of the Markov graph.

Degree of membership of the input pattern in each temporal group may be determined by the maximum of its closeness to each of the vertices within the temporal group. This results in a length equal to the number of temporal groups, with each component of the factor indicating the degree of membership of the input pattern in the corresponding temporal group. This factor may then be used normalize the sum to unity. These normalized memberships may be used as estimates of probability of membership in each temporal group. This normalized degree of membership may also be used as an output of the node. The output may be a histogram giving estimates of probability of membership of the current input pattern and each of the temporal groups of the node.

As data is fed into the pattern recognizer, the transition probabilities for each pattern and pattern-of-patterns may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The pattern recognizer may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the (p+1)th occurrence. Then, the process may be repeated. This may be done until the pattern recognizer predicts logical relationships up to a specified accuracy threshold. Then, the results may be considered optimal.

When a node is at the first level of the hierarchy, its input may come directly from the data source, or after some preprocessing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

The system can use an expert system that can assess hypertension in according with the guidelines. In addition, the expert system can use diagnostic information and apply the following rules to assess hypertension:

Hemoglobin/hematocrit: Assesses relationship of cells to fluid volume (viscosity) and may indicate risk factors such as hypercoagulability, anemia.

Blood urea nitrogen (BUN)/creatinine: Provides information about renal perfusion/function.

Glucose: Hyperglycemia (diabetes mellitus is a precipitator of hypertension) may result from elevated catecholamine levels (increases hypertension).

Serum potassium: Hypokalemia may indicate the presence of primary aldosteronism (cause) or be a side effect of diuretic-therapy.

Serum calcium: Imbalance may contribute to hypertension.

Lipid panel (total lipids, high-density lipoprotein [HDL], low-density lipoprotein [LDL], cholesterol, triglycerides, phospholipids): Elevated level may indicate predisposition for/presence of atheromatous plaques.

Thyroid studies: Hyperthyroidism may lead or contribute to vasoconstriction and hypertension.

Serum/urine aldosterone level: May be done to assess for primary aldosteronism (cause).

Urinalysis: May show blood, protein, or white blood cells; or glucose suggests renal dysfunction and/or presence of diabetes.

Creatinine clearance: May be reduced, reflecting renal damage.

Urine vanillylmandelic acid (VMA) (catecholamine metabolite): Elevation may indicate presence of pheochromocytoma (cause); 24-hour urine VMA may be done for assessment of pheochromocytoma if hypertension is intermittent.

Uric acid: Hyperuricemia has been implicated as a risk factor for the development of hypertension.

Renin: Elevated in renovascular and malignant hypertension, salt-wasting disorders.

Urine steroids: Elevation may indicate hyperadrenalism, pheochromocytoma, pituitary dysfunction, Cushing's syndrome.

Intravenous pyelogram (IVP): May identify cause of secondary hypertension, e.g., renal parenchymal disease, renal/ureteral-calculi.

Kidney and renography nuclear scan: Evaluates renal status (TOD).

Excretory urography: May reveal renal atrophy, indicating chronic renal disease.

Chest x-ray: May demonstrate obstructing calcification in valve areas; deposits in and/or notching of aorta; cardiac enlargement.

Computed tomography (CT) scan: Assesses for cerebral tumor, CVA, or encephalopathy or to rule out pheochromocytoma.

Electrocardiogram (ECG): May demonstrate enlarged heart, strain patterns, conduction disturbances. Note: Broad, notched P wave is one of the earliest signs of hypertensive heart disease.

The system may also be adaptive. In one embodiment, every level has a capability to obtain feedback information from higher levels. This feedback may inform about certain characteristics of information transmitted bottom-up through the network. Such a closed loop may be used to optimize each level's accuracy of inference as well as transmit more relevant information from the next instance.

The system may learn and correct its operational efficiency over time. This process is known as the maturity process of the system. The maturity process may include one or more of the following flow of steps:

a. Tracking patterns of input data and identifying predefined patterns (e.g. if the same pattern was observed several times earlier, the pattern would have already taken certain paths in the hierarchical node structure).

b. Scanning the possible data, other patterns (collectively called Input Sets (IS)) required for those paths. It also may check for any feedback that has come from higher levels of hierarchy. This feedback may be either positive or negative (e.g., the relevance of the information transmitted to the inferences at higher levels). Accordingly, the system may decide whether to send this pattern higher up the levels or not, and if so whether it should it send through a different path.

c. Checking for frequently required ISs and pick the top 'F' percentile of them.

d. Ensuring it keeps this data ready.

In one embodiment, information used at every node may act as agents reporting on the status of a hierarchical network. These agents are referred to as Information Entities (In En). In En may provide insight about the respective inference operation, the input, and the result which collectively is called knowledge.

This knowledge may be different from the KB. For example, the above described knowledge may include the dynamic creation of insights by the system based on its inference, whereas the KB may act as a reference for inference and/or analysis operations. The latter being an input to inference while the former is a product of inference. When this knowledge is subscribed to by a consumer (e.g.

administering system or another node in a different layer) it is called "Knowledge-as-a-Service (KaaS)"

One embodiment processes behavior models are classified into four categories as follows:
 a. Outcome-based;
 b. Behavior-based;
 c. Determinant-based; and
 d. Intervention-based.

One or more of the following rules of thumb may be applied during behavioral modeling:
 One or more interventions affect determinants;
 One or more determinants affect behavior; and
 One or more behaviors affect outcome.

A behavior is defined to be a characteristic of an individual or a group towards certain aspects of their life such as health, social interactions, etc. These characteristics are displayed as their attitude towards such aspects. In analytical terms, a behavior can be considered similar to a habit. Hence, a behavior may be observed POP™ for a given data from a user. An example of a behavior is dietary habits.

Determinants may include causal factors for behaviors. They either cause someone to exhibit the same behavior or cause behavior change. Certain determinants are quantitative but most are qualitative. Examples include one's perception about a food, their beliefs, their confidence levels, etc.

Interventions are actions that affect determinants. Indirectly they influence behaviors and hence outcomes. System may get both primary and secondary sources of data. Primary sources may be directly reported by the end-user and AU. Secondary data may be collected from sensors such as their mobile phones, cameras, microphone, as well as those collected from general sources such as the semantic web.

These data sources may inform the system about the respective interventions. For example, to influence a determinant called forgetfulness which relates to a behavior called medication, the system sends a reminder at an appropriate time, as the intervention. Then, feedback is obtained whether the user took the medication or not. This helps the system in confirming if the intervention was effective.

The system may track a user's interactions and request feedback about their experience through assessments. The system may use this information as part of behavioral modeling to determine if the user interface and the content delivery mechanism have a significant effect on behavior change with the user. The system may use this information to optimize its user interface to make it more personalized over time to best suit the users, as well as to best suit the desired outcome.

The system also may accommodate data obtained directly from the end-user, such as assessments, surveys, etc. This enables users to share their views on interventions, their effectiveness, possible causes, etc. The system's understanding of the same aspects is obtained by way of analysis and service by the pattern recognizer.

Both system-perceived and end user-perceived measures of behavioral factors may be used in a process called Perception Scoring (PS). In this process, hybrid scores may be designed to accommodate both above mentioned aspects of behavioral factors. Belief is the measure of confidence the system has, when communicating or inferring on information. Initially higher beliefs may be set for user-perceived measures.

Over time, as the system finds increasing patterns as well as obtains feedback in pattern recognizer, the system may evaluate the effectiveness of intervention(s). If the system triggers an intervention based on user-perceived measures and it doesn't have significant effect on the behavior change, the system may then start reducing its belief for user-perceived measures and instead will increase its belief for system-perceived ones. In other words, the system starts believing less in the user and starts believing more in itself. Eventually this reaches a stage where system can understand end-users and their behavioral health better than end-users themselves. When perception scoring is done for each intervention, it may result in a score called Intervention Effectiveness Score (IES).

Perception scoring may be done for both end-users as well as AU. Such scores may be included as part of behavior models during cause-effect analysis.

Causes may be mapped with interventions, determinants, and behavior respectively in order of the relevance. Mapping causes with interventions helps in back-tracking the respective AU for that cause. In simple terms, it may help in identifying whose actions have had a pronounced effect on the end-user's outcome, by how much and using which intervention. This is very useful in identifying AUs who are very effective with specific interventions as well as during certain event context. Accordingly, they may be provided a score called Associated User Influence Score. This encompasses information for a given end-user, considering all interventions and possible contexts relevant to the user's case.

The system may construct one or plans including one or more interventions based on analysis performed, and may be implemented. For example, the system may analyze eligibility of an intervention for a given scenario, evaluating eligibility of two or more interventions based on combinatorial effect, prioritizing interventions to be applied, based on occurrence of patterns (from pattern recognizer), and/or submitting an intervention plan to the user or doctor in a format readily usable for execution.

This system may rely on the cause-effect analysis for its planning operations. A plan consists of interventions and a respective implementation schedule. Every plan may have several versions based on the users involved in it. For example, the system may have a separate version for the physician as compared to a patient. They will in turn do the task and report back to the system. This can be done either directly or the system may indirectly find it based on whether a desired outcome with the end user was observed or not.

The methodology may be predefined by an analyst. For every cause, which can be an intervention(s), determinant(s), behavior(s) or combinations of the same, the analyst may specify one or more remedial actions. This may be specified from the causal perspective and not the contextual perspective.

This approach uses the idea of situation-aware metadata description framework meaning that context specific information for all possible contexts specified in the meta data during system design. This process may be done for every cause, thereby specifying what remedial actions are more appropriate for it and for what context.

Accordingly, a set of remedial actions may be confirmed by determining which users should participate in the intervention plan and how. For example, if a physician had a high score for improving confidence of a patient, the intervention plan may consider that fact and include one of the interventions to be motivational interviewing of the patient by that physician, provided the cause-effect analysis confirms it with a closely associated cause.

The system may optimize its plan to ensure that it reflects a smooth transition between plans (current versus new) and hence interventions to the end user. The rules for such optimizations may be manually specified by the analyst during the design.

The system may include selecting appropriate presentation mode (e.g. web or mobile) as well as device (e.g. phone or tablet) based on the intervention specified, mapping rules to each intervention based on plan, operating both proactively (based on predefined plan) and reactively (feedback-based inference engine), obtaining feedback about the end-user from system usage and self-reporting, facilitating data to the pattern recognizer and hence made the overall end-to-end system a reflexive feedback system, and/or calling the pattern recognizer on-demand. In the use case, the patient may be presented with articles related to the consumption of carbohydrates, given one or more carbohydrate-counting goals, and/or receive one or more notifications to perform a task, such as instructions to reduce salt in the diet, pick up medication or exercise.

There may be a communication component within every presentation channel that accepts its version of the plan through a secured communication protocol. There may also be an execution component within every presentation layer that will take care of starting the new plan at a calculated period before the completion of the current plan. This ensures that the transition between plans is smooth enough for the users to not experience a drastic change in interventions. Also, the execution component may also suppress certain flows of delivering content in the inference engine based on the new plan. This ensures that the users are not sent contents from two plans which may look confusing. Considering the context, either the new plan or the current plan may be preferred over the other. This component also may manage between both plans simultaneously, if necessary.

Every presentation channel may be associated with a presentation device. The capabilities and various sensory data input options of the device may be used by inference engine. The device-specific version of the plan is meant to address this issue. In certain cases, such as mobile phones, handheld devices, etc., where camera and microphone is available, a specific pattern recognition engine takes specific samples of pictorial, video and auditory data, using camera and microphone, and then compare it with predefined categories of emotions. Hence, it may perform a pattern classification operation. The engine may be pre-trained with example data in these formats for those respective categories. The pattern recognition mechanism may be similar to the one performed by pattern recognizer. But in this engine, the focus may be on only sensory inputs and basic classification. Thus, it may not have any hierarchical layers of computation making it much simpler and more specific. After classification, it may compare the classification between the three sensory data sources and confirm the emotional state of the end user using suitable algorithms. This feature becomes a valuable source of information that may be used by different services for making psychological and behavioral inferences.

Accordingly, the system may send a variety of data and information to pattern recognizer and other services, as feedback, for these services to understand about the users. This understanding may affect their next set of plans which in turn becomes an infinite cyclic system where system affects the users while getting affected by them at the same time. Such a system is called a reflexive-feedback enabled system. The system may user both positive and negative reflexive-feedback, though the negative feedback aspect may predominantly be used for identifying gaps that the system needs to address.

The system may provide information, such as one or more newly identified patterns, to an analyst (e.g., clinical analyst or doctor). In the use case, the doctor may be presented with one or more notifications to address the relationship between carbohydrates and the medication that the patient is taking.

One embodiment of the system operation includes receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information.

Hypertension metrics may be one type of metrics utilized within the principles of the present disclosure. A hypertension score can be based on any type of alpha-numeric or visual analog scale. Hypertension scales may or may not be clinically validated and may use any scale (e.g. 1-100, 1-10, 1-4), picture, symbol, color, character, number, sound, letter, or written description of hypertension to facilitate the communication of a patient's hypertension level. The type of hypertension scale used may be determined according to a patient's and/or healthcare provider's preferences, and may also be determined based on the needs of a patient including, for example, the patient's age and/or communication capability. In further embodiments, the selected hypertension scale(s) may be determined by a service provider, such as, e.g., an organization implementing the principles of the present disclosure via a suitable software program or application.

Another metric may include a functionality score. A functionality score can be based on any type of alpha-numeric or visual analog scale. Non-limiting examples include the American Chronic Pain Association Quality of Life (ACPA QoL) Scale, Global Assessment of Functioning (GAF) Scale, and Short Form SF-36 Health Survey. Functionality scales may or may not be clinically validated and may use any picture, symbol, color, character, number, sound, letter, written description of quality of life, or physical functioning to facilitate communication of a patient's functionality level. The functionality score may be, e.g., based on an assessment of a patient's ability to exercise as well as perform daily tasks and/or perform routine tasks such as, e.g., getting dressed, grocery shopping, cooking, cleaning, climbing stairs, etc. In some embodiments, the selected functionality scale(s) may be determined by a service provider, such as, e.g., an organization implementing the principles of the present disclosure via a suitable software program or application.

A further metric may include a patient's medication usage. Medication use encompasses pharmacologic and therapeutic agents used to treat, control, and/or alleviate hypertension, including prescription drugs as well as over-the-counter medications, therapeutic agents, and other non-prescription agents. Medication use may include different classes of pharmacologic agents. Medication use can be reported in any appropriate units, such as number of doses taken, percentage of treatment plan completed, frequency of doses, and/or dose strength; and may also specify additional information such as the type of formulation taken and the route of administration (oral, enteral, topical, transdermal, parenteral, sublingual etc.). Molecular alternatives (e.g., acid, salt, solvate, complex, and pro-drug forms, etc.) and formulations (e.g., solid, liquid, powder, gel, and suspensions, etc.) are further contemplated. Reported medication use may, for example, include the number of doses and types of medication taken since a previous reported medication use, and may also indicate the number of closes and types of medication taken within a period of time, such as within, the previous 2 hours, 4 hours, 6 hours, 12 hours, 18 hours, 24 hours, 36 hours, or 48 hours. In some embodiments, for example, medication use may be reported in terms of dosage units recommended by a manufacturer or healthcare provider for a given medication (e.g., minimum, maximum, or range of appropriate unit dosage per unit time).

Reported medication use may allow for tracking compliance with a treatment regime. For example, a record of reported medication use may assist a healthcare provider in evaluating medication efficacy, adjusting dosage, and/or adding other medications as necessary.

In some embodiments of the present disclosure, a patient or healthcare provider may create a patient profile comprising, e.g., identifying, characterizing, and/or medical information, including information about a patient's medical history, profession, and/or lifestyle. Further examples of information that may be stored in a patient profile includes diagnostic information such as family medical history, medical symptoms, duration of hypertension, localized vs. general hypertension, etc. Further contemplated as part of a patient profile are non-pharmacologic treatment(s) (e.g., chiropractic, radiation, holistic, psychological, acupuncture, etc.), lifestyle characteristics (e.g., diet, alcohol intake, smoking habits), cognitive condition, behavioral health, and social well-being.

A patient profile may, for example, be stored in a database and accessible for analysis of the patient's reported hypertension metrics. In some embodiments, a patient profile may be created before collecting and/or transmitting a set of hypertension metrics to be received by a server and/or database In other embodiments, a patient profile may be created concurrently with, or even after transmitting/receiving one or more hypertension metrics. In some embodiments a patient profile may be used to establish one or more hypertension metric e and/or reference values. A patient profile may, for example, allow for setting threshold values or ranges, wherein reported hypertension metrics that fall outside of those limits trigger an alert to be sent to the patient or a healthcare provider. Threshold values, limits, or ranges may also be set without reference to a patient profile. In some embodiments, one or more target value(s) (e.g., hypertension metric value(s)) may be set to determine how the reported hypertension metrics compare with the target value(s).

The methods and systems disclosed herein may rely on one or more algorithm(s) to analyze one or more of the described metrics. The algorithm(s) may comprise analysis of data reported in real-time, and may also analyze data reported in real-time in conjunction with auxiliary data stored in a hypertension management database. Such auxiliary data may comprise, for example, historical patient data such as previously-reported hypertension metrics (e.g., hypertension scores, functionality scores, medication use), personal medical history, and/or family medical history. In some embodiments, for example, the auxiliary data includes at least one set of hypertension metrics previously reported and stored for a patient. In some embodiments, the auxiliary data includes a patient profile such as, e.g., the patient profile described above. Auxiliary data may also include statistical data, such as hypertension metrics pooled for a plurality of patients within a similar group or subgroup. Further, auxiliary data may include clinical guidelines such as guidelines relating to hypertension management, including evidence-based clinical practice guidelines on the management of acute and/or chronic hypertension or other chronic conditions.

Analysis of a set of hypertension metrics according to the present disclosure may allow for calibration of the level, degree, and/or quality of hypertension experienced by providing greater context to patient-reported data. For example, associating a hypertension score of 7 out of 10 with high functionality for a first patient, and the same score with low functionality for a second patient may indicate a relatively greater debilitating effect of hypertension on the second patient than the first patient. Further, a high hypertension score reported by a patient taking a particular medication such as opioid analgesics may indicate a need to adjust the patient's treatment plan. Further, the methods and systems disclosed herein may provide a means of assessing relative changes in a patient's distress due to hypertension over time. For example, a hypertension score of 5 out of 10 for a patient who previously reported consistently lower hypertension scores, e.g., 1 out of 10, may indicate a serious issue requiring immediate medical attention.

Any combination(s) of hypertension metrics may be used for analysis in the systems and methods disclosed. In some embodiments, for example, the set of hypertension metrics comprises at least one hypertension score and at least one functionality score. In other embodiments, the set of hypertension metrics may comprise at least one hypertension score, at least one functionality score, and medication use. More than one set of hypertension metrics may be reported and analyzed at a given time. For example, a first set of hypertension metrics recording a patient's current status and a second set of hypertension metrics recording the patient's status at an earlier time may both be analyzed and may also be used to generate one or more recommended actions.

Each hypertension metric may be given equal weight in the analysis, or may also be given greater or less weight than other hypertension metrics included in the analysis. For example, a functionality score may be given greater or less weight with respect to a hypertension score and/or medication use. Whether and/or how to weigh a given hypertension metric may be determined according to the characteristics or needs of a particular patient. As an example, Patient A reports a hypertension score of 8 (on a scale of 1 to 10 where 10 is the most severe hypertension) and a functionality score of 9 (on a scale of 1 to 10 where 10 is highest functioning), while Patient B reports a hypertension score of 8 but a functionality score of 4. The present disclosure provides for the collection, analysis, and reporting of this information, taking into account the differential impact of one hypertension score on a patient's functionality versus that same hypertension score's impact on the functionality of a different patient.

Hypertension metrics may undergo a pre-analysis before inclusion in a set of hypertension metrics and subsequent application of one or more algorithms. For example, a raw score may be converted or scaled according to one or more algorithm(s) developed for a particular patient. In some embodiments, for example, a non-numerical raw score may be converted to a numerical score or otherwise quantified prior to the application of one or more algorithms. Patients and healthcare providers may retain access to raw data (e.g., hypertension metric data prior to any analysis)

Algorithm(s) according, to the present disclosure may analyze the set of hypertension metrics according to any suitable methods known in the art. Analysis may comprise, for example, calculation of statistical averages, pattern recognition, application of mathematical models, factor analysis, correlation, and/or regression analysis. Examples of analyses that may be used herein include, but are not limited to, those disclosed in U.S. Patent Application Publication No. 2012/0246102 A1 the entirety of which is incorporated herein by reference.

The present disclosure further provides for the determination of an aggregated hypertension assessment score. In some embodiments, for example, a set of pairs metrics may be analyzed to generate a comprehensive and/or individualized assessment of hypertension by generating a composite or aggregated score. In such embodiments, the aggregated score may include a combination of at least one hypertension score, at least one functionality score, and medication use. Additional metrics may also be included in the aggregated score. Such metrics may include, but are not limited to, exercise habits, mental well-being, depression, cognitive functioning, medication side effects, etc. Any of the aforementioned types of analyses may be used in determining an aggregated score.

The algorithm(s) may include a software program that may be available for download to an input device in various versions. In some embodiments, for example, the algorithm(s) may be directly downloaded through the Internet or other suitable communications means to provide the capability to troubleshoot a health issue in real-time. The algorithm(s) may also be periodically updated, e.g., provided content changes, and may also be made available for download to an input device.

The methods presently disclosed may provide a healthcare provider with a more complete record of a patient's day-to-day status. By having access to a consistent data stream of hypertension metrics for a patient, a healthcare provider may be able to provide the patient with timely advice and real-time coaching on hypertension management options and solutions. A patient may, for example, seek and/or receive feedback on hypertension management without waiting for an upcoming appointment with a healthcare provider or scheduling a new appointment. Such real-time communication capability may be especially beneficial to provide patients with guidance and treatment options during intervals between appointments with a healthcare provider. Healthcare providers may also be able to monitor a patient's status between appointments to timely initiate, modify, or terminate a treatment plan as necessary. For example, a patient's reported medication use may convey whether the patient is taking too little or too much medication. In some embodiments, an alert may be triggered to notify the patient and/or a healthcare provider of the amount of medication taken, e.g., in comparison to a prescribed treatment plan. The healthcare provider could, for example, contact the patient to discuss the treatment plan. The methods disclosed herein may also provide a healthcare provider with a longitudinal review of how a patient responds to hypertension over time. For example, a healthcare provider may be able to determine whether a given treatment plan adequately addresses a patient's needs based on review of the patient's reported hypertension metrics and analysis thereof according to the present disclosure.

Analysis of patient data according to the methods presently disclosed may generate one or more recommended actions that may be transmitted and displayed on an output device. In some embodiments, the analysis recommends that a patient make no changes to his/her treatment plan or routine. In other embodiments, the analysis generates a recommendation that the patient seek further consultation with a healthcare provider and/or establish compliance with a prescribed treatment plan. In other embodiments, the analysis may encourage a patient to seek immediate medical attention. For example, the analysis may generate an alert to be transmitted to one or more output devices, e.g., a first output device belonging to the patient and a second output device belonging to a healthcare provider, indicating that the patient is in need of immediate medical treatment. In some embodiments, the analysis may not generate a recommended action. Other recommended actions consistent with the present disclosure may be contemplated and suitable according to the treatment plans, needs, and/or preferences for a given patient.

The present disclosure further provides a means for monitoring a patient's medication use to determine when his/her prescription will run out and require a refill. For example, a patient profile may be created that indicates a prescribed dosage and frequency of administration, as well as total number of dosages provided in a single prescription. As the patient reports medication use, those hypertension metrics may be transmitted to a server and stored in a database in connection with the patient profile. The patient profile stored on the database may thus continually update with each added metric and generate a notification to indicate when the prescription will run out based on the reported medication use. The notification may be transmitted and displayed on one or more output devices, e.g., to a patient and/or one or more healthcare providers. In some embodiments, the one or more healthcare providers may include a pharmacist. For example, a pharmacist may receive notification of the anticipated date a prescription will run out in order to ensure that the prescription may be timely refilled.

Patient data can be input for analysis according to the systems disclosed herein through any data-enabled device including, but not limited to, portable/mobile and stationary communication devices, and portable/mobile and stationary computing devices. Non-limiting examples of input devices suitable for the systems disclosed herein include smart phones, cell phones, laptop computers, netbooks, personal computers (PCs), tablet PCs, fax machines, personal digital assistants, and/or personal medical devices. The user interface of the input device may be web-based, such as a web page, or may also be a stand-alone application. Input devices may provide access to software applications via mobile and wireless platforms, and may also include web-based applications.

The input device may receive data by having a user, including, but not limited to, a patient, family member, friend, guardian, representative, healthcare provider, and/or caregiver, enter particular information via a user interface, such as by typing and/or speaking. In some embodiments, a server may send a request for particular information to be entered by the user via an input device. For example, an input device may prompt a user to enter sequentially a set of hypertension metrics, e.g., a hypertension score, a functionality score, and information regarding use of one or more medications (e.g., type of medication, dosage taken, time of day, route of administration, etc.). In other embodiments, the user may enter data into the input device without first receiving a prompt. For example, the user may initiate an application or web-based software program and select an option to enter one or more hypertension metrics. In some embodiments, one or more hypertension scales and/or functionality scales may be preselected by the application or software program. For example, a user may have the option of selecting the type of hypertension scale and/or functionality scale for reporting hypertension metrics within the application or software program. In other embodiments, an application or software program may not include preselected hypertension scales or functionality scales such that a user can employ any hypertension scale and/or functionality scale of choice.

The user interface of an input device may allow a user to associate hypertension metrics with a particular date and/or time of day. For example, a user may report one or more hypertension metrics to reflect a patient's present status. A user may also report one or more hypertension metrics to reflect a patient's status at an earlier time.

Patient data may be electronically transmitted from an input device over a wired or wireless medium to a server, e.g., a remote server. The server may provide access to a database for performing an analysis of the data transmitted, e.g., set of hypertension metrics. The database may comprise auxiliary data for use in the analysis as described above. In some embodiments, the analysis may be automated, and may also be capable of providing real-time feedback to patients and/or healthcare providers.

The analysis may generate one or more recommended actions, and may transmit the recommended action(s) over at wired or wireless medium for display on at least one output device. The at least one output device may include, e.g., portable/mobile and stationary communication devices, and portable/mobile and stationary computing devices. Non-limiting examples of output devices suitable for the systems disclosed herein include smart phones, cell phones, laptop computers, netbooks, personal computers (PCs), tablet PCs, fax machines, personal digital assistants, and/or personal medical devices. In some embodiments, the input device is the at least one output device. In other embodiments, the input device is one of multiple output devices. In some embodiments of the present disclosure, the one or more recommended actions are transmitted and displayed on each of two output devices. In such an example, one output device may belong to a patient and the other device may belong to a healthcare provider.

The present disclosure also contemplates methods and systems in a language suitable for communicating with the patient and/or healthcare provider, including languages other than English.

A patient's medical data may be subject to confidentiality regulations and protection. Transmitting, analyzing, and/or storing information according to the methods and systems disclosed herein may be accomplished through secure means, including HIPPA-compliant procedures and use of password-protected devices, servers, and databases.

One embodiment shares data with different health portals such as Apple's Healthkit, Samsung's Health database, and the US Government Blue Button, which is a nationally recognized symbol indicating to consumers that they can get their own health records electronically from doctors, hospitals, and other health care providers, such as pharmacies and health insurance plans. With electronic access to their health records, consumers can check them for accuracy and completeness, share them with people they trust—in case of emergency or to coordinate care among different providers—and reference them as needed. Health records may include clinical information from doctors and hospitals, health insurance claims, prescription histories, and lab/diagnostic test results. BlueButton.js parses and generates complex health data formats like C-CDA to allow the BP devices to empower patients with access to their health records. Blue-button software interface is detailed at https://github.com/blue-button/bluebutton.js, the content of which is incorporated by reference.

The systems and methods presently disclosed may be especially beneficial in outpatient, home, and/or on-the-go settings. The systems and methods disclosed herein may also be used as an inpatient tool and/or in controlled medication administration such as developing a personalized treatment plan.

In addition to monitoring health parameters, the system can include interventional devices such as a defibrillator. The defibrillator function is enabled by providing electrical energy of a selected energy/power level/voltage/current level or intensity delivered for a selected duration upon sensing certain patterns of undesirable heart activity wherein said undesirable heart activity necessitates an external delivery of a controlled electrical energy pulse for stimulating a selected heart activity. The defibrillator function is enabled by an intelligent defibrillator appliance that operates in a manner similar to the functions of an intelligent ECG appliance with the additional capability of providing external electrical stimuli via for example a wireless contact system pasted on various locations of the torso. The electrical stimuli are delivered in conjunction with the intelligent defibrillator device or the mobile device performing the additional functions of an intelligent defibrillator appliance. The control actions for providing real time stimuli to the heart of electrical pulses, is enabled by the intelligent defibrillator appliance by itself or in conjunction with an external server/intelligent appliance where the protocols appropriate for the specific individual are resident. The defibrillation actions are controlled in conjunction with the real time ECG data for providing a comprehensive real time solution to the individual suffering from abnormal or life threatening heart activity/myocardial infraction. Additionally, by continuously wearing the paste on wireless contacts that can provide the electrical impulse needed, the individual is instantaneously able to get real time attention/action using a specifically designed wearable intelligent defibrillator appliance or a combination of an intelligent ECG plus defibrillator appliance. Further the mobile device such as a cellular telephone or other wearable mobile devices can be configured with the appropriate power sources and the software for performing the additional functions of an intelligent defibrillator appliance specifically tailored to the individual.

The cellular telephone/mobile device can receive signals from the ECG machine/appliance or as an intermediary device that transmits/receives the ECG data and results from a stationary or portable ECG appliance. The ability of the individual to obtain an ECG profile of the heart at a selected time and in a selected location is critical to getting timely attention and for survival. Getting attention within 10 to 20 minutes of a heart attack is crucial beyond that the chances for survival diminish significantly. The smart phone helps the patient to quickly communicate his/her location and or discover the location of the nearest health care facility that has the requisite cardiac care facilities and other facilities. The mobile device that the individual is carrying on the person is enabled to provide the exact location of the individual in conjunction with the global positioning system. In addition the system is enabled to provide the directions and estimated travel time to/from the health care facility to the specific mobile device/individual.

The coach system may implement one or more of the interventions:

| Interventions | Details |
|---|---|
| Assess readiness and blocks to learning. Include significant other (SO). | Misconceptions and denial of the diagnosis because of long-standing feelings of well-being may interfere with patient and SO willingness to learn about disease, progression, and prognosis. If patient does not accept the reality of a life-threatening condition requiring continuing treatment, lifestyle and behavioral changes will not be initiated or sustained. |
| Define and state the limits of desired BP. Explain hypertension and its effects on the heart, blood vessels, kidneys, and brain, | Provides basis for understanding elevations of BP, and clarifies frequently used medical terminology. Understanding that high BP can exist without symptoms is central to enabling patient to continue treatment, even when feeling well. |
| Assist patient in identifying modifiable risk factors (obesity; diet high in sodium, saturated fats, and cholesterol; sedentary lifestyle; smoking; alcohol intake of more than 2 oz per day on a regular basis; stressful lifestyle). | These risk factors have been shown to contribute to hypertension and cardiovascular and renal disease. |
| Problem-solve with patient to identify ways in which appropriate lifestyle changes can be made to reduce modifiable risk factors. | Changing "comfortable or usual" behavior patterns can be very difficult and stressful. Support, guidance, and empathy can enhance patient's success in accomplishing these tasks. |
| Discuss importance of eliminating smoking, and assist patient in formulating a plan to quit smoking. | Nicotine increases catecholamine discharge, resulting in increased heart rate, BP, vasoconstriction, and myocardial workload, and reduces tissue oxygenation. |
| Reinforce the importance of adhering to treatment regimen and keeping follow-up appointments. | Lack of cooperation is a common reason for failure of antihypertensive therapy. Therefore, ongoing evaluation for patient cooperation is critical to successful treatment. Compliance usually improves when patient understands causative factors and consequences of inadequate intervention and health maintenance. |
| Instruct and demonstrate technique of BP self-monitoring, Evaluate patient's hearing, visual acuity, manual dexterity, and coordination. | Monitoring BP at home is reassuring to patient because it provides visual and positive reinforcement for efforts in following the medical regimen and promotes early detection of deleterious changes. |
| Help patient develop a simple, convenient schedule for taking medications. | Individualizing medication schedule to fit patient's personal habits and needs may facilitate cooperation with long-term regimen. |
| Explain prescribed medications along with their rationale, dosage, expected and adverse side effects, and idiosyncrasies | Adequate information and understanding that side effects (mood changes, initial weight gain, dry mouth) are common and often subside with time can enhance cooperation with treatment plan. |
| Diuretics: Take daily doses (or larger dose) in the early morning; | Scheduling minimizes nighttime urination. |
| Weigh self on a regular schedule and record; | Primary indicator of effectiveness of diuretic therapy. |
| Avoid or limit alcohol intake; | The combined vasodilating effect of alcohol and the volume-depleting effect of a diuretic greatly increase the risk of orthostatic hypotension. |
| Notify physician if unable to tolerate food or fluid; | Dehydration can develop rapidly if intake is poor and patient continues to take a diuretic. |
| Antihypertensives: Take prescribed dose on a regular schedule; avoid skipping, altering, or making up doses; and do not discontinue without notifying the healthcare provider. Review potential side effects and/or drug interactions; | Because patients often cannot feel the difference the medication is making in blood pressure, it is critical that there is understanding about the medications' working and side effects. For example, abruptly discontinuing a drug may cause rebound hypertension leading to severe complications, or medication may need to be altered to reduce adverse effects. |
| Rise slowly from a lying to standing position, sitting for a few minutes before standing. Sleep with the head slightly elevated. | Measures reduce severity of orthostatic hypotension associated with the use of vasodilators and diuretics. |
| Suggest frequent position changes, leg exercises when lying down. | Decreases peripheral venous pooling that may be potentiated by vasodilators and prolonged sitting/standing. |
| Recommend avoiding hot baths, steam rooms, and saunas, especially with concomitant use of alcoholic beverages. | Prevents vasodilation with potential for dangerous side effects of syncope and hypotension. |
| Instruct patient to consult healthcare provider before taking other prescription or over-the-counter (OTC) medications. | Precaution is important in preventing potentially dangerous drug interactions. Any drug that contains a sympathetic nervous stimulant may increase BP or counteract antihypertensive effects. |
| Instruct patient about increasing intake of foods/fluids high in potassium (oranges, bananas, figs, dates, tomatoes, potatoes, raisins, apricots, | Diuretics can deplete potassium levels. Dietary replacement is more palatable than drug supplements and may be all that is needed to correct deficit. Some studies show that 400 mg of calcium per day can lower |

-continued

| Interventions | Details |
| --- | --- |
| Gatorade, and fruit juices and foods/fluids high in calcium such as low-fat milk, yogurt, or calcium supplements, as indicated). | systolic and diastolic BP. Correcting mineral deficiencies can also affect BP. |
| Review signs and symptoms requiring notification of healthcare provider (headache present on awakening that does not abate; sudden and continued increase of BP; chest pain, shortness of breath; irregular or increased pulse rate; significant weight gain (2 lb per day or 5 lb per wk) or peripheral and abdominal swelling; visual disturbances; frequent, uncontrollable nosebleeds; depression or emotional lability; severe dizziness or episodes of fainting; muscle weakness or cramping; nausea/vomiting; excessive thirst. | Early detection of developing complications, decreased effectiveness of drug regimen or adverse reactions to it allows for timely intervention. |
| Explain rationale for prescribed dietary regimen (usually a diet low in sodium, saturated fat, and cholesterol). | Excess saturated fats, cholesterol, sodium, alcohol, and calories have been defined as nutritional risks in hypertension. A diet low in fat and high in polyunsaturated fat reduces BP, possibly through prostaglandin balance in both normotensive and hypertensive people. |
| Help patient identify sources of sodium intake (table salt, salty snacks, processed meats and cheeses, sauerkraut, sauces, canned soups and vegetables, baking soda, baking powder, monosodium glutamate). Stress the importance of reading ingredient labels of foods and OTC drugs. | Two years on a moderate low-salt diet may be sufficient to control mild hypertension or reduce the amount of medication required. |
| Encourage patient to establish an individual exercise program incorporating aerobic exercise (walking, swimming) within patient's capabilities. Stress the importance of avoiding isometric activity. | Besides helping to lower BP, aerobic activity aids in toning the cardiovascular system. Isometric exercise can increase serum catecholamine levels, further elevating BP. |
| Demonstrate application of ice pack to the back of the neck and pressure over the distal third of nose, and recommend that patient lean the head forward, if nosebleed occurs. | Nasal capillaries may rupture as a result of excessive vascular pressure. Cold and pressure constrict capillaries to slow or halt bleeding Leaning forward reduces the amount of blood that is swallowed. |
| Provide information regarding community resources, and support patient in making lifestyle changes. Initiate referrals as indicated, | Community resources such as the American Heart Association, "coronary clubs," stop smoking clinics, alcohol (drug) rehabilitation, weight loss programs, stress management classes, and counseling services may be helpful in patient's efforts to initiate and maintain lifestyle changes. |

Yet other intervention can include music, image, or video. The music can be synchronized with respect to a blood pulse rate in one embodiment, and in other embodiments to biorhythmic signal—either to match the biorhythmic signal, or, if the signal is too fast or too slow, to go slightly slower or faster than the signal, respectively. In order to entrain the user's breathing, a basic melody is preferably played which can be easily identified by almost all users as corresponding to a particular phase of respiration. On top of the basic melody, additional layers are typically added to make the music more interesting, to the extent required by the current breathing rate, as described hereinabove. Typically, the basic melody corresponding to this breathing includes musical cords, played continuously by the appropriate instrument during each phase. For some applications, it is desirable to elongate slightly the length of one of the respiratory phases, typically, the expiration phase. For example, to achieve respiration which is 70% expiration and 30% inspiration, a musical composition written for an E:I ratio of 2:1 may be played, but the expiration phase is extended by a substantially-unnoticed 16%, so as to produce the desired respiration timing. The expiration phase is typically extended either by slowing down the tempo of the notes therein, or by extending the durations of some or all of the notes.

Although music for entraining breathing is described hereinabove as including two phases, it will be appreciated by persons skilled in the art that the music may similarly include other numbers of phases, as appropriate. For example, user may be guided towards breathing according to a 1:2:1:3 pattern, corresponding to inspiration, breath holding (widely used in Yoga), expiration, and post-expiratory pause (rest state).

In one embodiment, the volume of one or more of the layers is modulated responsive to a respiration characteristic (e.g., inhalation depth, or force), so as to direct the user to change the characteristic, or simply to enhance the user's connection to the music by reflecting therein the respiration characteristic. Alternatively or additionally, parameters of the sound by each of the musical instruments may be varied to increase the user's enjoyment. For example, during slow breathing, people tend to prefer to hear sound patterns that have smoother structures than during fast breathing and/or aerobic exercise.

Further alternatively or additionally, random musical patterns and/or digitized natural sounds (e.g., sounds of the ocean, rain, or wind) are added as a decoration layer, especially for applications which direct the user into very slow breathing patterns. The inventor has found that during very slow breathing, it is desirable to remove the user's focus from temporal structures, particularly during expiration.

Still further alternatively or additionally, the server maintains a musical library, to enable the user to download appropriate music and/or music-generating patterns from the Internet into device. Often, as a user's health improves, the music protocols which were initially stored in the device are no longer optimal, so the user downloads the new protocols, by means of which music is generated that is more suitable for his new breathing training. The following can be done:

1. A method of managing electronic medical record (EMR)/electronic healthcare record (EHR) for a subject, comprising:
    obtaining clinical data from one or more laboratory test equipment and checking the data on a blockchain;
    obtaining genetic clinical data from one or more genomic equipment and storing genetic markers in the EMR/HER including germ line data and somatic data over time;
    obtaining clinical data from a primary care or a specialist physician database;
    obtaining clinical data from an in-patient care database or from an emergency room database;
    saving the clinical data into a clinical data repository;
    obtaining health data from fitness devices or from mobile phones;
    obtaining behavioral data from social network communications and mobile device usage patterns;
    saving the health data and behavioral data into a health data repository separate from the clinical data repository; and
    providing a decision support system (DSS) to apply genetic clinical data to the subject, and in case of an adverse event for a drug or treatment, generating a drug safety signal to alert a doctor or a manufacturer, wherein the DSS includes rule-based alerts on pharmacogenetics, oncology drug regimens, wherein the DSS performs ongoing monitoring of actionable genetic variants.

2. The method of claim 1, comprising.
    mining the clinical data repository and health data repository for one or more markers associated with one or more health conditions and for patients sharing similarity with the subject;
    identifying at least one similar health conditions and identifying one or more corrective actions previously taken in the repository and the result of each corrective action for the one or more health conditions;
    presenting the corrective action and result to a doctor and recommending an action to reduce risk from the predicted health condition; and
    monitoring the health condition using updates in the clinical data repository and health data repository.

3. The method of claim 1, comprising
    detecting emotional health using email, mobile phone usage pattern including frequency of messaging, and social network communications;
    correlating the emotional health with omic changes relating to genomic, proteomic, transcriptomic, nutrigenomic, metabolomic conditions, and
    generating treatment plan from a treatment template for people with similar emotional states and customizing the treatment plan; and
    tracking omic changes to emotional health changes in the subject over time.

4. The method of claim 1, comprising detecting omic changes with genomic, proteomic, transcriptomic, nutrigenomic and metabolomic analysis, and tracking omic changes to physiological changes in the subject over time.

5. The method of claim 4, comprising:
    determining dynamic trends related directly to the physiological states of the subject during healthy and diseased states by correlating patterns over time and unusual events; and
    normalizing the omic data for identifying common trends and features, searching for spike events, and clusterizing the data to determine similar subjects.

6. The method of claim 1, comprising
    providing a network to communicate cancer treatment information relating to the community;
    capturing genetic information including gene alterations and alteration quantities from one or more gene sequencers;
    linking one or more oncology consultant computers to the network;
    linking one or more treating professional computers coupled to the network; and
    storing genetic information for each patient and facilitating secured cancer treatment collaboration by the community through a server.

7. The method of claim 1, comprising monitoring drug response or drug resistance based on omic data.

8. The method of claim 1, comprising receiving treatment and outcome information associated with a patient from at least one user; organizing the treatment and the outcome information according to one or more of alteration, affected gene, affected pathway, tumor type, and treatment.

9. The method of claim 1, wherein the treatment information includes any one or more of drugs, therapeutics, named drugs, named therapeutics, drug cocktails, drug combinations, radiation, and surgery.

10. The method of claim 1, comprising identifying similar patients based on information related to genomic alteration.

11. The method of claim 1, comprising identifying similar patients based on information related to affected gene identified in a disease.

12. The method of claim 1, comprising identifying similar patients based on information related to treatment.

13. The method of claim 1, identifying, by the computer system, similar patients based on related to tumor type.

14. The method of claim 1, comprising identifying similar patients based on information relating to a combination of at least two or more of a group comprising alteration, affected gene, affected pathway, tumor type, and treatment.

15. The method of claim 1, comprising: identifying similar patients based on information related to at least one of alteration, affected gene, affected pathway, tumor type, and treatment for a patient's cancer; and aggregating, by the computer system, responsive information according to one or more of alteration, affected gene, affected pathway, tumor type, and treatment.

16. The method of claim 1, comprising aggregating similar patients within classes of alterations, wherein the classes of alteration include alterations in a specified domain of a gene and the domain includes at least a kinase domain of the gene.

17. The method of claim 16, wherein the gene includes BRAF, and the specific domains include at least one of kinase, BRAF V600E, and BRAF V600K.

18. The method of claim 1, comprising aggregating similar patient information based on functional similarity of identified alterations, which can be determined for distinct mutations having functionally similar characteristics in the cancer cells.

19. The method of claim 1, comprising performing deep learning on the clinical and health data repository.

20. A system managing electronic medical record (EMR)/electronic healthcare record (EHR) for a subject, comprising:
   a deep learning machine;
   genomic equipment storing patient data on a blockchain and coupled to the deep learning machine; and
   a processor coupled to the deep learning machine, the processor including code for:
   obtaining clinical data from one or more laboratory test equipment;
   obtaining genetic clinical data from the genomic equipment and storing genetic markers in the EMR/EHR including germ line data and somatic data over time;
   obtaining clinical data from a primary care or a specialist physician database;
   obtaining clinical data from an in-patient care database or from an emergency room database;
   saving the clinical data into a clinical data repository;
   obtaining health data from fitness devices or from mobile phones;
   obtaining behavioral data from social network communications and mobile device usage patterns;
   saving the health data and behavioral data into a health data repository separate from the clinical data repository; and
   providing a decision support system (DSS) to apply genetic clinical data to the subject, and in case of an adverse event for a drug or treatment, generating a drug safety signal to alert a doctor or a manufacturer, wherein the DSS includes rule-based alerts on pharmacogenetics, oncology drug regimens, wherein the DSS performs ongoing monitoring of actionable genetic variants.

Figure 14E:
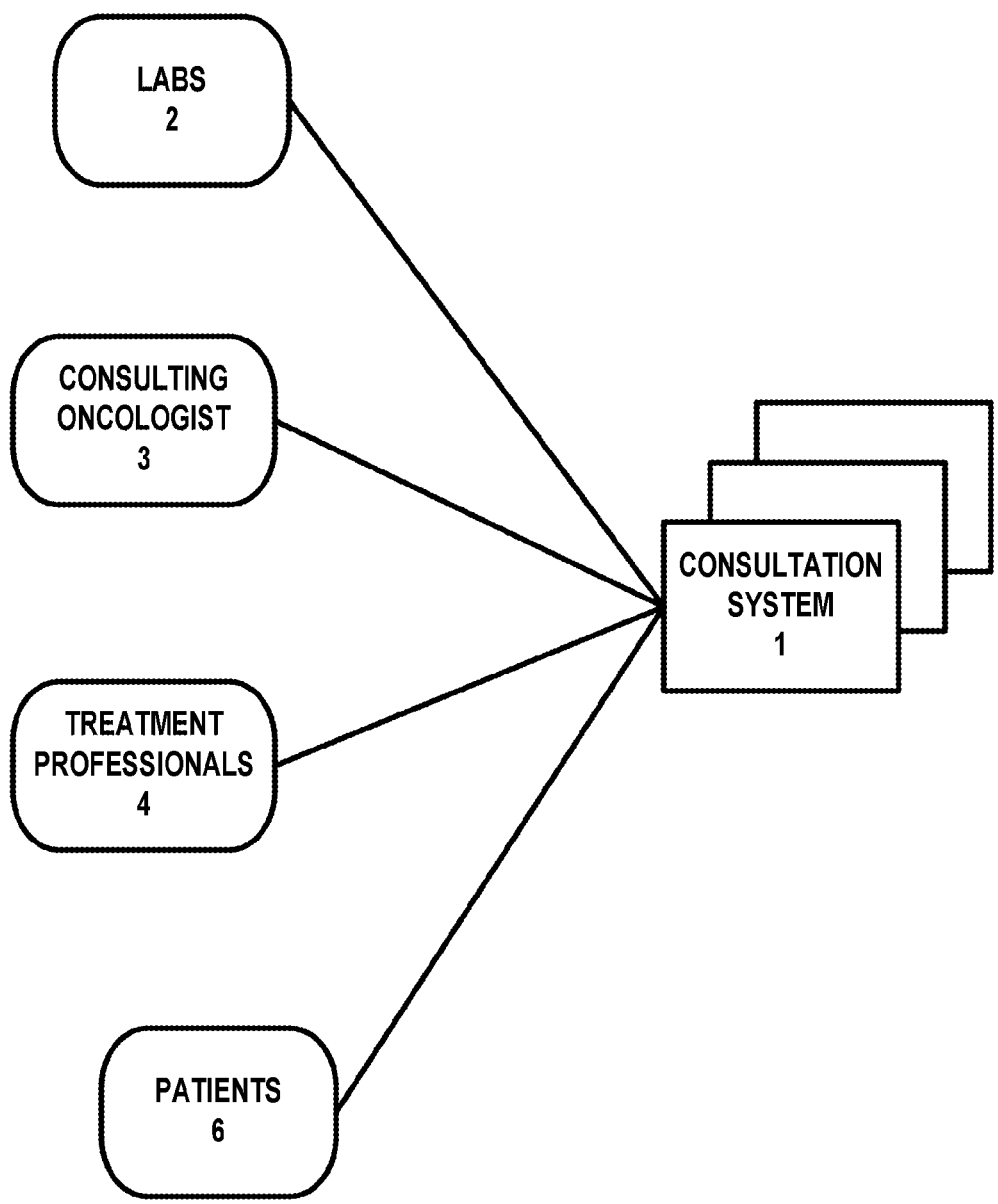

Referring now to FIG. 14E, a system with a report generator 1 for reporting on cancer test results and treatment options therefrom is schematically illustrated. The report generator system can be a central data processing system configured to establish communications directly with: a remote data site or lab 2, a consulting professional (such as university researchers or oncologists) provider 3, a medical practice/healthcare provider (treating professional) 4 and/or a patient/subject 6 through communication links. The lab 2 can be medical laboratory, diagnostic laboratory, medical facility, medical practice, point-of-care testing device, or any other remote data site capable of generating subject clinical information. Subject clinical information includes but it is not limited to laboratory test data, X-ray data, examination and diagnosis. The healthcare provider or practice 6 includes medical services providers, such as doctors, nurses, home health aides, technicians and physician's assistants, and the practice is any medical care facility staffed with healthcare providers. In certain instances the healthcare provider/practice is also a remote data site. In a cancer treatment embodiment, the subject may be afflicted with cancer, among others.

FIG. 14F illustrates one embodiment of a system for collaboratively treating a patient with cancer. In this embodiment, a treating physician/doctor logs into a consultation system 1 and initiates the process by clicking on "Create New Case" (500). Next, the system presents the doctor with a "New Case Wizard" which provides a simple, guided set of steps to allow the doctor to fill out an "Initial Assessment" form (501). The doctor may enter Patient or Subject Information (502), enter Initial Assessment of patient/case (504), upload Test Results, Subject Photographs and X-Rays (506), accept Payment and Service Terms and Conditions (508), review Summary of Case (510), or submit Forms to a consultant such as an Oncology Service Provider (512). Other clinical information for the cancer subject includes the imaging or medical procedure directed towards the specific cancer that one of ordinary skill in the art can readily identify. The list of appropriate sources of clinical information for cancer includes but it is not limited to: CT scan, MRI scan, ultrasound scan, bone scan, PET Scan, bone marrow test, barium X-ray, endoscopy, lymphangiogram, IVU (Intravenous urogram) or IVP (IV pyelogram), lumbar puncture, cystoscopy, immunological tests (anti-malignant antibody screen), and cancer marker tests.

After the case has been submitted, the Service Provider Consultant can log into the system 1 and consult/process the case (520). Using the Treating Doctors Initial Assessment and Photos/X-Rays, the Consultant will click on "Case Consultation" to initiate the "Case Consultation Wizard" (522). The consultant can fill out the "Consultant Record Analysis" form (524). The consultant can also complete the "Prescription Form" (526) and submit completed forms to the original Treating Doctor (528). Once the case forms have been completed by the Consulting Doctor, the Treating Doctor can access the completed forms using the system 1. The Treating Doctor can either accept the consultation results (i.e. a pre-filled Prescription form) or use an integrated messaging system to communicate with the Consultant (530). The Treating Doctor can log into the system 1 (532), click on Patient Name to review (534), review the Consultation Results (Summary Letter and pre-filled Prescription Form) (536). If satisfied, the Treating Doctor can click "Approve Treatment" (538), and this will mark the case as having being approved (540). The Treating Doctor will be able to print a copy of the Prescription Form and the Summary Letter for submission to pharmacy (542). Alternatively, if not satisfied, the Treating Doctor can initiate a computer dialog with the Consultant by clicking "Send a Message" (544). The Treating Doctor will be presented with the "Send a Message" screen where a message about the case under consultation can be written (546). After writing a message, the Treating Doctor would click "Submit" to send the message to the appropriate Consultant (548). The Consultant will then be able to reply to the Treating Doctor's Message and send a message/reply back to the Treating Doctor (550).

The IOT system can use blockchain to improve security and authentication, as well as virtual money such as Ether/Bitcoins to facilitate work. The use of blockchain with IOT devices is described in co-pending commonly owned application Ser. No. 15/594,311 filed May 12, 2017, the content of which is incorporated by reference.

In one embodiment a product may be any tangible or intangible thing that may be exchanged for value, excluding the first transaction 204; in other words, the value for which the product is exchanged is unrelated to the value of the product or service exchanged to produce the first transaction. The product may be a good, such as an article of manufacture or an item produced in agriculture. The product may be merchandise. The product may be a consumable.

The product may be a fixed asset. The product may be a circulating tool. The product may be a library books. The product may be capital equipment. The product may be a bill of fiat currency. The product may be commercial paper. The product may be an item, such as a coupon or voucher, which may be used as proof of payment for a service. For instance, the product may be a ticket for conveyance on a transportation carrier such as a train, bus, or airline. The product may be a ticket for an entertainment event such as a sporting event or a concert. The system can also verify the quality of services such as legal services, financial services, consulting services, financial planning services, repair services, cosmetic services, healthcare services, medical services, massage services, among others.

In some embodiments, the first computing 201 is configured to export an address to a first code such as a bar code affixed to a product. The system may include a code generator coupled to the first computing device. The code generator can be a bar code generator or a wireless code such as a near field communication (NFC) code. Upon receipt by a bar code scanner or an NFC scanner, the product authenticity can be verified. The product may combine other anti-counterfeiting measures with the first code such as a holographic icon or a special tamperproof case/housing, for example.

In some embodiments, the first code is incorporated in a manufacturing control system (not shown) that may rely upon codes, such as barcodes or NFC/RFID tags, to provide automatic identification of products. To record manufacturing transaction, the system may use a code scanner to automatically identify the product, and then may collects additional information from operators via fixed terminals (workstations), or mobile computers. The code used in the system may be matched to a data structure mapping codes to data concerning products, such as a database. The data structure mapping codes to products may be the transaction register. The data structure mapping codes to products may be separate from the transaction register. The party managing the manufacturing control system may be the party managing the system. The party managing the inventory control system may be a separate party.

In one embodiment, an address is a textual datum identifying the product or service serial number or ID number in a secured transaction. In some embodiments, the address is linked to a public key, the corresponding private key of which is owned by the recipient of the transfer of product or service. For instance, the address may be the public key. The address may be a representation, such as a hash, of the public key. The address may be linked to the public key in the memory of a computing device. Where the address is linked to a public key, the transferee in the secured transaction may record a subsequent transaction transferring some or all of the product or service to a new address in the same manner.

In some embodiments, the transaction register includes a data storage facility controlled by a trusted party. The data storage facility may include a database and the data storage facility may include a data structure such as a hash table that permits rapid lookup of data stored in the data storage facility. The trusted party may be a proprietor of the system. The trusted party may be a third-party entity, such as an entity maintaining data centers for services such as cloud-computing services. In other embodiments the at least one transaction register may include several data storage facilities maintained by one or more trusted parties; for instance, the at least one transaction register may include several data storage facilities, to which secured transactions are directed as set forth in further detail below. The data storage facilities may be on the same machine. The data storage facilities may be on the same server. The data storage facilities may be in different servers, but in the same data center. The data storage facilities may be in various data centers. The at least one transaction register may be several transaction registers to which secured transactions are directed.

The transaction register may include a distributed, consensus-based ledger and the transaction register may include a hash chain, in which data is added during a successive hashing process to ensure non-repudiation. The transaction register may include a private register run by a predetermined group of entities. For example, the group may be the FDA and select trusted pharmaceutical companies. In other cases, the group can be a number of banks working together. In yet other cases, the group can be a stock market such as NYSE or NASDAQ and banks/traders. In yet other cases, the group can be members of the Army, Air Force, or Navy, or can even be all three. The advantage of having select group members is that sensitive data can be contained to the group for a predetermined purpose rather than broadcasted to the world for anyone to inspect in an encrypted form.

In some embodiments, the transaction register includes a block chain. In one embodiment, the block chain is a transaction register that records one or more new secured transactions in a data item known as a block. The blocks may be created in a way that places the blocks in chronological order, and links each block to a previous block in the chronological order, so that any computing device may traverse the blocks in reverse chronological order to verify any secured transactions listed in the block chain. As a non-limiting example, each new block may be required to contain a cryptographic hash describing the previous block. In some embodiments, the block chain contains a single first block, known as a "genesis block." As an example, the protocol may require a new block to contain a cryptographic hash describing its contents; the cryptographic hash may be required to satisfy a mathematical condition, achieved by having the block contain a number, called a nonce, whose value is determined after the fact by the discovery of the hash that satisfies the mathematical condition. Continuing the example, the protocol may be able to adjust the mathematical condition so that the discovery of the hash describing a block and satisfying the mathematical condition requires more or less steps, depending on the outcome of the previous hashing attempt. The mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, the production of a new block according to the protocol is known as "mining." Each block created in the block chain 206 may contain a record or transaction describing one or more addresses that receive an incentive, such as product or service, as the result of successfully mining the block 206b.

Additional data linked to a secured transaction may be incorporated in blocks in the block chain; for instance, data may be incorporated in one or more fields recognized by block chain protocols that permit a person or computer forming a transaction to insert additional data in the block chain. In some embodiments, additional data is incorporated in an unspendable transaction field. For instance, the data may be incorporated in an OP RETURN within the Bitcoin block chain. In other embodiments, additional data is incorporated in one signature of a multi-signature transaction. In an embodiment, a multi-signature transaction is a secured transaction to two or more addresses. In some embodiments, the two or more addresses are hashed together to form a single address, which is signed in the digital signature of the secured transaction. In other embodiments, the two or more addresses are concatenated. In some embodiments, the two or more addresses may be combined by a more complicated process, such as the creation of a merkle tree as described below. In some embodiments, one or more addresses incorporated in the multi-signature transaction are typical secured addresses, such as addresses linked to public keys as described above, while one or more additional addresses in the multi-signature transaction contain additional data related to the transaction; for instance, the additional data may indicate the purpose of the transaction, aside from an exchange of product or service, such as the item for which the product or service was exchanged.

The transaction register may include a block chain ecosystem data structure. In one embodiment, a block chain ecosystem data structure is a data structure that is located outside a block chain but uses the block-chain as a basis for reliability or security by giving elements in the block chain ecosystem data structure a secure and reproducible relationship with elements within the block chain. The block chain ecosystem data structure may create the relationship by inserting representations of elements from the block chain ecosystem data structure into blocks in the block chain; for instance by "merge hashing," where the elements are part of what gets hashed as block chain data during the hashing algorithm for blocks as described above. For example, in some embodiments, the transaction register may include an alternative chain. In one embodiment, an alternative chain is one or more blocks (not shown) that are incorporated into a blockchain, by including at least one hash representing data in the alternative chain in at least one block in the blockchain that is mined; where the mathematical puzzle involved in creating the new block is the production of a new hash, the additional hash in the block may not affect the degree of difficulty, and thus miners are not put at a computational disadvantage incorporating the alternative chain. The alternative chain may be incorporated using one or more hash trees, such as one or more merkle trees (not shown). The merkel tree may a structure containing a hash of each datum in the alternative chain as leaf notes, with each internal node containing a hash of all of its child nodes; thus, by the avalanche principle, the root of a merkle tree may be a hash that recursively represents all the data hashed in the merkle tree, and thus a set of data in the alternative chain, so that incorporation of the root in a block in the blockchain 206 amounts to incorporation of the data from the alternative chain that the merkle tree represents. A miner may charge a fee for incorporating the alternative chain in a block the miner mines. In an embodiment, verification of a transaction filed in the alternative chain involves first locating the transaction in the alternative chain, verifying its digital signature, and verifying each hash between that location and the blockchain block (for instance by verifying each hash in the merkle tree from the leaf corresponding to the transaction to the root), verifying the hash of the block incorporating the alternative chain, and then verifying the block up the block chain as described above. In other embodiments, the hash tree is a tiger tree. In other embodiments, the alternative chain is linked to the block chain via a hash chain (not shown).

In some embodiments, data linking the block chain ecosystem data structure to the block chain is incorporated in an unspendable transaction field. For instance, the data may be incorporated in an OP RETURN within the Bitcoin block chain. In other embodiments, data linking the block chain ecosystem data structure to the block chain is incorporated in one signature of a multi-signature transaction. For example, the root of a merkle tree may occupy one or more addresses that are signed in a multi-signature transaction.

In other embodiments, elements in the block chain ecosystem data structure are mapped to elements in the block chain by means of an agreed-upon mapping protocol. For instance, rather than inserting a hash from the block chain ecosystem into the block chain, an algorithm may establish a mathematical relationship between an element in the block chain ecosystem data structure and an element in the block chain; the mathematical relationship may be unique to the element in the block chain ecosystem data structure. The mathematical relationship may be unique to the element in the block chain. As a non-limiting example, elements in a block chain ecosystem data structure may be mapped to particular transactions in the block chain. Elements in the block chain ecosystem data structure may be mapped to particular addresses in the block chain. Elements in the block chain ecosystem data structure may be mapped to particular hashes corresponding to blocks. The mapping may be performed using digital signatures; for instance, the owner of a private key corresponding to a public key represented by an address in the block chain may sign an element in the block chain ecosystem with the private key. Each element in the block chain may be hashed, and the space containing all hashes may be mapped to elements in the block chain using a mathematical algorithm.

In other embodiments, the block chain ecosystem data structure may incorporate a side chain. In some embodiments, a side chain is a block chain that is operated parallel to a main block chain, using transactions or transaction outputs extracted from and later merged back into the main block chain via two-way pegging. The transactions or transaction outputs may be merged back into the main block chain by performing a combined hash of the latest link in the side chain with the latest link in the block chain. The combined hash may use a merkle tree as described above to reduce the computational difficulty associated with a combined hash of two entire blocks.

In an aspect, encoded data derived from images of local regions of a physical object are used to securely reference ("fingerprint") physical assets based on unique surface-level texture patterns, rendering the physical asset traceable as a digital item. For pets, encode picture and sound can render the asset traceable. For newborn babies, the encoded picture, sound, and fingerprint/footprint can render the child traceable. A cryptographically-safe hash function is used to fingerprint digital assets. The system provides a framework for authenticating different objects or materials via extracting and matching their fingerprints. Biometric fingerprinting processes, which use patterns such as ridge ending and bifurcation points as the "interest points," can be used. Stereo photometric techniques can be used for reconstructing local image regions of objects that contain the surface texture information. The interest points of the recovered image regions can be detected and described by state-of-the-art computer vision algorithms. Together with dimension reduction and hashing techniques, the approach is able to perform object verification using compact image features for virtually any object, including documents, for practical physical object authentication tasks.

In one implementation, a digital asset is certified via embedding its SHA256 digest in the blockchain. This is done by generating a transaction that encodes/contains the hash via an OP_RETURN script. This is a bitcoin scripting opcode that marks the transaction output as provably unspendable and allows a small amount of data to be inserted, which is the digital asset hash, plus a marker to identify all of a company's transactions. Once the transaction is confirmed by the blockchain, the digital asset is permanently certified and proven to exist at least as early as the time the transaction was confirmed. If the document hadn't existed at the time the transaction entered the blockchain, it would have been impossible to embed its digest in the transaction (This is because of the hash function's property of being second pre-image resistant). Embedding a hash and then adapting a future document to match the hash is also impossible (due to the pre-image resistance of hash functions). Hence, once the blockchain confirms the transaction generated for the digital asset, its existence is proven, permanently, with no trust required. To manually confirm the asset's existence at the timestamped time, the system calculates the document's SHA256 digest and finds a transaction in the bitcoin blockchain containing an OP_RETURN output with the document's hash prepended by marker bytes. The existence of that transaction in the blockchain proves that the digital asset (or intellectual property) existed at the time the transaction got included into a block. The system proves data ownership without revealing actual data by publicly revealing the digest and if conflict arises the device can produce the data that generates the digest. The system can prove certain data exists at a certain moment of time. As we use the blockchain to store the document proof, the system can certify the existence of your document without the need of a central authority. The system can check for asset integrity. The system will only recognize it if it is completely and fully the same document. The slightest change will be recognized as different, giving user the security that certified data can't be changed.

Figure 15A:
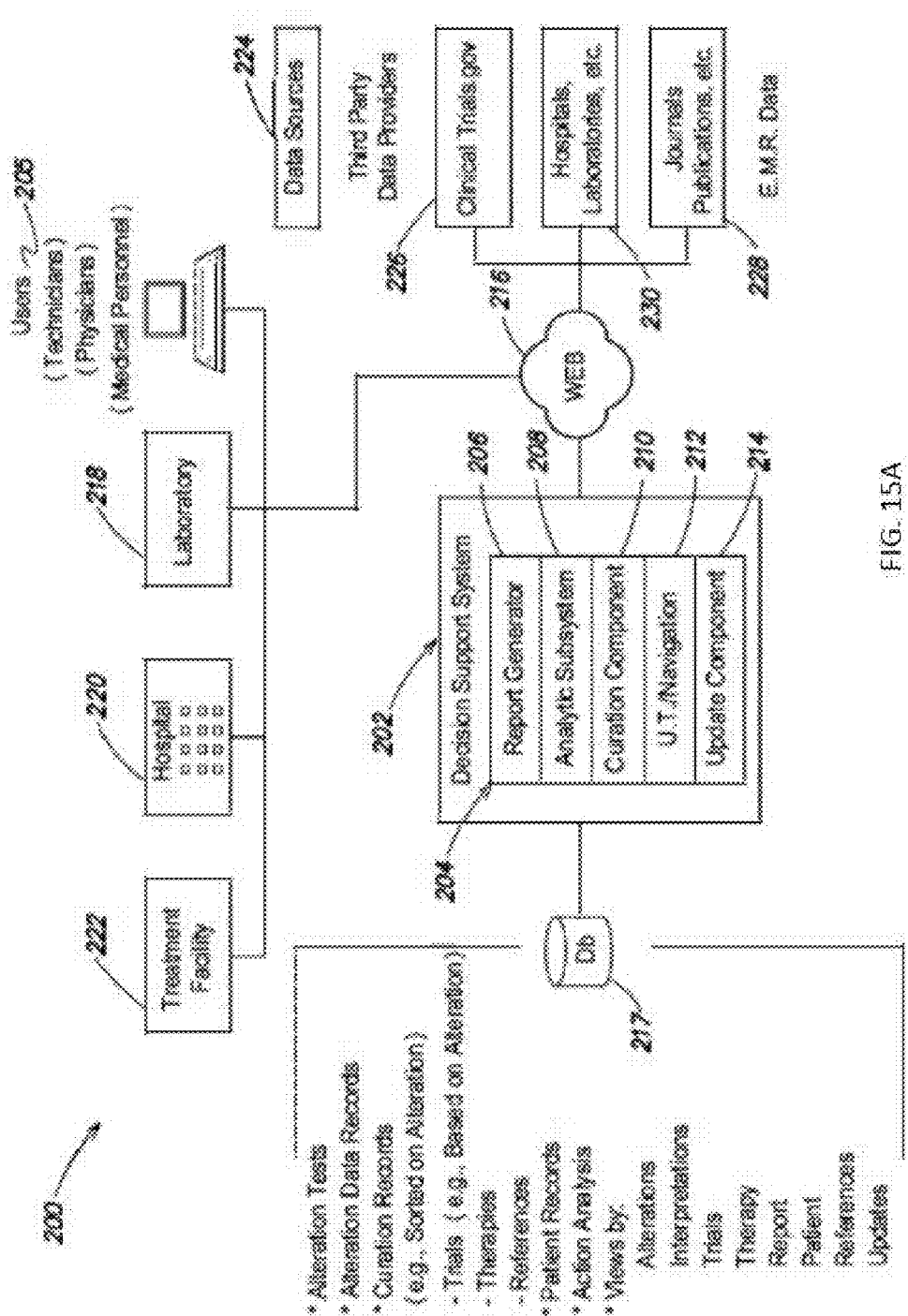

Show in FIG. 15A is an example embodiment of a decision support system 200 for managing genomic testing information and for detecting adverse events associated with a drug and treatment. The system 200 can be configured to provide a single reporting source for accessing and applying available information on a patient's cancer. According to some embodiments, genomic testing on the patient's cancer provides specific information the tumor, one or more genes implicated by the tumor, and one or more alterations within the genes which can be displayed by the system 200 through a web interface 202. In some embodiments, the web interface 202 can include an alteration engine 204 that performs any of the operations discussed above with respect to the alteration engine 104. For example, the web interface and/or alteration engine 204 can be configured to use the testing information on tumor, gene, and alteration for a patient to manage delivery of curated information to end users (e.g., technicians, physicians, medical personal, etc., at 205) over a communication network 216. In one embodiment, the alteration engine 204 can include a UI or navigation component 212 configured to generate displays that focus users (e.g., physicians) on actionable information within the genomic test results and associated information. For example, the UI component 212 can display navigable data structures including information on genes and alterations identified in a genomic test coupled with indicators informing the user of available actionable information associated with a patient's cancer.

According to some embodiments, the alteration engine 204 can include specific component for provide specific functionality on the web interface 202. For example, the alteration engine 204 can also include a report generator component 206 configured to generate physical and/or static report for downloading through the web interface (e.g., shown in FIGS. 9A-9N). The alteration engine 204 can also include an analytic subsystem 208 an analytic subsystem configured to identify matches information between a current patient's tumor type, gene, and/or alteration and include or identify the matching information items for display in the patient's test results. According another embodiment, the alteration engine can also include a curation component 210 configured to generated curated information for use on the system. The curated information can include interpreted statements regarding any one or more of genomic alterations, an implicated gene, a patient's tumor type, and/or potentially applicable therapies for a patient's cancer. In some examples, the curation component can be accessed by human operators "curators" who generate and/or approve system generated interpreted statement regarding genomic alterations, an implicated gene, a patient's tumor type, and/or potentially applicable therapies. As discussed, the alteration engine can also include the UI component 212 configured to generate and display navigable data structures (e.g., bricks and drawers) which include information on genes and alterations identified in a genomic test, which can be coupled with indicators for actionable information associated with a patient's cancer. The UI component 212 can transition the system to the actionable information (e.g., therapy information items, trial information items, reference information items) responsive to selection in the user interface. In further embodiments, the alteration engine can include an update component 214 configured to track any updates to genomic alterations and any information associated with the genomic alterations. In one embodiment, the update component 214 can identify updates information for display by the UI component 212. Various embodiments, of the alteration engine components are configured to perform the function and operations discussed above with respect to the alteration engine 104 and associated components. According to some embodiments, the web interface 202 can be accessed by users (e.g., 205) over the internet. The user can access the web interface from a variety of location (e.g., laboratory 218, hospital 220, and treatment facility 222). In various embodiments, the users at any one or more of 218-222 can share genomic test reports with each other. For example, the web interface 202 can be configured to provide social functions between users. In some embodiments, the web interface can limit sharing to practice groups, within treatment facilities, or within medical institutions (e.g., hospitals). According to one aspect, sharing of test results and associated genomic information on patients can create a strong community of physicians, and foster discussion about treatment or even specific patients. According to some embodiments, the web interface 202 stores genomic test information in database 217. Database 217 is illustrated as a single database, but in other embodiments, database 217 can include any storage medium or organizational unit for storing and accessing genomic test results and associated information. Further embodiments can include a plurality of databases and can also include distributed data architectures. According to one embodiment, database 217 can include a variety of data records accessed by the web interface 202 to manage delivery of genomic test results and associated information. For example, the database can include information on genomic testing. In one example, genomic test results are stored and associated with patient records. The genomic test results can include information on genomic alterations. Specific genomic alterations can be stored in database 217 and access for presenting information within a display of a patient's test report. The database can include curation records stored and associated with any one or more of a tumor type, gene, and/or genomic alteration. Information on clinical trial can likewise be stored as information items associated with any one or more of a tumor type, gene, and/or genomic alteration. The database 217 can also store therapy information and references information and provide associated for either to any one or more of a tumor type, gene, and/or genomic alteration. The database 217 can also be configured to track and store information on updates to any information within the database. In one example, updates can be flagged by other system components and the flags resolved or remove once viewed. In further embodiments, the database can store information on data views for used by web interface and/or the UI component 212. The views can include, for example, alteration views, genomic interpretation views, clinical trial views, therapy views, static report views, patient record views, references views, and updates views. Each one or more of the views can be accessed and used by the web interface to present information on genomic testing and associated information to a user. In some examples, the system and/or web interface can be configured to capture information from external information sources for storage in database 217. In one example, external data source 224 can contain information related to a patient's tumor type, gene, and/or alteration. The information from the external information can be captured and stored as records in database 217 accessible via the relationship to the tumor type, gene, and/or alteration. According to some embodiments, the information stored in database 217 can include reference to the external information source. For example, clinical trial information items can include links to clinicaltrials.gov 226, reference information items can include links to PubMed.gov (e.g., 228). In further embodiments, the web interface 202 can be configured to access genomic alteration information for cancer diagnoses made at a hospital or laboratory (e.g., 230). For example, the web interface can capture genomic information from EMR (electronic medical records) to retrieve tumor type, implicated gene, and/or alteration type for storage in database 217. In some implementations, references or links to the specific medical records can also be stored in the database. In one example, the links to the medical records can be presented in a dynamic display generated on system 200. According to one aspect, the database 217 and all associated information can be organized or accessed based on one or more of tumor type, gene, and alteration. In one embodiment, the tumor type, gene, and alteration data is stored as a data unit (e.g., a tuple). The data unit can be used by the system to identify or display related information based on matching any one or more of the tumor type, gene, and alteration. In further embodiments, each data unit can be linked to actionable information (where it exists). For example, each data unit can be linked to a matching therapy (e.g., a therapy information item describing a specific therapy, application, etc.). In another example, data units can be linked to a matching clinical trial (e.g., stored as a clinical trial information item). According to one embodiment, associated of all the information in the database according to tumor, gene, or alteration provides insight into prescribed uses of therapies (on-label) and off-label applications for such therapies. In one example, off-label used can be identified based on alteration (e.g., different tumors but same alteration—provides relation information on a potentially effective therapy the current patient's cancer. According to another embodiment, each record can be associated with a data space for an update flag. Responsive to any update to information on the database 217, the system can enter information in the data space for the update flag. Tracking updates to genomic alteration and associated information facilitates user awareness of potential significant changes in a patient report. Further, tracking of update information in the database 217 enables the system to deliver notification regarding any updates. In some further embodiment, social functions can have associated records in the database. For example, permission information (e.g., who can share a report and/or who can receive a shared report) can be associated with test reports stored in database 217.

FIG. 15B shows the patient site 104 and showing a patient 502 lying on a bed 504 and being attended by one or more external sensors 302. Further, a medical practitioner 506 (e.g., such as nursing personnel or other non-physician medical professional) is shown to interact with the patient 502 and provide associated treatments. Further a remote computer 104, located remotely, being positioned for inspection of both the patient 502 and the medical practitioner 506 using video-conferencing with the medical practitioner 506 and perhaps with the patient 502 to enable efficient and accurate diagnosis and treatment of the patient 502. The video conferencing with among the medical practitioners present both at the remote computer 102 and the patient site 104, and the patient 506 can enable the use of the screen 306 and camera 308 present at both the remote computer 102 and the patient site 104. Furthermore, when treatment is in progress by the patient site medical practitioner, the remote computer site medical practitioner can inspect the treatment during its progress and thus ensure that optimum professional medical treatment is being accomplished.

FIG. 15C is a schematic diagram of the system 100 in which the present invention is embodied, according to embodiments as disclosed herein. The IOT system 100 can be configured to include sensor(s) 302, data transceiver(s) 304, screen(s) 306, camera(s) 308, communicator(s) 310, remote computer 312, analyzer 314, and treatment recommender 316. In an embodiment, the sensors 302 can be configured to sense the biological parameters associated with the patient. The sensors 302 can be configured to be implanted externally or internally on/in the patient body, such as to monitor the patient biological parameters. In an embodiment, the sensors 302 described herein can be implantable, non-implantable, or a combination thereof. In an example, the sensors 302 can include, but not limited to, transthoracic impedance sensor, minute ventilation sensor, respiratory rate sensor, heart monitor, accelerometer, intracardiac pressure sensor, posture sensor, hear rate monitoring sensor, weighing scale (mass sensor), blood pressure cuff (or pressure sensor), external monitor, external meters, fluid sensor, temperature sensor, or any other type of sensors capable of providing data related to patient cardiac, blood pressure, obesity, glucose level, diabetes, posture, diseases, cancer, or any other type of information associated with the patient health. In one example, the external sensor can include weighing scale which may include a digital communication link with the system 100 or which may provide data that is manually entered into different devices present in the system 100. In an embodiment, the biological parameters described herein can include, for example, but not limited to, heart rate, blood sugar level, blood pressure level, arrhythmia status, origin of arrhythmia, patient symptoms, pulse rate, patient posture information, and the like. In an embodiment, the data transceiver 304 described herein can be configured to communicate data to the remote computer 102 over the communication network 106. The data transceiver 304 can be configured to be coupled to the sensors 302, such as to transfer the biological parameters associated with the patient. The transceiver 304 can be configured to directly or indirectly communicate with the sensors 302 over the communication network 106. In an embodiment, the screen 306 described herein can be configured to display information associated with the patient. The screen 306 can be configured to be couple or included in the remote computer 102 and the patient site 104, such as to display a visual representation of the medical practitioners 206, 208, and the patient. Further, the medical practitioners 206 and 208 can use the screen 306 to view the patient records and other information and provide treatment recommendations to the patient. Furthermore, the medical practitioners 206 and 208 can use the screen 306 to analyze the various electronic medical records (EHR) associated with the plurality of patients. The statistic, graphical, and the like presentation of the medical information can be presented on the screen 306 to take apt decision and provide treatment recommendations for the patient(s). In one embodiment, the camera includes the infrared and wide-angle lens to capture dimensions of the patient. In an embodiment, the camera 308 described herein can be configured to provide video conferencing between the medical practitioners 206 and 208 present at the remote computer 102 and the patient site 104. The camera 308 can be configured to be included or coupled to the remote computer 102 and the patient site 104, such as to provide video conferencing among the medical practitioners 206 and 208. In an embodiment, the communicator 310 can be configured to provide communication between the remote computer 102 and the patient site 104. The communicator 310 can be configured to include interface/communication links to provide communication among the devices present in the system 100. The communication described herein can be direct, indirect, or a combination thereof. In an embodiment, the remote computer 312 can be configured to provide analyzed information to the medical practitioners 206 and 208. The remote computer 312 can be configured to enable communication among the medical practitioners 204, 208, and the patient. In an embodiment, the analyzer 314 can be configured to be coupled to or included into the remote computer 102 to make treatment recommendations by comparing medical indications related to a large population to the patient condition based on the medical sensor output. The analyzer 314 can be configured to analyze the EHRs associated with the plurality of patients to provide treatment recommendations to the patients suffering with same or similar type of diseases. Further, exemplary information analyzed by the analyzer 314 are described in conjunction with FIG. 15D. In an embodiment, the treatment recommender 316 described herein can be configured to be coupled to or included into the analyzer 314 to provide a proposed treatment to the medical practitioners 206, 208, and the patient.

Figure 15D:
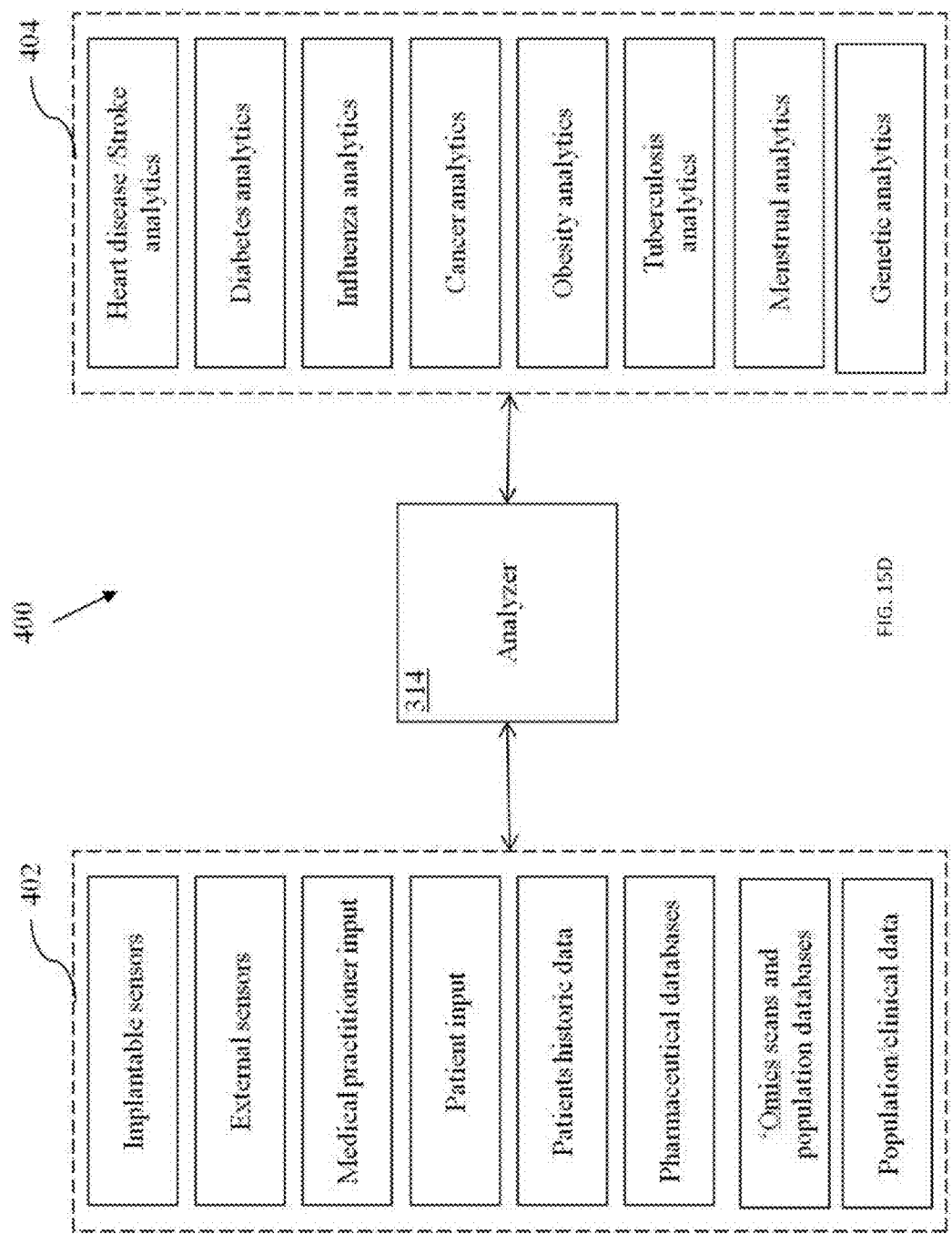

FIG. 15D is a schematic diagram illustrating exemplary analysis 400 of biological information received from various sources 402. In an embodiment, the analyzer 314 can be configured to receive the biological information associated with various sources. The various sources described herein can include for example, but not limited to, implantable sensors, external sensors, medical practitioner input, patient input, patients historic data, pharmaceutical databases, omics scans of the patient over time, population/clinical data, and the like. The omic test can include genomic, proteomic, transcriptomic, nutrigenomic or metabolomic tests, as detailed below. In an embodiment, the implantable and external sensors described herein can be configured to provide data related to patient cardiac, blood pressure, obesity, glucose level, diabetes, posture, diseases, cancer, or any other type of information associated with the patient health. In an embodiment, the medical practitioner input described herein can include an interface or data entry device accessible to a medical practitioner, medical personal or other user. Exemplary data entry devices include keyboard, mouse, trackball, controller, microphone, touch-sensitive screen, removable media storage device, PDA, or any other type of device for providing data to the analyzer 314. The data entered by the medical practitioner can include, for example, but not limited to, prescription information, medical records, patient symptoms, observation data, or any other information. In one example, the medical practitioner can be used to specify a particular value or threshold of parameters for which the analyzer 314 generates and provides treatment analytics for the patients suffering from same or similar type of diseases. The physician can be able to specify the rules and corresponding levels for generating treatment analytics for the benefit of the medical practitioners, the patient, or any other user. In an embodiment, the medical practitioner input can allow entry of medical practitioner-established rules to analyze the medical information received from various sources. For example, the medical practitioner may instruct that an analytic is generated and treatment is recommended upon detecting a particular condition (for instance, blood pressure change in excess of a particular value). In an embodiment, the patient input can include an interface, a data entry device, a proxy device, and the like accessible by the patient or any other user. Exemplary data entry devices include keyboard, mouse, trackball, controller, microphone, touch-sensitive screen, removable media storage device, PDA, or any other device for providing data to the analyzer 314. Using the patient input, a user can be able to enter data corresponding to real time or earlier observations of the patient. In one example, the patient input can include a PDA executing a program to allow the patient to enter data such as food intake, exercise activity, perceived sensations, symptoms, posture information, and the like. The data from the PDA, or other patient input device, can be transferred to analyzer 314 by a wired or wireless connection. Further, the patient input, as with medical practitioner input, can include a data entry terminal, such as to provide the input information individually, simultaneously, parallelly, randomly, or a combination thereof.

In an embodiment, the patient's historic data described herein can include an interface configured to receive information including, for example, patient EMR, clinical information system (CIS) data, or other data corresponding to a particular patient. Exemplary data includes family medical history, immunization records, patient vital signs, trends, and any other historical medical and clinical data associated with the patients. In an embodiment, the hospital or clinic information systems, bedside computer, or any other device can include details concerning to the patient's medical historic data. In an embodiment, the pharmaceutical databases described herein can include data correlating specific drugs with medical conditions and symptoms, data generated based on research corresponding to specific geographical regions of the world, data indicating population pharmaco-kinetics for different drugs, data about the drug therapy for a particular patient, and the like. The data included, for example, correlates the effects of a drug as a function of time after taking the drug. In an embodiment, the population/clinical data described herein can include data from different health care exchange organisations, hospitals, laboratories, clinical studies for a particular population and the like, associated with the patient suffering from same or substantially similar type of diseases. Further, the population/clinical can include data indicating relationships between selected drugs. For example, population/clinical data can include normative and statistical data showing relationships between populations and particular drugs. In an embodiment, the analyzer 314 can be configured to associate with a large population of various data sources, such as to receive medical information associated with the plurality of patients. In an embodiment, the analyzer 314 can be configured to include analysis tools implementing various analysis functions, algorithms, logics, variables, instructions, conditions, criteria, rules, and the like, such as to analyze the information received from the various sources. Further, the analyzer 314 can be configured to generate analytics for the medical information associated with the plurality of patients suffering from same (or substantially similar) type of diseases. In an embodiment, the analytics generated by the analyzer 314 can include for example, but not limited to, heart disease analytics, diabetes analytics, influenza analytics, stroke analytics, obesity analytics, tuberculosis analytics, menstrual analytics, cancer patterns analytics, chronic lower respiratory diseases analytics, alzheimer's disease analytics, pneumonia analytics, nephritis analytics, nephrotic syndrome analytics, nephrosis analytics, and the like. The analytics described herein can be configured to provide the information related to the treatments provided to the maximum number of patients suffering from the same (or substantially similar) type of diseases, characteristics, habits, likes, dislikes, and the like.

In addition to clinical grade patient data, a health repository can receive daily updates from fitness devices (watches, instrumented clothing, footwear for activity indication, sleep monitoring equipment, among others). The sensors can monitor mental acuity using sensors such as EEG sensors or other daily stress sensors. Similar fitness data from the phone can be captured in the health repository. In addition, the phone can capture communications reflective of the patient's mental health by analyzing spatial communications with the user such as emails and social network postings when linked with variations in geospatial activity, sleep duration. Additionally, other information such as purchases from restaurants and grocery stores can be used to analyze the calorie consumption by the subject. Data from an insurance claims repository and the payor (such as the employer payor) can be used to validate the EHR records. The data is provided to a learning module to create medical models for each patient/subject. A classifier is generated by the learning module, and the classifier can receive new EHR and fitness data and generate output for a prediction engine. The prediction engine in turn provides patient health predictions based on data mining, classification and prediction that correlate phenotypes with gene functions, identify signatures and landscapes of disorders, and infer correlative versus causative patterns. The system includes a scheduling application that is programmed or otherwise configured to receive data from sensors and medical data from doctors and hospitals, and to provide patient-procedure data from each request to a prediction scoring engine. The system also receives data from a plurality of tests over a period of time. Alternatively, a number of tests can be conducted within the same time period, and such data can be processed to detect if a medical condition has improved or deteriorated. The prediction scoring engine includes a plurality of prediction models generated and maintained/updated by the by learning module (in this example 3: Naïve Bayes, logistics regression, and neural network prediction models). The prediction engine effectively operates as an analysis database in which data mining predictions are performed. In operation, the received or "target" patient-procedure data is processed through each of the models, and given a score. A comparator module then analyzes each score from the three models to determine if the predictions are in agreement. For instance, the comparator module can be programmed or otherwise configured to determine if each score is above a predetermined threshold (after normalization of scores). If two or three of the three predictions agree based on this determination, then a corresponding set of procedure parameters (e.g., procedure location, procedure equipment, and procedure personnel/technician) from the matched models are provided to the scheduling application, and the patient is predictively scheduled for that procedure. Otherwise, if the predictions disagree, then not prediction is made. In such a case, a manual scheduling procedure can be used. In other embodiments, in addition to or in lieu of the 3 learning modules discussed above, the machine learning system can be a supervised or unsupervised learning method such as support vector machine, random forest, nearest neighbor analysis, linear regression, binary decision tree, discriminant analyses, logistic classifier and cluster analysis, among others. When the patient visits the doctor, the progress or failure in the treatment can be reviewed, and the system can make recommendations on ways to improve the treatment based on the totality of data received for the patient and from a population of similar patients. For example, based on genetic tests, if treatments for a particular disease is working, then the system schedules the patient for more of the same treatment type. However, if the tests indicate that the treatment is not effective, then the system brings the patient in ahead of planned doctor visit and recommends alternative treatment in view of research data, FDA clinical trial results for drugs treating the same disease, and population treatment data showing other successful treatments for the disease, among others.

Figure 15E:
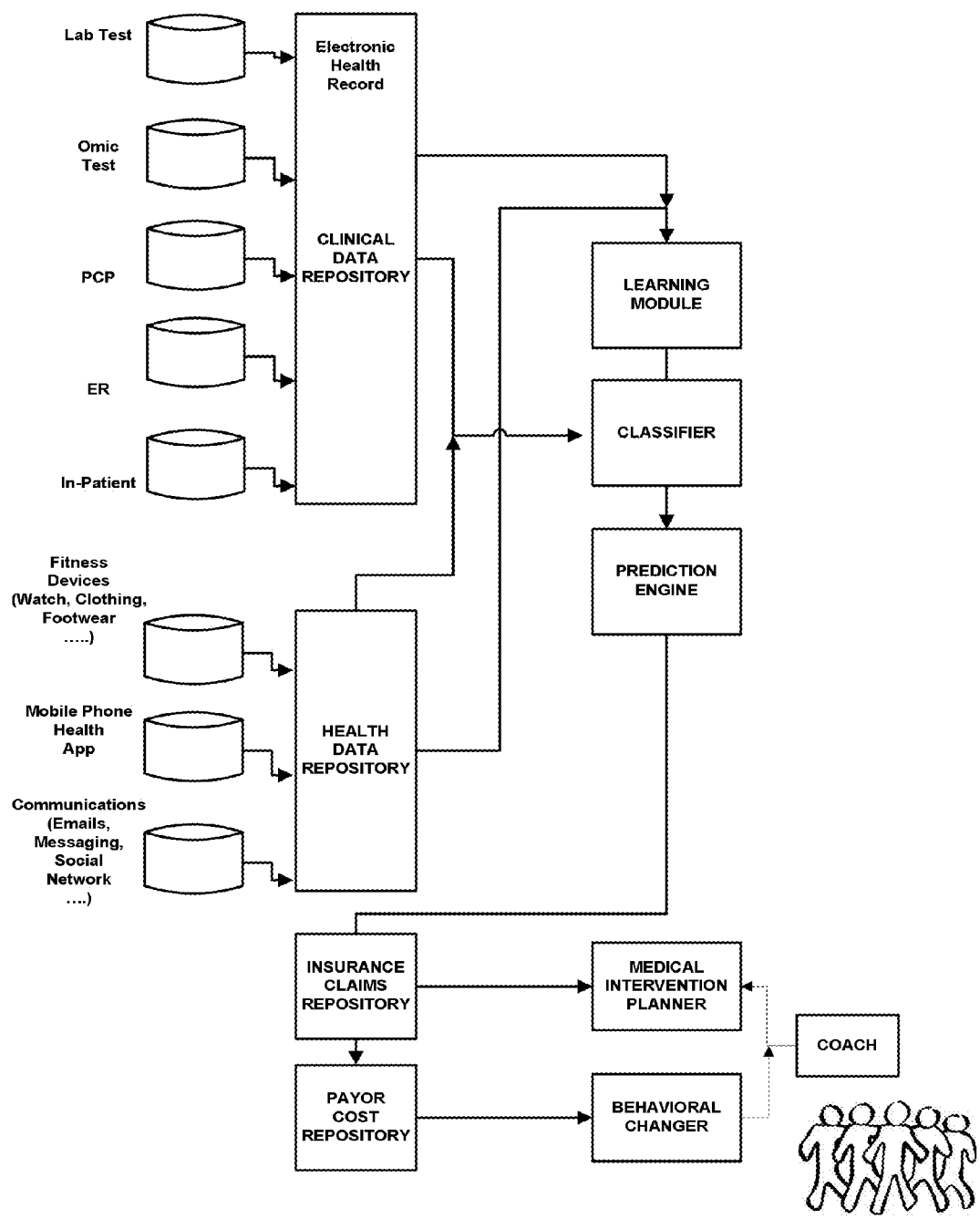

FIG. 15E shows an exemplary system for mining health data for precision medicine. In this system, lab test equipment generates data that is stored in a database. Omic test equipment also generates data that is stored in another database. MR data from primary care physician (PHP), emergency room physicians (ER), and in-patient care data is also stored in a database. These databases form a clinical data repository that contains medical diagnosis and treatment information. The clinical data is high grade medical information that is secured by patient privacy laws such as HIPPA. One exemplary process for improving healthcare using precision medicine includes:

a. obtain clinical data from laboratory test equipment
b. obtain clinical data from one or more omic test equipment
c. obtain clinical data from a primary care physician database
d. obtain clinical data from a specialist physician database
e. obtain clinical data from an emergency room database
f. obtain clinical data from an in-patient care database
g. save the clinical data into a clinical data repository
h. obtain health data from fitness devices and from mobile phones
i. obtain behavioral data from social network communications and mobile device usage patterns
j. save the health data and behavioral data into a health data repository separate from the clinical data repository
k. mine the clinical data repository and health data repository for patients sharing similarity with the subject, including one or more similar biomarkers associated with health conditions l. identify at least one similar health conditions and identifying one or more corrective actions recorded in the repository and the result of each action for the one or more health conditions;

m. present the corrective action and result to the subject and recommending an action to reduce risk from the predicted health condition n. monitor the health condition using updates in the clinical data repository and health data repository In another embodiment for cost effective health maintenance, the system includes a method of insuring a subject for cancer, by:

a. enrolling the subject into a cost-saving program;

b. receiving a body sample during routine periodic examinations and characterizing the subject's omic information with a DNA sequencer; and c. using historical omic information to detect an occurrence of a disease such as cancer before the subject is suspected of having the disease; and d. proactively recommending early treatments based on the omic information received at each time interval to cost-effectively control disease.

In an exemplary process to analyze cell-free DNA samples, the process can detect cancerous or diseased DNA fragments in urine, saliva, sweat or blood. First, DNA samples such as saliva or urine with cell-free DNA materials are acquired. The cell-free DNA double hexlix strands are split and non-unique barcodes are added to each strand to track DNA sample to avoid result mismatching in large scale sequencing. The result is then amplified and enriched for predetermined gene panels. After amplification, the strands are sequenced and the bar code in each of the complementary strand is used to recover the original gene sequence and to minimize errors in preparation, sequencing, or damage in the DNA during the process and improve the signal to noise ratio significantly when looking for certain protein or gene in liquid biopsy. A probability model can be applied to recover the correct gene information for diagnosis. FIG. 4E shows exemplary probabilistic signal processing techniques. The system can then check with genetic libraries for presence of problematic genes and a report can be generated.

Another aspect includes diagnosing a subject for one or more diseases by:

a. receiving a body sample during routine periodic examinations and characterizing the subject's genetic information with a DNA sequencer; and b. using the information to detect cell death in vivo;

c. predicting a disease based on excessive or insufficient in vivo cell death.

Yet another aspect includes diagnosing a subject for a disease by a. receiving urine from the subject and characterizing the subject's genetic information with a DNA sequencer; and b. using the information to detect an occurrence of the disease.

Another method of diagnosing a subject for a disease by:

a. receiving saliva from the subject and characterizing the subject's genetic information with a DNA sequencer; and b. using the information to detect an occurrence of cancer.

7. Yet another method of diagnosing a subject for cervical cancer includes:

a. receiving a body sample during routine periodic examinations and characterizing the subject's genetic information at two or more time intervals with a DNA sequencer; and b. detecting one or more sequences of the E1 gene of HPV and indicating cancer from human papillomavirus.

Another method of diagnosing an infant subject includes a. receiving a body sample during routine periodic examinations;

b. assaying for the presence of a sequence of fetal polymeric DNA in the body sample that differs from a DNA of a maternal genome;

c. characterizing the subject's genetic information over a predetermined period with a DNA sequencer; and d. using the information to detect an occurrence of cancer before the subject is suspected of having cancer.

In an exemplary emotion and mental health mapping to omic states system, the process detects, acquires and/or processes user information including physiological and non-physiological data associated with user. The process detects and obtains user's physiological and non-physiological data via one or more sensors and other devices (e.g., a camera, a microphone, text messages, emails, social networks) that are associated with user. Emotion determination may be done using a processor to preprocess and transform the user information, and use one or more machine learning techniques (e.g., SVM technique) to process the transformed data to determine the emotional state which may include happiness, sadness, anxiety, excitement, boredom, fear, indifference, calmness, anger, aggressiveness, disgust, surprise, anticipation, and/or other known emotions or emotional states. An emotion reporting unit receives the emotional state of user from emotion determination unit, and requests a confirmation from user to communicate or share the emotional state. If emotion reporting unit receives the confirmation, emotion reporting unit communicates data including the emotional state to an application(s) functional on user device(s) associated with or operated by user and to omic correlation unit. An application functional on the user device(s) may be a social-networking application (e.g., Facebook, Twitter, LinkedIn, Google+, etc.) which the user is authorized to access as a member thereof. Accordingly, as part of communicating the emotional state of the user, emotion reporting unit 130 may, among other operations, provide a message including an indication of the determined emotional state of the user to be shared with other members (e.g., "friends," "followers," "connections," etc.) of the application, or provide a SMS message or an email message, e.g., to a predetermined set of recipients listed in an address book at the user device(s). Emotional states of the user can be tracked based on one or more tracking criteria, e.g., user's past locations, for a past time period, browsing history, etc. Emotion history unit may then process the emotional states to determine an effect on the user caused due to the emotional states relative to the tracking criterion. Emotion history unit may also be able to provide preventive strategies, or automatically alter the user's itinerary to improve mood (e.g., change the default driving navigation plan or reschedule a typically stressful meeting to a better time of day for the user). The detected emotion states are correlated with omics data during the relevant time. One embodiment maps the emotion states to functional variants at five genes: catechol-O-methyltransferase (COMT), serotonin transporter (SLC6A4), neuropeptide Y (NPY), a glucocorticoid receptor-regulating co-chaperone of stress proteins (FKBP5) and pituitary adenylate cyclase-activating polypeptide receptor (ADCYAP1R1). These represent a range of effects of genes on emotion as well as the variety of mechanisms and factors, such as stress, that modify these effects. Another embodiment maps the emotion states to the serotonin transporter gene (5-HTT) and a polymorphic serotonin-transporter-linked polymorphic region (5-HTTLPR) which determine the quantity and duration of serotonin synaptic signaling during neurotransmission. There are three important variants of 5-HTTLPR alleles: the short (S) allele, the long-rs25531(G) (La) allele, and the long-rs25531(A) (La) allele. The short (S) allele and the long-rs25531(G) (Lg) allele carriers compared to the long-rs25531(A) (La) allele variant carriers, have lower mRNA transcriptions of the serotonin transporter. Individuals without an La allele are found to produce approximately 50% less mRNA than individuals carrying homozygous La alleles. This polymorphism has been shown to correlate with the severity of affect reactivity and mood dysregulation.

In an embodiment, the system 100 can be configured to analyze the data received from the various electronic sources and can address various heart diseases and treatments provided to the patients suffering from same or substantially similar type of the heart diseases. The heart disease analytics 600 shows the different type of heart diseases such as for example, but not limited to, atrial flutter, atrial fibrillation (AF), supraventricular tachycardia (SVT), ventricular tachycardia (VT), premature contraction (PC), ventricular fibrillation (VF), and the like, and the treatments provided to the majority of patients having similar or same type of the heart disease. For example, the analytics data shows more than 100 patients are provided the treatment-1 to the patients suffering from atrial flutter. Similarly, more than 250 patients are provided the treatments 1 and 3 to the patients suffering from the VT. Further, the heart disease analytics data can be presented to the medical practitioners 206 and 208 using the remote computer 102. The medical practitioners can use the heart disease analytics data to provide the heart disease treatments to the patients suffering from same or substantially similar type of the heart diseases. For example, if a patient is suffering from the SVT heart disease then the medical practitioners 206 and 208 can use the analytics data (indicating that more than 200 patients are provided the treatment-3 for the SVT type of heart disease) to provide treatment recommendation for the patient. Similarly, if a patient is suffering from the PC heart disease then the medical practitioners 206 and 208 can use the analytics 600 data (indicating that more than 200 patients are provided treatment-3 for the PC type of heart diseases) to provide treatment recommendation for the patient. In an embodiment, the system 100 can be configured to analyze the data received from the various electronic sources (such as described in the FIG. 4). The FIG. 7 shows the analytics data generated for origin of VT and treatments provided to the patients suffering from same or substantially similar type of the VT diseases. The origin of VT analytic data 600 shows the origin of arrhythmia at different location of the heart such as for example, but not limited to, left ventricle (LV), right ventricle (RV), left atrium (LA), right atrium (RA), sino-atrial node (SA), and the appropriate treatments provided to the majority of patients based on the location of the origin of VT. For example, more than 150 patients are provided the treatment-2 for the VT originating from the RV location of the heart. Similarly, proximately 200 patients are provided the treatments 2 and 3 or the VT originating from the LA location of the heart. Further, the heart disease analytics can be presented to the medical practitioners using the remote computer 102. The medical practitioners 206 and 208 can use the origin of VT analytics data to provide the appropriate treatments to the patients suffering from arrhythmia starting from same or substantially similar type of heart location. For example, if a patient is suffering from the VT heart disease then the medical practitioners can use the analytics 700 data (indicating that more than 250 patients is provided the treatment-7 for the VT originating from the LA) to provide the treatment recommendation for the patient. Similarly, if a patient is suffering from the VT then the medical practitioners can use the analytics 600 data (indicating that more than N patients is provided the treatment-N for the VT originating from the SA) to provide the treatment recommendation for the patient.

In an embodiment, the system 100 can be configured to analyze the data received from the various electronic sources for the obesity and treatments provided to the patients suffering from same or substantially similar type of weight. The obesity analytics data shows the body mass index (BMI) such as for example, but not limited to, 20, 25, 30, 35, 40, 45, and the like, and the treatments provided to the majority of patients having similar or same type of the BMI. For example, patients are provided the treatment-1 for the patients having the BMI as 25. Similarly, patients are provided the treatments-6 for the patients having the BMI as 40. Further, the obesity analytics data can be presented to the medical practitioners 206 and 208 using the remote computer 102. The medical practitioners 206 and 208 can use the obesity analytics data 800 to provide the obesity treatments to the patients suffering from same or substantially similar BMI. For example, if a patient is having the BMI as 35 then the medical practitioners 206 and 208 can use the analytics data (indicating that more than 200 patients (having the BMI as 35) are provided the treatment-3 and 5) to provide treatment recommendation for the patient. Similarly, if a patient is having the BMI as 45 then the medical practitioners 206 and 208 can use the analytics data (indicating that more than 150 patients (having the BMI as 45) are provided the treatment-N) to provide treatment recommendation for the patient. Similarly, data can be generated for various blood sugar level and treatments provided to the patients suffering from same or substantially similar level of diabetes. The diabetes disease analytic data 900 shows the different levels of blood sugar (for both men and women) such as for example, but not limited to, 50, 100, 150, 200, 250, and the like, and the treatments provided to the majority of patients having similar or same levels of diabetes. For example, more than 300 patients (men's) are provided the treatment-3 for blood sugar level 100. Similarly, more than 200 patients (women's) are provided the treatments 2 and 5 for blood sugar level 100. Further, the diabetes analytics 900 can be presented to the medical practitioners 206 and 208 using the remote computer 102. The medical practitioners 206 and 208 can use the diabetes analytics data to provide the diabetes treatments to the patients suffering from same or substantially similar level of blood sugar. For example, if a patient (men) is having a blood sugar level 150 then the medical practitioners 206 and 208 can use the analytics 900 data (indicating that more than 250 patients (men's) are provided the treatment-7&3 for the blood glucose level 150) to provide treatment recommendation for the patient. Similarly, if a patient (women) is having a blood sugar level 150 then the medical practitioners 206 and 208 can use the analytics 900 data (indicating that more than 300 patients (women's) are provided the treatment-10 for the blood glucose level 150) to provide treatment recommendation for the patient.

One exemplary data flows between a user with a cell phone or mobile device in an interactive conversation with third party devices or doctors is discussed next. A patient is first registered with the system. After the user enrolls, the system starts communicating with the patient by sending the patient one or more instructions and/or reminders. Using a computer such as a mobile device the user communicates with the physician communicator engine and receives in return a custom response. At the same time, and depending on selected rules triggered by the patient response, the system sends notifications to third-party devices such as devices owned by family members or caregivers. The system can also send notifications to doctors, doctor's staff, or other authorized service providers who then send in response results that are automatically processed by the system to alter the behavior of some rules.

Next is an exemplary process for automated interactive communication between clinicians and patients. The process includes code to:
Set up rules for treatment modalities and assign zero or more rules to agent (1)
  Enroll patient and assign treatment modality to patient (2)
  During run time:
    receiving communications from patients and selecting zero or more agents to respond to the communication (4)
    receiving at zero or more event handlers messages from the zero or more responsive agents and formats the messages for a target device (6)

Another exemplary process for applying the agents to a weight loss treatment scenario. The general goals of weight loss and management are: (1) at a minimum, to prevent further weight gain; (2) to reduce body weight; and (3) to maintain a lower body weight over the long term. The initial goal of weight loss therapy is to reduce body weight by approximately 10 percent from baseline. If this goal is achieved, further weight loss can be attempted, if indicated through further evaluation. A reasonable time line for a 10 percent reduction in body weight is 6 months of therapy. For overweight patients with BMIs in the typical range of 27 to 35, a decrease of 300 to 500 kcal/day will result in weight losses of about ½ to 1 lb/week and a 10 percent loss in 6 months. For more severely obese patients with BMIs >35, deficits of up to 500 to 1,000 kcal/day will lead to weight losses of about 1 to 2 lb/week and a 10 percent weight loss in 6 months. Weight loss at the rate of 1 to 2 lb/week (calorie deficit of 500 to 1,000 kcal/day) commonly occurs for up to 6 months. After 6 months, the rate of weight loss usually declines and weight plateaus because of a lesser energy expenditure at the lower weight.

Dietary Therapy: A diet that is individually planned and takes into account the patient's overweight status in order to help create a deficit of 500 to 1,000 kcal/day should be an integral part of any weight loss program. Depending on the patient's risk status, the low-calorie diet (LCD) recommended should be consistent with the NCEP's Step I or Step II Diet. Besides decreasing saturated fat, total fats should be 30 percent or less of total calories. Reducing the percentage of dietary fat alone will not produce weight loss unless total calories are also reduced. Isocaloric replacement of fat with carbohydrates will reduce the percentage of calories from fat but will not cause weight loss. Reducing dietary fat, along with reducing dietary carbohydrates, usually will be needed to produce the caloric deficit needed for an acceptable weight loss. When fat intake is reduced, priority should be given to reducing saturated fat to enhance lowering of LDL-cholesterol levels. Frequent contacts with the practitioner during dietary therapy help to promote weight loss and weight maintenance at a lower weight.

An increase in physical activity is an important component of weight loss therapy, although it will not lead to substantially greater weight loss over 6 months. Most weight loss occurs because of decreased caloric intake. Sustained physical activity is most helpful in the prevention of weight regain. In addition, it has a benefit in reducing cardiovascular and diabetes risks beyond that produced by weight reduction alone. For most obese patients, exercise should be initiated slowly, and the intensity should be increased gradually. The exercise can be done all at one time or intermittently over the day. Initial activities may be walking or swimming at a slow pace. The patient can start by walking 30 minutes for 3 days a week and can build to 45 minutes of more intense walking at least 5 days a week. With this regimen, an additional expenditure of 100 to 200 calories per day can be achieved. All adults should set a long-term goal to accumulate at least 30 minutes or more of moderate-intensity physical activity on most, and preferably all, days of the week. This regimen can be adapted to other forms of physical activity, but walking is particularly attractive because of its safety and accessibility. Patients should be encouraged to increase "every day" activities such as taking the stairs instead of the elevator. With time, depending on progress and functional capacity, the patient may engage in more strenuous activities. Competitive sports, such as tennis and volleyball, can provide an enjoyable form of exercise for many, but care must be taken to avoid injury. Reducing sedentary time is another strategy to increase activity by undertaking frequent, less strenuous activities.

The communication system is used to provide Behavior Therapy. The system automatically sends messages using rule-based agents to communicate with patients. The agents can use learning principles such as reinforcement provide tools for overcoming barriers to compliance with dietary therapy and/or increased physical activity to help patient in achieving weight loss and weight maintenance. Specific communication message include self-monitoring of both eating habits and physical activity, stress management, stimulus control, problem solving, contingency management, cognitive restructuring, and social support through the social network system.

Pharmacotherapy can be used if behavior therapy does not work. In carefully selected patients, appropriate drugs can augment LCDs, physical activity, and behavior therapy in weight loss. Drugs such as sibutramine and orlistat can be used as long as potential side effects with drugs are considered. With sibutramine, increases in blood pressure and heart rate may occur. Sibutramine should not be used in patients with a history of hypertension, CHD, congestive heart failure, arrhythmias, or history of stroke. With orlistat, fat soluble vitamins may require replacement because of partial malabsorption. Weight loss surgery is one option for weight reduction in a limited number of patients with clinically severe obesity, i.e., BMIs >=40 or >=35 with comorbid conditions. Weight loss surgery should be reserved for patients in whom efforts at medical therapy have failed and who are suffering from the complications of extreme obesity. Gastrointestinal surgery (gastric restriction [vertical gastric banding] or gastric bypass is an intervention weight loss option for motivated subjects with acceptable operative risks. An integrated program must be in place to provide guidance on diet, physical activity, and behavioral and social support both prior to and after the surgery.

The agents are adaptive to the patient and allow for program modifications based on patient responses and preferences. For example, the agent can be modified for weight reduction after age 65 to address risks associated with obesity treatment that are unique to older adults or those who smoke.

The event handler can be coded to:
Receive message from patient or doctor (20)
Determine user treatment modality (22)
  For each modality
    Determine relevant rules (26)
    For each rule Determine responsive agent(s) (30)
For each agent
Execute agent program (34)
Get input from service provider if needed (36)
Format & send the message for the patient's mobile device (38)

The system processes a communication from a patient according to one or more treatment scenarios. Each treatment scenario is composed of one or more rules to be processed in a sequence that can be altered when invoking certain agents.

The if then rules can be described to the system using a graphical user interface that runs on a web site, a computer, or a mobile device, and the resulting rules are then processed by a rules engine. In one embodiment, the if then rules are entered as a series of dropdown selectors whose possible values are automatically determined and populated for user selection to assist user in accurately specifying the rules.

In one embodiment, the rules engine is Jess, which is a rule engine and scripting environment written entirely in Sun's Java language by Ernest Friedman-Hill at Sandia National Laboratories in Livermore, Calif. and downloadable at http://www.jessrules.com/jess/index.shtml. With Jess, the system can "reason" using knowledge supplied in the form of declarative rules. Jess is small, light, and one of the fastest rule engines available. The user can dynamically create an if/then/else statement. A dropdown selector can be used to select a column, then a dropdown to select the conditional operator (=, >, <, !=, among others) and then a text box in which to enter a column, text or number value. The system can add multiple conditions. The rules can be saved as serialized object in a database. After entering parameter values, a new set of rules can be generated and inserted within the current active scenario. The corresponding rules can then be modified directly by accessing the individual agents within the rules.

In one embodiment, the agent can be self-modifying. The agent receives parameters from its callers. The agent in turn executes one or more functions. It can include an adaptive self-modifying function, and the third-party extension interfaces. The adaptive self-modifying function is capable of modifying the agent parameters and/or the agent function at run time, thereby changing the behavior of the agent.

An exemplary modality of the rules engine can be used to serve obese patients that the doctor can review and approve. In this scenario, the engine executes 3 master agents: blood pressure master agent (50), diabetic master agent (52), and weight loss agent (54). The blood pressure master agent in turn invokes the following agents:

If blood pressure is between 130-139/85-89 mm Hg then run agent high_blood_pressure. If blood pressure is between 140-159/90-99 mm Hg then run agent stage1_blood_pressure. If blood pressure is above 159/99 mm Hg then run agent drug_treatment_for_blood_pressure For the above example, high normal blood pressure of between 130-139/85-89 mm Hg is included in the risk stratification. In patients with high normal blood pressure with no or only one concurrent risk factor that does not include diabetes, target organ, or clinical cardiac disease, the agent high_blood_pressure suggests to the patient to use lifestyle modification to lower blood pressure. Lifestyle modification includes changes to the patient's dieting and exercising habits. With a risk factor of target organ or clinical cardiac disease, diabetes and/or other risk factors, the agent can recommend drug therapy, no matter what the patient's blood pressure is. The agent for patients with stage 1 blood pressures of between 140-159/90-99 mm Hg who have no other risk factors will suggest the patient try lifestyle modifications for a year before drug therapy is used. But if these patients have one risk factor other than diabetes, target organ, or clinical cardiac disease, their lifestyle modification should be tried for only 6 months before initiation therapy. For patients with blood pressure above 150/100 mm Hg, the agent reminds the patient to have drug therapy in addition to lifestyle modifications.

The diabetic master agent in turn invokes the following agents:
Monitoring agent: Make sure doctor orders the key tests at the right times.
Dieting planning agent: Work with a dietitian to develop a great eating plan.
Glucose Testing Agent: Check blood glucose at correct intervals.
Exercise agent: Monitor exercise to help heart.
Medication compliance agent: check that insulin is taken at correct time.
Foot care agent: Check your feet with your eyes daily.
Eye care agent: remind patient to get periodic eye exam.

The weight loss agent considers the patient's BMI, waist circumference, and overall risk status including the patient's motivation to lose weight. The weight loss agent in turn call the following agents:

Body Mass Index agent: The BMI, which describes relative weight for height, is significantly correlated with total body fat content. The BMI should be used to assess overweight and obesity and to monitor changes in body weight. In addition, measurements of body weight alone can be used to determine efficacy of weight loss therapy. BMI is calculated as weight (kg)/height squared (m2). T Waist Circumference agent: The presence of excess fat in the abdomen out of proportion to total body fat is an independent predictor of risk factors and morbidity. Waist circumference is positively correlated with abdominal fat content. It provides a clinically acceptable measurement for assessing a patient's abdominal fat content before and during weight loss treatment. The sex-specific cutoffs noted on the next page can be used to identify increased relative risk for the development of obesity-associated risk factors in most adults with a BMI of 25 to 34.9 kg/m2: These waist circumference cutpoints lose their incremental predictive power in patients with a BMI >=35 kg/m2 because these patients will exceed the cutpoints noted above.

These categories denote relative risk, not absolute risk; that is, relative to risk at normal weight. They should not be equated with absolute risk, which is determined by a summation of risk factors. They relate to the need to institute weight loss therapy and do not directly define the required intensity of modification of risk factors associated with obesity.

Risk Status agent is used for assessment of a patient's absolute risk status and in turn uses the following agents: Disease condition agent: determine existence of coronary heart disease (CHD), other atherosclerotic diseases, type 2 diabetes, and sleep apnea; Obesity-associated disease agent: determines gynecological abnormalities, osteoarthritis, gallstones and their complications, and stress incontinence.

Cardiovascular risk factors agent: cigarette smoking, hypertension (systolic blood pressure >=140 mm Hg or diastolic blood pressure >=90 mm Hg, or the patient is taking antihypertensive agents), high-risk LDL-cholesterol (>=160 mg/dL), low HDL-cholesterol (<35 mg/dL), impaired fasting glucose (fasting plasma glucose of 110 to 125 mg/dL), family history of premature CHD (definite myocardial infarction or sudden death at or before 55 years of age in father or other male first-degree relative, or at or before 65 years of age in mother or other female first-degree relative), and age (men >=45 years and women >=55 years or postmenopausal). Patients can be classified as being at high absolute risk if they have three of the aforementioned risk factors. Patients at high absolute risk usually require clinical management of risk factors to reduce risk. Patients who are overweight or obese often have other cardiovascular risk factors. Methods for estimating absolute risk status for developing cardiovascular disease based on these risk factors are described in detail in the National Cholesterol Education Program's Second Report of the Expert Panel on the Detection, Evaluation, and Treatment of High Blood Cholesterol in Adults (NCEP's ATP II) and the Sixth Report of the Joint National Committee on Prevention, Detection, Evaluation, and Treatment of High Blood Pressure (JNC VI). The intensity of intervention for cholesterol disorders or hypertension is adjusted according to the absolute risk status estimated from multiple risk correlates. These include both the risk factors listed above and evidence of end-organ damage present in hypertensive patients. Approaches to therapy for cholesterol disorders and hypertension are described in ATP II and JNC VI, respectively. In overweight patients, control of cardiovascular risk factors deserves equal emphasis as weight reduction therapy. Reduction of risk factors will reduce the risk for cardiovascular disease whether or not efforts at weight loss are successful.

Other risk factors can be considered as rules by the agent, including physical inactivity and high serum triglycerides (>200 mg/dL). When these factors are present, patients can be considered to have incremental absolute risk above that estimated from the preceding risk factors. Quantitative risk contribution is not available for these risk factors, but their presence heightens the need for weight reduction in obese persons. One embodiment determines high interest disease- and drug-related variants in the patient's genome and identifies top diseases with the highest probabilities. For each disease, the system determines the pretest probability according to the patient age, gender, and ethnicity. The system then determines the independent disease-associated SNVs used to calculate the subject's disease probability. For each disease, for example type 2 diabetes, the system determines probability using independent SNVs, a likelihood ratio (LR), number of studies, cohort sizes, and the posttest probability. Blood pressure and blood glucose trend measurements are also determined.

A patient motivation agent evaluates the following factors: reasons and motivation for weight reduction; previous history of successful and unsuccessful weight loss attempts; family, friends, and work-site support; the patient's understanding of the causes of obesity and how obesity contributes to several diseases; attitude toward physical activity; capacity to engage in physical activity; time availability for weight loss intervention; and financial considerations. In addition to considering these issues, the system can heighten a patient's motivation for weight loss and prepare the patient for treatment through normative messaging and warnings. This can be done by enumerating the dangers accompanying persistent obesity and by describing the strategy for clinically assisted weight reduction. Reviewing the patients' past attempts at weight loss and explaining how the new treatment plan will be different can encourage patients and provide hope for successful weight loss.

In some embodiments, the data processing system is coupled with equipment that determines an organism's genotype from an in-vitro sample obtained from the organism. In other embodiments, the genotypes are determined elsewhere and the data processing system may obtain data representative of the genotype via any of its data interfaces.

One exemplary sensor communicating with one of the interfaces 115-135 receives a biologic sample from an individual such as a bodily fluid (such as urine, saliva, plasma, or serum) or feces or a tissue sample (such as a buccal tissue sample or buccal cell). The biologic sample can then be used to perform a genome scan. For example, DNA arrays can be used to analyze at least a portion of the genomic sequence of the individual. Exemplary DNA arrays include GeneChip Arrays, GenFlex Tag arrays, and Genome-Wide Human SNP Array 6.0 (available from Affymetrix, Santa Clara, Calif.). In other examples, DNA sequencing with commercially available next generation sequencing (NGS) platforms is generally conducted: DNA sequencing libraries are generated by clonal amplification by PCR in vitro; then the DNA is sequenced by synthesis, such that the DNA sequence is determined by the addition of nucleotides to the complementary strand rather through chain-termination chemistry; next, the spatially segregated, amplified DNA templates are sequenced simultaneously in a massively parallel fashion without the requirement for a physical separation step. For microbiome analysis, cotton swabs are applied to forehead, behind ears, nose, among others, and fecal samples are analyzed using DNA sequencing machines. In certain embodiments, whole or partial genome sequence information is used to perform the genome scans. Such sequences can be determined using standard sequencing methods including chain-termination (Sanger dideoxynucleotide), dye-terminator sequencing, and SOLiD™ sequencing (Applied Biosystems). Whole genome sequences can be cut by restriction enzymes or sheared (mechanically) into shorter fragments for sequencing. DNA sequences can also be amplified using known methods such as PCR and vector-based cloning methods (e.g., *Escherichia coli*).

In some embodiments, at least a portion of an individual's genetic material (e.g., DNA, RNA, mRNA, cDNA, other nucleotide bases or derivative thereof) is scanned or sequenced using, e.g., conventional DNA sequencers or chip-based technologies, to identify the presence or absence of one or more SNPs or CNPs or copy number polymorphisms ("CNPs") and their corresponding alleles. One embodiment performs exome sequencing (also known as Whole Exome Sequencing or WES), which is a technique for sequencing all the protein-coding genes in a genome (known as the exome). It consists of first selecting only the subset of DNA that encodes proteins (known as exons), and then sequencing that DNA using any high throughput DNA sequencing technology. There are 180,000 exons, which constitute about 1% of the human genome, or approximately 30 million base pairs. Exome data relates with genetic variation that is responsible for both Mendelian and common diseases such as Miller syndrome and Alzheimer's disease without the high costs associated with whole-genome sequencing.

The sensors can also include fitness sensors such as wearable watches/clothing/shoes that monitor activity, heart rate, ECG, blood pressure, blood oxygen level, among others. The sensors 115-135 can also detect purchase activities and on-line activities that reflect the user's health habits. For example, the sensors can be a data feed that picks up data relating to grocery purchases, food expenses, restaurant spending In yet other examples, the sensors can be sensors in a phone. For example, in depression sensor, the phone can detect a person's activity and correlate to depression: people who stuck to a regular pattern of movement tended to be less depressed as people with mental health problems in general have disrupted circadian rhythms and a depressed mood may pull a user off her routine. Depressed people also spends more time on their phones or browsing aimlessly, as depressed people tend to start avoiding tasks or things they have to do, particularly when they're uncertain. In addition to sensor captured healthcare data, healthcare data refers to any data related or relevant to a patient. Healthcare data may include, but is not limited to, fitness data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives. In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted. One embodiment uses local storage on the mobile phone of data collected by other devices and an app is provided to interpret sensor data. The phones have fingerprint sensor security, and the mobile app is the point of aggregation for all the user's different health data. The health data is captured by the footwear and also by third party sensors (Nike+, Withings Scale, Fitbit Flex etc) and tie data from all fitness hardware into a cohesive whole. In one embodiment, sensors in the clothing or shoes or worn by the user can communicate with a mobile phone and transmit user activity or inactivity to networks that allow information access and provide support on the back end. Having a network or backbone that a much broader population base can seamlessly connect to will fuel more meaningful data comparisons and analysis and distill useful information. The network can then aggregate data from the footwear with other health information—data from across a certain geography or specific diagnosis, for example—to create a more complete picture of group health. Creating healthcare communities from which to collect data is a way to crowd source valuable healthcare information. By bringing together people with a common interest such as weight loss, the footwear devices serve as a mechanism to build engagement and at the same time compile information. In one embodiment, the information is used by health payors or insurers to prompt patients to change their lifestyles. The more employers, insurance companies, or healthcare payors know about a population's health, the more steps they can take to keep them healthy. For instance, patient data entered into electronic health records at practices and hospitals could reveal allergies, health histories, and medication use. Combined with information collected through the footwear, providers will have more complete and essentially real-time data to treat and manage the health of individual patients, as well as patient populations. The cumulative sum of data captured from many individuals about a health condition or population can be used to move the population to healthier conditions. In one embodiment, health plans can offer incentives to members willing to sign up for designated footwear health programs and join in a "game" to be fit. The system reduces healthcare costs by identifying trends and commonalities among certain populations—thereby enabling better preventive care. In addition to engaging patients and aiding personal wellness, they can move healthcare beyond individual monitoring and treatment toward more effective population health management. By engaging and empowering patients to take an active role in data collection, the footwear applies inconspicuous foot data with analytics to improve health. One embodiment uses Google Maps to display health activity traffic; showing healthcare patterns based on real time reporting of anonymous data from healthcare footware devices. Healthcare organizations can tap the power of that data to engage patients and develop more effective and more personalized approaches to care, thereby lowering the overall cost of care. The system identifies pre-detectable characteristics of a health condition, such that future incidents of the health condition may be predicted, i.e., before the health condition occurs for disease prevention. One implementation includes capturing data from mobile fitness devices and establishing a plurality of health related characteristics associated with the population including walking status, weight, calorie burn. The characteristics include a plurality of pre-detectable characteristics with a relationship between the health related characteristics and at least one health condition, and analyzing at least a portion of said population in response to the relationship.

Another embodiment includes establishing at least one pre-detectable characteristic associated with a health condition, applying an intervention in response to the characteristic, monitoring a success characteristic of the intervention, and determining a cause of the success characteristic. Another embodiment builds a repository of health related characteristics associated with the population, the characteristics including a plurality of pre-detectable characteristics; and a processor configured to receive the health related characteristics, establish a relationship between the health related characteristics and at least one health condition, and analyzing at least a portion of the population in response to said relationship. A population, as used herein, is any group of members. The population may include a high level of members, for example a group including one or more of the five kingdoms of living things, or a subgroup, for example a group including humans of a certain age range. The population may include living and/or dead members. The analysis may include predicting a likelihood of a member developing the health condition, in response to the relationship. The health condition may be any type of physical or mental health condition, disease, and/or ailment. In addition, the analysis may include predicting the incidence of the health condition. The analysis may also include performing a simple yes/no prediction regarding whether a member will likely develop the health condition. The analysis may be used to enable the management of a health care program, such as a program associated with a corporation, or a program offered to the public by a health care consultant or provider. If the analysis is associated with a corporation's healthcare program, the population may include some or all of the employees and retirees of the corporation, and associated spouses and dependents. The population may include other associated groups of the corporation, such as consultants, contractors, suppliers and/or dealers. The population may include participants from multiple corporations and/or the general public. If the health care program is offered to the public, the population may include members of the public, organizations, and/or corporations. The health related characteristics may include a plurality of health characteristics, lifestyle characteristics and/or family health characteristics associated with the members of the population. Health characteristics may include characteristics indicative of a specific member's health. For example, lifestyle characteristic may include weight, heart rate, walking gait, sitting gait, running gait, exercise or activity as detected by accelerometers, diet, and other factors detectable by fitness devices such as watches, phones, or foot sensors detailed above. For other example, health characteristic may include medical characteristics (e.g., what medical visits, processes, procedures, or test have been performed associated with the member, the number of days the member has spent in a medical facility (e.g., a hospital), the number of visits the person has made to a doctor, etc.), drug characteristics (e.g., what type and amount of drugs are being consumed), a death characteristic (e.g., information associated with a death certificate), an absenteeism characteristic, disability characteristics, characteristics associated with existing health conditions, etc. Family health characteristics associated with the member may include information associated with the family medical history of a specific member. For example, a history of a particular health risk within the family, e.g., heart failure, cancer, high blood pressure, diabetes, anxiety, stress, etc. Lifestyle characteristic may include a specific member's behavior characteristic(s), of which some or all may be modifiable lifestyle characteristics. A modifiable lifestyle characteristic may include an exercise characteristic (e.g., does the member exercise, how often, what is the exercise, etc.) and/or a nutrition characteristic (e.g., what types of food does the member eat, and how often). Nutrition characteristics may also include the amount of salt consumed during a designated period (e.g., a day), and the amount of fat and/or saturated fat consumed during a designated period. In addition, modifiable lifestyle characteristics may include whether the member drinks alcohol (and if so how much), a drug intake characteristic, (i.e., does the member take drugs, and if so how often, what kind, and how much), a weight characteristic (e.g., what does the member weigh, what is the member's desired weight, is the member on a diet, what is the member's weight indicator e.g., obese, slightly overweight, underweight, normal, etc.), a smoking characteristic (does the member smoke and if so how much), a safety characteristic (what are the member's driving characteristics e.g., does the member where seat belts, have one or more infractions associated with driving under the influence, or speeding tickets, etc.). In addition, modifiable lifestyle characteristics may include a hypertension characteristic, a stress characteristic, a self-care characteristic, a self-efficacy characteristic, a readiness to change characteristics, and a prophylactic aspirin therapy characteristic.

In one embodiment, the health related characteristics may also include one or more of the following: demographic characteristics, the member's location or geography, age, gender, employment status, employment type, and/or work characteristics of the member. The health-related characteristics may be obtained through one or more of several sources, such as medical claims, drug claims, and/or self-reported characteristics (or data). In one embodiment, self-reported characteristics may be collected from the population. The amount and type of self-reported characteristics collected associated with the population is implementation dependent and may vary based upon the participation of the population, the relevance of the information to the different members of the population, and the analysis to be performed. Therefore the self-reported characteristics established may be associated with a subset, or portion, of the established population, or the entire population. The self-reported characteristics may include one or more health characteristics, family health characteristics, and lifestyle characteristics associated with a member of the population. The self-reported characteristics, also referred to as self-assessments, may be obtained through the use of one or more health related questionnaires submitted to the member. Examples of questionnaires include physical questionnaires, electronic questionnaires (e.g., located on a health related web-site), questionnaires filled out during a phone or personal interview, etc. The responses to the questionnaires may include a member's self assessed health related characteristics. The characteristics may include a self-efficacy characteristic and/or a readiness to change characteristic. A readiness to change characteristic is a characteristic indicative of a members readiness to change one or more behaviors, activities, or characteristics. A self-efficacy characteristic, as will be discussed, includes an indication of a member's belief in their ability to succeed in changing a lifestyle characteristic. For example the self-assessment questionnaire may specifically ask the member: does the member believe they can change their lifestyle or a specific aspect of their lifestyle, is the member willing to attempt to change an aspect of their lifestyle and if so, how successful do they think they will be, how important do they think it is to change one or more specified lifestyles, etc. Alternatively, one or more questions may be asked of which the answers may provide indirect indicators of whether the person actually does believe they can change aspects of their lifestyle, and also whether the member is actually ready to change a particular aspect of their lifestyle.

In one embodiment, the health related characteristics of the population are associated with self-reported biometric characteristics. For example, the sources of the health related characteristics may be self-reported biometric sources. That is, the sources of the health related characteristics are sources other than the direct physical examination of a member (e.g., where members provide a biological sample etc). The distinction is based on the issue that due to the size of the population, it may not be possible to analyze all of the members by having detailed examinations (e.g., blood samples, urine samples, etc.) of all, or even a substantial portion of the population. Therefore, in one embodiment, the health analysis is based on information that is obtained second-hand, without having physically examined a specific member to directly obtain the desired health related characteristics. Of course, if the described analysis indicates a particular member needs to be physically examined based on likelihood of occurrence of a health condition, which examination may occur. In one embodiment, the health related characteristics may relate to non-intrusive characteristics, i.e., characteristics that do not directly involve the physical examination or taking of biological samples of a member by a physician. For example, a blood sample may be considered intrusive data because it involves the taking of a sample from a member.

The collected health related characteristics may be stored in a repository. The duration of storage is implementation dependent, but in general the more information available for analysis, the more accurate the results will be. Therefore, a historical repository of five to ten years may be established. In some embodiments, characteristics may be available throughout the working career of the members, e.g., if their employer collects self-reported information, medical and/or drug claims. The historical repository aids analysis in several ways, including reducing the impact of recall bias. Recall bias is what may happen when a member acquires a particular health condition, and then attempts to recall what factors may have contributed to the condition. The members recollection may be biased by any number of issues including their ability to accurately remember all the desired information. Therefore a historical repository aids in providing accurate information for analysis.

The established health related characteristics may be used to analyze the health of the population. In one embodiment, as illustrated in a second control block 104, a prevalence of a health condition within the population may be established. The prevalence of a condition may be described as the current existence of a condition. The prevalence of a health condition among a population may be described as the number or percentage of members that have a specific health condition. Establishing the prevalence of a condition in a population may include determining which members currently have a specific health condition. The prevalence of a health condition may be established by analyzing the health related characteristics associated with one or more members of the population and responsively establishing whether one or more members has the condition. For example, the prevalence may be established by analyzing information associated with medical claims and/or drug claims associated with the population.

Medical claims may include any type of health related correspondence between a health analyst or provider (e.g., doctor, physician, medical laboratory, hospital, medical support group such as x-ray providers, etc.), and a member of the population and/or a health care insurer, provider, or manager, for the member (e.g., corporation (employer) or third party insurer/manager, etc.). In one embodiment, the healthrelated correspondence may include health codes such as E/M (Evaluation and Management) codes, Current Procedural Terminology (CPT) codes, and International Classification of Diseases (ICD) codes. ICD codes provide coded information associated with the treatment, health, and/or a condition of a member. These codes may include information associated with the professional services performed, the specific procedure(s) performed, and why the procedure(s) was performed. Therefore, analysis of ICD, CPT, and/or E/M codes may be used to establish whether a member has a particular health condition.

A drug claim may include any type of medication related correspondence between a medication provider (e.g., doctor, pharmacist, etc.), and a member of the population and/or a health care insurer, provider, or manager for the member (e.g., corporation (employer) or third party insurer/manager, etc.). In one embodiment, the correspondence may include codes or identification systems such as Group Product Index (GPI). The GPI provides a numbering system associated with the medication a member receives, and/or medication prescribed for a member. The GPI enables the identification of the type of drug, manufacturer, strength, associated dosage, and associated medication form (e.g., pill, tablet, liquid, etc.).

In one embodiment, information associated with at least one medical and/or drug claim may be used to determine the prevalence of a condition, e.g., whether a member has one or more specific health conditions. For example, if a medical claim indicates a particular procedure has been performed, then that procedure may be correlated to one or more potential health conditions associated with that procedure. Analogously, if a drug claim indicates that a member is being prescribed and/or receiving a particular medication, then that medication may be correlated to one or more potential health conditions associated with that medication. In this manner, the information associated with the medical and/or drug claims may be analyzed to establish a prevalence of a condition. The analysis may be performed on each member of the population, or a subset thereof.

In one embodiment, information associated with multiple medical and/or drug claims may be analyzed based on established criteria, to establish the prevalence of a health condition. For example, multiple medical and/or drug claims may be cross checked with each other to establish the prevalence of a health condition. An individual medical or drug claim may contain erroneous or misleading information. For example, there may be instances where a medical procedure is performed to test for a health condition, without definitively establishing the condition exists in the member. Analysis of the resulting medical claim may lead someone to erroneously believe the person had the healthcondition (e.g., based on the types of procedures being performed). Therefore, using one medical or drug claim may not provide an accurate indication of the presence of a health condition. Additional medical claims and/or drug claims may be analyzed to establish one or more healthrelated characteristics of a member, such as the prevalence of a health condition. In one embodiment, multiple medical and/or drug claims, separated by a time period (e.g., a minimum duration) may be analyzed. The separation in time increases the confidence level regarding the determination that a particular health claim, or health related characteristic, exists. For example, two claims of the same type (e.g., two medical claims or two drug claims), separated in time by at least three months, may be analyzed to determine if a member has a health condition. If the first claim indicates a condition exists, and a second claim indicates the same condition exists, then the member may be assumed to have the condition associated with the medical claims. The two claims may sequentially occur, or be separated by one or more other medical and/or drug claims. In addition, a claim of one type (e.g., medical claim) may be cross checked with a claim of another type (e.g., drug claim). If the two claims correlate, then the member may be considered to have the particular condition. The two different types of claims may also be separated by a designated time period, e.g., three months, to further establish that the condition actually exists. In one embodiment, the time separation is established such that the two claims represent independent indicators, as opposed to two claims associated with the same medical event (medical checkup or medication collection). Additional criteria may include that the claims being correlated should occur within a particular time period of each other. For example, if two claims indicating a particular health condition are separated by five years in time, there is a chance that the claims were inaccurate anomalies as opposed to indications of the existence of the health condition. Therefore, a maximum duration between claims being cross checked may be established (e.g., one year). In one embodiment, the maximum duration between cross checked claims may be dependent upon the condition at issue. For example, some health conditions may be more likely to have multiple claims occur within a specific time duration. While other health conditions may not manifest themselves in multiple medical claims in that same specified time duration. Therefore, the duration between claims may be implementation and health condition dependent.

When claims are received, they may be manually or automatically analyzed. For example, when a claim is received, it may be analyzed to establish associated health characteristics. The health characteristics may then be cross checked with information from other claims in an attempt to verify one or more of the health characteristics. The analysis may include correlating the claim with a table of potential health characteristics associated with claim information. The information may be compared with previous claim information to determine if prior claims indicated the same, or similar health related characteristics. If the cross check indicates one or more prior claims indicated the same health related characteristic, then the member may be assumed to have the health related characteristic (e.g., the health condition). If no prior claim information correlates with the current claim information, then the current claim information, and the correlated health related characteristics may be store to be compared with future claims that are to be receive. In one embodiment, if a strong correlation exists between the health related characteristics associated with multiple claims, and a sufficient time period exists between the claims, then the member may be determined to have the characteristics. Alternatively, machine learning such as classical, Bayesian, and/or statistical analysis techniques may be used to correlate and cross check one or more medical and/or drug claims with one or more health related characteristics and/or health conditions. For example, neural networks may be trained to associate information associated with medical and/or drug claims with particular health related characteristics and/or health condition. Then when a claim is received, it may be analyzed to establish potential health related characteristics and/or health conditions. The neural network may be able to provide a weighted analysis such that the results have an associated confidence factor. If multiple claims separated in time indicate the same or similar health related characteristics, the resulting neural network analysis may provide a higher confidence indicator than if just one claim indicated the characteristics. Therefore, as prevalent health conditions are established based on medical and/or drug claims, the claims may be further analyzed to establish a relationship capable of automatically detecting a prevalence based on the available medical and/or drug claims.

In one embodiment, the medical and/or drug claims may be analyzed as they are received. Alternatively, there may be a repository of one or more previous medical and/or drug claims associated with the member(s). For example, repositories may be created that include a members historical health related characteristics over a time period (e.g., the last five-ten years). These repositories may be maintained by the health care provider, insurer, analyzer, and/or manager. These repositories may be analyzed to establish a prevalence of a condition among the population. In one embodiment, self-reported characteristics may be analyzed to establish the prevalence of a condition, e.g., among one or more members of a population and/or the population as a whole. For example, a member may specifically indicate that they have a particular condition such as high blood pressure, diabetes, smoking, overweight, among others. Alternatively the analysis of one or more of the family history, lifestyle, or health characteristics indicated through the self assessments may indicate that the member likely has a particular condition. In this case additional follow-up may be performed with the member to determine if they actually have the condition, or know that they have the condition. In one embodiment, a relationship may be established to determine the existence of a condition among a particular member and/or among the population. In one embodiment, medical claims, drug claims, and self-reported characteristics may be used to establish the prevalence of a particular condition among the population. Alternatively, as indicated above, the prevalence of a condition may be established based on one or more of the sources of information (e.g., medical claims, drug claims, and/or self-reported characteristics). The prevalence may be established manually or through an automated process such as the use of statistical analysis techniques as mentioned above. The decision of what information (or sources of information) to use may be based on what information is available for the population, or for a particular portion of the population. For example, some portions of the population may not have a historical data base of information available for analysis. In addition, some portions of the population may not have associated medical claims, drug claims and/or self-reported characteristics. Therefore the type and amount of information to be analyzed to establish the prevalence of a disease is implementation dependent and may be based in part on the type of information available for a particular population, or portion thereof. A relationship may be established between the health related characteristics and one or more health conditions. In one embodiment, the relationship is established in response to the prevalence of the health condition. The relationship may then be modified based on future occurrences, or rates of occurrences of the condition. Alternatively, the relationship may be established by analyzing future occurrences or rates of occurrence of the condition without accounting for an initial prevalence of the condition. In one embodiment, as described below, the relationship may be used to predict an incident or occurrence of a disease, e.g., an occurrence of a disease among a particular member or among a population in general. Information gained from establishing the prevalence of the condition may be used to establish the relationship. For example, the health related characteristics associated with the members determined to have a particular condition may be analyzed to establish a relationship associated with a likelihood of developing the condition. In one embodiment, the predictive relationship is different than the analysis to determine the prevalence of a condition because the prevalence analysis may be used to establish who has the condition. However, the occurrence predictor may be used to establish the health related characteristics that are needed to predict the likelihood of developing the health condition. In one embodiment, all of the health related information associated with a member having a condition, or all of the health related information believed to be potentially relevant to a health condition that a member has, may be analyzed to establish the relationship. The health related information to be analyzed may be historical data that pre-dates the incidence of the health condition.

The analysis and associated relationship may indicate the pre-detectable characteristics associated with a health condition. Pre-detectable characteristics are characteristics that impact the chance of acquiring risk factors associated with a condition. A pre-detectable characteristic may be associated with more than one risk factor and/or more than one health condition. A heart attack is an example of a health condition. Risk factors associated with a heart attack may include obesity, age, and gender. A risk factor may be described as one form of a heath related characteristic that is a known, believed, or hypothesized to be an indicator of acquiring a health condition, or increasing the risk of acquiring the health condition. Risk factors usually have one or more pre-detectable characteristics associated with them. Pre-detectable characteristics associated with obesity, or being overweight, include dietary characteristics, such as the amount of saturated fat, fiber, and calories consumed during a time period. By reducing the amount of saturated fat consumed (a pre-detectable characteristic), the chances of acquiring the associated risk factor may be reduced (e.g., reduced chance of being overweight). If the chances of acquiring a risk factor is reduced or eliminated, then the chances of acquiring an associated health condition (e.g., the heart attack) are also reduced or possibly eliminated. As will be discussed, one embodiment of the present disclosure is associated with identifying pre-detectable characteristics associated with a health condition, and then predicting an incident of the condition associated with a particular member based on the particular health related characteristics associated with that member. Intervention recommendations may then be tailored to the particular pre-detectable characteristics exhibited by the particular member. In one embodiment, the collected health related characteristics may be detailed and extensive in order to acquire the desired information that may be associated with possible pre-detectable characteristics. By the nature of the analysis being performed, the pre-detectable characteristics may not be initially known. Therefore, monitoring of future occurrences of the condition, and analysis of the associated health-related characteristics enables the predictive relationship to evolve as new information is available.

The details of the establishment of the relationship will be described below. However, in general, the health related information associated with the population will be analyzed to establish the relationship. The analysis may include the use of statistical analysis techniques such as classical, Bayesian, and/or machine learning analysis techniques to analyze the health related information. For example, neural networks may be trained using all the health related characteristics of the members having a particular condition. Then, the health-related characteristics of a member of the population may be delivered to the neural network for analysis. The resulting analysis may provide a weighted answer indicative of the likelihood the person will acquire the condition. In addition, review of the neural network may provide insight into which health characteristics are more relevant to acquiring the condition. These characteristics may then be reviewed to establish the pre-detectable characteristics associated with the condition. For example, the relevant health related characteristic may be a pre-detectable characteristic, or may have associated pre-detectable characteristics. Therefore, depending on the specific implementation used, the analysis may be able to indicate the health related characteristics that are most relevant to the prediction of a particular health condition. The relationship may be used to analyze the population with respect to the health condition. For example, the relationship may be used to predict the likelihood of developing a condition associated with the population, or a portion thereof. As such, the relationship may be used to predict a future incident or occurrence of the health condition. In one embodiment, the health related information associated with one of the members of the population may be analyzed using the established relationship. The analysis may indicate, or predict, whether the member will develop a particular disease, which may include the likelihood the member will develop the particular disease. The analysis may be used to predict the occurrence of the disease based upon the established pre-detectable characteristics. In addition, this analysis, or information resulting from the analysis may be used to predict an incidence of the health condition, e.g., over a specified period of time, how many members will develop the disease, or what is the likelihood of a particular portion of the population developing the disease over a specified time period. In one embodiment, depending on the health condition associated with the analysis, the analysis may also establish a predicted time period in which the incident may occur (e.g, the next year, next five years, next ten years, etc.). In addition, the analysis may establish a stage of the condition associated with a particular member. For example, some conditions may have definable stages of the onset of the disease. In one embodiment, a likelihood of developing the condition may be established based upon the analysis. For example, some analytic techniques produce information associated with the likelihood of having the incidence, e.g, a confidence level. Therefore, the analysis may include classifying all or a portion of the population with respect to one or more conditions, based on the likelihood of the particular members having an incidence of the disease, based on the particular stages of the condition the population members fall within, and/or based on the predicted time period associated with the incidence. In this manner the population may be classified, or ranked, with respect to the likelihood of developing a condition, the time period in which the development may occur, and/or the stage of the condition the member is in. As described below, this classification, or ranking of the population, or a portion thereof, with respect to one or more conditions enables, specific interventions to be applied to specific members based on predicted risk, and also enables the management of the population as a whole, and the intervention and associated cost, etc. Therefore, the population may be analyzed to establish a likelihood of developing of one or more conditions, among one or more members of the population.

An intervention may be recommended in response to the likelihood of developing the health condition. Factors that may be used to select the appropriate intervention include the predicted likelihood the member will develop the health condition and the pre-detectable characteristics the member exhibits that are associated with the condition. For example, the more likely the person is to acquire a particular condition, the more aggressive the intervention recommendation may be. Other health related characteristics may also be used to determine the appropriate intervention, such as the self-efficacy characteristic and/or readiness to change characteristic associated with the member, and the likelihood of success of the intervention. The cost of the intervention may also be a factor in intervention selection. The role of intervention cost may be based on the premise that there is a finite amount of money available to administer health care interventions to the population. Therefore, one use of the analysis may be to determine how the interventions may be applied in a cost effective manner, while providing the best benefit for the population. For example, given the choice between recommending an intervention that is 60% effective and an intervention that cost twice as much, but is only 62% effective, the decision may be to apply the less expensive, yet effective intervention, and use the "savings" in other areas of the health care program. One implementation may include the step of establishing a success characteristic associated with the intervention. The success characteristic may include a characteristic associated with the success of the intervention, e.g., did the intervention succeed (or assist in succeeding) the prevention or delay of the incidence of the health condition. The success characteristic may include characteristics associated with whether the intervention was used, to what degree the intervention was used, why the intervention was, or was not used, and how effective was the intervention in light of how much it was used. Some of these success characteristics may be established shortly after recommending the intervention (e.g., was the intervention used and why or why not, to what degree the intervention was used, if not used what would it take to motivate the member to use, etc.), while other success characteristics may not be established for a period of time (e.g., if used, how successful was the intervention).

102. Success characteristics may be collected in several ways. Fitness sensors on the phone, watch, or foot can detect changes leading to/from success and provide appropriate warnings to the user or an assigned health coach. The characteristics may also be collected through medical and/or drug related information. For example, an intervention may include a recommendation that the member visit a medical provider (e.g., doctor), have a medical test performed, and/or be prescribed a particular drug. The members medical and/or drug claims may be monitored to determine if the recommendation was followed. For example, if over a particular time period, e.g., three months, there is no indication from reviewing medical claims, that the member visited a medical provider, then the assumption may be made that the member did not follow the recommendation. In light of this, a health care counselor or provider may be notified, and the member contacted to verify they did not follow the recommendation, and determine why the recommendation was not followed (if indeed it wasn't). This may be done by monitoring claims either manually or in an automated fashion, e.g., through the use of a computer program. For example, once an intervention is recommended, a computer related program may be configured to automatically review medical, drug claims, and/or self assessment characteristics to monitor characteristics of whether the recommended intervention was performed. In addition to fitness device reporting or through claims reporting, the success characteristics may be collected through self-reported data (e.g., targeted questionnaires, interviews, one on one phone calls such as counseling phone calls, etc.). For example, if a particular intervention recommended a medical visit, the targeted questionnaire or counseling call may specifically inquire as to whether the medical visit was made, and why or why wasn't the visit made. In one example, the success characteristics may include information indicative of a persons self-efficacy, and/or readiness to change. For example, if the established predictive relationship indicates that a particular member is at risk for a heart attack, and part of the pre-detectable characteristics associated with a heart attack is that the member is eating too much saturated fat, an intervention recommendation may include recommending a change in lifestyle, e.g., increased exercise such as running, walking, or swimming. The success characteristics may indicate that the person did not engage in any exercise (e.g., on a subsequent self assessment). Upon further follow up (e.g., within the same questionnaire or counseling session, or in a later one), the member may indicate that they don't enjoy exercising and/or they don't perceive the need to do so. Alternatively, the member may indicate that they tried running, but their knees hurt, so they stopped, and/or they did not have access to a swimming pool. That is, while they are willing to engage in a recommended intervention, the specific intervention recommended did not work for them. Alternatively, the member may indicate that while they enjoy working out, they do not have time outside of their work and family activities to engage in the recommended intervention. The measured characteristics may also indicate that the recommended intervention was followed. In this case, information may be obtained regarding why the recommendation was followed. The success characteristics may be used in several ways. In one embodiment, analysis may be performed with the success characteristics to establish a relationship capable of indicating or predicting a members engagement of an intervention, or willingness to engage in a particular intervention, or in any intervention. For example, the health related information, including the success characteristics, associated with members who have been recommended a particular intervention, may be analyzed. The analysis may result in a relationship that is able to establish the likelihood a particular member will follow a particular recommendation, based upon the specific health related information associated with the member. In one embodiment, the success characteristics may be used to establish a relationship capable of indicating or predicting a particular member's engagement of any recommendation, or willingness to engage in any intervention. In one embodiment, the analysis may include establishing a relationship capable of predicting a member's readiness to change stage. That is, in one embodiment, readiness to change categories may include a pre-contemplation, preparation, and action stages. If a member is in a pre-contemplation stage, they may not be willing to engage in any intervention. In the preparation stage, a member may be willing to pursue a particular intervention, but not just any intervention, or they may be willing to pursue interventions, but have not started. In the action stage, the member may be ready to take action in the appropriate intervention. By classifying a member into a readiness to change category, interventions may be further tailored for the individual member. For example, if a member is in the pre-contemplation stage, then the selected intervention may include additional counseling and/or educational literature associated with the seriousness of the potential condition, and the risk associated with this particular member of acquiring the condition if no action is taken. In addition, the intervention associated with the preparation category may include customizing the proposed intervention to the interventions the member is more likely to pursue. In this manner, self-efficacy and readiness to change characteristics associated with a particular intervention, may be analyzed with other self-efficacy and readiness to change characteristics associated with other interventions, and applied to the population as a whole where appropriate. That is, some established self-efficacy and readiness to change characteristics may be generalized (e.g., by creating a predictive relationship) and applied to the whole population to predict a particular members likelihood to engage in a particular intervention, or an any intervention. The analysis may include using statistical analysis (e.g., neural networks, regression analysis, etc.) to establish a relationship that is able to predict a members willingness or ability to pursue a particular intervention. In this manner a relationship may be developed and used in future instances such that when a member is predicted to have an incidence of a condition, the recommended intervention may be based upon indirect indicators of a members self-efficacy or readiness to change, as well as direct indicators (e.g., specific questions such as: are you willing to reduce your smoking).

For example, potential interventions may include an exercise regimen, a dietary regimen or a medication, to reduce the risk of a condition. The exercise regimen may indicate the highest success rate if followed, the medication the lowest success rate if followed. In addition, the member may provide strong direct indications of self-efficacy and readiness to change characteristics. However, the established participation predictive relationship may indicate that members with similar health characteristics (e.g., job requiring long hours, area of the country not conducive to exercise during the winter, and number of dependents in the family), that the member is not likely to follow through on an exercise regiment (e.g., due to time constraints from the job and family and inclement weather). However, based on the other members, it may be predicted that this member is most likely to follow through a dietary change. Therefore, the intervention may be targeted to either changing the dietary habits of the individual. In addition, the analysis of the success characteristics and associated health related characteristics may include establishing a relationship able to indicate a potential success of a particular intervention. For example, the success of an intervention may be established by monitoring/analyzing the health related information for an extended period of time. The health related information, including characteristics indicative of the incidence of the health condition may be monitored after the intervention is applied, and compared to health related characteristics expected if the intervention had not been applied (e.g., whether an incidence of the health condition would occur, when it would occur, when the stages of the incidence (if any) would occur. In addition, the health related characteristics may be analyzed to determine if any immediate changes in health care characteristics occurred. For example, if the health condition is a heart attack, and one of the pre-detectable characteristics associated with heart attacks is a members consumption of high saturated fats, then one intervention recommendation may be a dietary program. The health care characteristics may be monitored to determine if the dietary program was successful in reducing the members saturated fat consumption, and/or whether the dietary program was successful in eliminating or delaying the incidence of the health condition. Therefore the success of the intervention may be monitored with respect to eliminating or delaying the health condition, and/or eliminating or reducing a cause associated with the health condition. The results of the intervention monitoring and associated health related characteristics may be used to further refine the decision process regarding which intervention to recommend.

The health related characteristics, including the success characteristics, may be used to select one or more interventions for a particular member at risk of a particular condition. In addition, the health related characteristics may be used to establish a relationship that associates one or more interventions with particular health related characteristics and a health condition. The success characteristics may indicate that interventions have varying degrees of success based upon the health related characteristics such as the physical characteristics of the individual engaged in the intervention, the thoroughness of the use of the intervention, the willingness of the person to pursue, etc. For example, assume there are two potential interventions for a health condition. Assume intervention 1, if followed 100%, is 90% effective, and if followed 50% is 30% effective. In addition, assume intervention 2, if followed 100% is 60% effective, and if followed 50% is 45% effective. Depending on the health related characteristics of a particular member, the best chance of preventing or delaying the condition (or eliminating a cause of the condition) may lie with pursuing intervention 2. For example, if the self-efficacy characteristic, or readiness to change characteristic is low, this may be an indication that the member won't follow through completely with the recommendation. Therefore, the second intervention may be pursued that may have a better impact than the first intervention given that neither intervention is used completely. Therefore, a relationship may be developed that is able to predict the effectiveness of a particular intervention in general, e.g., if the intervention is used X %, then it will be Y % effective. This information may be used to make an intervention recommendation to a member or, to engage in further correspondence (interviews, follow-up questionnaires, etc.) with the member. For example, the member may be notified of the preferred intervention, but of the concerns that they are not going to fully engage the intervention. If they don't fully engage the intervention then there is an alternative intervention that is preferred. In addition, a relationship may be established to predict the usage of an intervention by a particular member, based upon the health related characteristics of the member. The relationship may also be able to predict the success of a particular intervention based on the predicted use of a member (e.g., based on the members self-efficacy, readiness to change, and or other health related characteristics). In addition, interventions may have varying success among different members, even if pursued to the same degree. Therefore, the recommendations may be modified based on any previous engagement by the member in an activity related to an intervention. For example, health related characteristics associated with the member and the activity the member engaged in may be used to tailor the specific recommendation provided. In one embodiment, the success characteristics associated with a particular member may be used to further refine, or establish, a recommended intervention for the member. In addition, the success characteristics may be used to refine the analysis (e.g., relationship) that correlates a member of a population with a particular intervention, based on the health related characteristics of the member. A relationship is established between the health related characteristics and a health condition. The type of analysis used to establish the relationship is implementation dependant and may vary as a function of the data available information being requested (e.g., explain the similarities/dissimilarities of the health related characteristics of members having the condition, predict future incidences, or both). The analysis may be dependent on the number of dependent variables (e.g., the health condition(s) associated with data) and/or independent variables (e.g., health related characteristics) that are being analyzed in the relationship and/or the objective of the analysis being performed. For example, the analysis may include the use of statistical analysis techniques such as classical, Bayesian, and/or machine learning techniques. Classical analysis techniques may include multivariate statistical techniques simple regression, multiple regression, factor analysis, item analysis multivariate analysis of variance, discriminant analysis, path analysis, cluster analysis, multidimensional scaling, rule induction, and/or least squares estimation. In one embodiment, multiple regression may be used to determine the relationship between one dependent variable (e.g., whether a person has diabetes) and multiple independent variables (i.e., multiple other health related characteristics, such as weight, gender, age, dietary habits, walking/running/exercise, etc.). Other techniques, such as in factor analysis, cluster analysis, and multivariate techniques may be used when the desired relationship is associated with multiple dependent variables and multiple independent variables. Generic model-fitting or classification algorithms e.g., neural networks (e.g., back propagation, feed-forward networks, etc.), meta-learning techniques such as boost, etc., may be applied for predictive data mining. Predictive data mining techniques may be desired when the accuracy of a prediction is of higher priority, regardless of whether or not the models or techniques used to generate the prediction is interpretable or open to simple explanation. That is, data mining techniques may be desired when the objective is to predict the future occurrence of a health condition, as opposed to analyze the existing relationship among the health related characteristics that leads to the health condition. As mentioned, the selection of the particular analysis technique(s) is implementation dependent and may be based on factors such as user preference, the data to analyze, and the number of dependent and/or independent variables, the objectives of the analysis. Therefore, in one embodiment of the present disclosure, the person analyzing the health of the population may specify the analysis techniques to be used, or the analysis system may automatically determine the appropriate technique(s) to use.

In one embodiment, data analysis using deep neural network techniques may be used to establish a predictive relationship between the health related characteristics and one or more health conditions. For example, the health related characteristics associated with members known to have a particular health condition, may be used to "train" the neural network. There are several types of neural network models. The selection of which model or combination to use may be implementation dependent, and implementation accuracy may vary based on model used, data analyzed, and desired objective of the model. In one embodiment, the model used is a back propagation network. The back propagation network may receive the health related characteristics associated with the members known to have a particular health condition, along with the characteristics of members known not to have the characteristic. The resulting "trained" neural network may then be able to receive the health related characteristics of a member to predict whether they will acquire the health condition. In one embodiment, the neural network output is a number (e.g., between zero and one), that may be used to indicate that the member has a determined likelihood of having an incidence of the condition (e.g., 75%), if they do not already have it. As was discussed above, the resulting likelihood of occurrence may be used to rank the population in terms of likelihood of acquiring the condition. This ranking may then be used to prioritize intervention strategies. In addition to establishing a likelihood of occurrence of the health condition, the internal organization of the neural network may be analyzed to determine which health related characteristics where most relevant to the condition. For example, a back propagation network includes multiple weighted interconnections between the input factors and the output. The weighted interconnections may be reviewed and correlated with the input health related characteristics. In this manner, the characteristics having more relevance (e.g., a higher weighting value) may be identified. These relevant characteristics may then be reviewed to establish the pre-detectable characteristics of associated with the health condition. For example, the established health related characteristics may already be pre-detectable characteristics (e.g., the amount of salt consumed per day, the amount of saturated fat consumed per day). However, if the established health related characteristics are not pre-detectable characteristics, then further analysis may be performed to break the characteristics into the pre-detectable characteristics. For example, if being overweight is established as a relevant health related characteristic, then further analysis may be performed to determine what pre-detectable characteristics lead to being overweight, and which of these pre-detectable characteristics did members being analyzed exhibit. In one embodiment, all of the factors associated with being overweight may be treated as being relevant. Alternatively, the potential pre-detectable characteristics are used to further refine the relationship to establish which of the pre-detectable characteristics plays a role in being overweight, when overweight is a factor in having a particular health condition, e.g., diabetes. In one embodiment, if multiple regression is the analysis technique used, an equation associated with the relationship may be: $Y=b1X1+b2 \times 2+ \ldots bnXn+c$, where the b's are the regression coefficients, representing the amount the dependent variable Y (e.g., likelihood of contracting a health condition) changes when the independent variable (the X's, e.g., the health related characteristics) change 1 unit. The c is the constant, where the regression line intercepts the y axis, representing the amount the dependent variable Y will be when all the independent variables are 0. In one embodiment, a determination may be made regarding whether any transformation (e.g., log functions, square roots, etc.) are needed to the proposed relationship (or equation). For example, should the log of a health related characteristic be used in the relationship, should the square root of a health related characteristic be used in the relationship, etc. As will be discussed, the form of the equation, e.g., whether one or more transformations are used, may be determined by the user, by the analysis system, or a combination thereof.

In one embodiment, different relationships may be created, e.g., using different transformations or different health related characteristics for the multiple regression analysis, and analyzed to determine which relationships perform better than others. Goodness of Fit analysis techniques such as R2, RMS, P Value, F ratios, standard error, etc., may be used to establish performance characteristics of the relationships. For example, techniques such as R2, which establish the percent of variance in the dependent variable (e.g., the part characteristic cost), explained collectively by the independent variables (e.g. the other part characteristics). By using R2, for example, an assessment may be made regarding which relationship best explains the variance in the dependent variable in response to the independent variables. RMS provides an indication of which model best predicts future aspects of a part, or part to be designed. In one embodiment, a threshold level of desired performance may be established for the relationship. If the relationship does not meet the threshold level of desired performance, then the user may be notified that the established relationship does not meet the desired level of accuracy, the desired level of ability to explain the variance in the dependent variable in response to the independent variables, or desired level of ability to predict future characteristics of the part. If multiple relationships are being compared with each other, and none of them exceed the desired level of success, then the user may be notified of which relationship performed best, but that none of them met the desired threshold. If multiple relationships are tested and one or more exceed the threshold, the best one may be selected, or they may all be provided to the user for selection.

One method for performing population health management includes establishing a plurality of health related characteristics associated with the population; establishing a relationship between the health related characteristics and at least one health condition; and analyzing at least a portion of said population in response to said relationship. The system can predict a likelihood of at least one of said members developing said at least one health condition, in response to said relationship and/or the members health related characteristics. The system can determine a prevalence of a health condition within said population in response to said health related characteristics. The plurality of health related characteristics associated with said population can be done by establishing a plurality of self-reported characteristics associated with at least a portion of said population. A prevalence of the health condition can be determined by: establishing a plurality of claims associated with at least one is said members, said claims including at least one of a drug claim and a medical claim; cross checking said plurality of claims (such as over a period of time, or over a number of tests); and establishing said prevalence in response to said cross checked claims. The system includes predicting a member's likelihood of developing a condition with a stage of said condition in response to said prediction. The system can predict a time period associated with said development. The system can classify said population in response to said prediction, and then prioritize treatment of the population in response to said prediction. The system can recommend an intervention in response to said predicted likelihood of development. This can be done by establishing a plurality of intervention recommendations associated with said condition; establishing a success characteristics of said recommended intervention; establishing at least one of a readiness to change characteristic and a self-efficacy characteristic of said member; and recommending said intervention in response to said plurality of intervention recommendations, associated intervention success characteristics, and member health related characteristics, said health characteristics including said self-efficacy and said readiness to change characteristic. The system can monitor failure/successful characteristic of said intervention, and determining causes resulting in said success characteristic. The system can capture a plurality of self-reported data associated with at least a portion of said population having said condition. The self-reported data includes at least one of a lifestyle characteristic, a family history characteristic, and a health characteristic. The predictive relationship can be done by establishing at least one objective of said relationship; dynamically selecting a statistical analysis technique in response to said objective; and establishing said relationship in response to said statistical analysis technique. The predictive relationship can be applied to at least a portion of said population; and predicting a likelihood of developing said condition in response to said application. The system can be configured to analyze the health of a population having multiple members. In one embodiment, the method includes the steps of establishing a plurality of health related characteristics associated with the population, the characteristics including a plurality of pre-detectable characteristics, establishing a relationship between the health related characteristics and the health condition, and predicting an incident of the health condition associated with at least one of the members, in response to the relationship. The health condition may be any type of physical or mental health condition, disease, and/or ailment. For exemplary purposes the method and system will be discussed as they may relate to the health condition diabetes. A repository of health related characteristics associated with a population may be collected. The health related characteristics may be collected through sources such as medical claims, drug claims, and self-reported information. The characteristics may include health characteristics, lifestyle characteristics, and family history characteristics. The characteristics may include the amount of saturated fat, unsaturated fat, fiber, salt, alcohol, cholesterol, etc. that a member consumes in a give time period. The characteristics may include weight characteristic, such as a member's weight, BMI (Body Mass Index), abdominal girth, etc. The characteristics may also include the person's blood pressure, standing heart rate, exercise habits (type and duration), and whether the member has hypertension. The health related characteristics of the population may be analyzed to establish the prevalence of diabetes among the population. For example, a medical claim having an ICD code with the prefix 250 is an indicator that the member may have diabetes. In addition, drug claims having a medication code descriptive of an anti-diabetes medication are indicators that the member has diabetes. The medical and/or drug claims are analyzed to determine if two claims indicating a member may have diabetes, and that are separated by at least three months, occur. If two claims meeting the criteria are identified, then the member is determined to have diabetes. For example, if two separate ICD codes occur, separated by at least three months, or one such ICD code occurs and one drug code for anti diabetes medication occur, e.g., separated by at least three months, then the member may be determined to have diabetes.

Once the population has been analyzed to establish who has diabetes, the historical health related characteristics of the diabetics are then used to establish a relationship between diabetes and the health related characteristics. For example, the health related characteristics are used to establish a neural network model, or regression model. The trained neural network and/or regression model will then be able to predict the likelihood a member of the population will acquire diabetes. In one embodiment, the neural network will also be able to establish who has, or may acquire, the related diabetic characteristics of metabolic syndrome and or glucose intolerance. Alternatively, these may be inputs to the neural network if available.

The established relationship may be reviewed to determine what the pre-detectable characteristics associated with diabetes are. For example, it may be determined that salt intake, consumption of saturated fats, and alcohol consumption are three leading pre-detectable characteristics of acquiring diabetes. In addition, it may be determined that smoking is not a pre-detectable characteristic associated with diabetes. The population may then be reviewed using the established relationship. The health related characteristics of each member of the population not known to have diabetes may be analyzed using the relationship. The analysis may indicate the likelihood the person will acquire diabetes (e.g., 75% likely). In addition, the pre-detectable characteristics associated with diabetes that are exhibited by the person may be identified. In this manner, the likelihood of the acquiring diabetes may be established along with what pre-detectable characteristics are the primary contributors to this particular member having diabetes Once the population's health related characteristics are analyzed, the population may be ranked by the individual member's likelihood of acquiring diabetes. In this manner, the type of intervention may be recommended based on the risk of acquiring diabetes, and the pre-detectable characteristics the member exhibits. In one embodiment, the interventions may be recommended by using another relationship (or an elaboration of the predictive relationship) to automatically make the recommendation based on the health related characteristics of the member, which may include the likelihood of acquiring diabetes and specific pre-detectable characteristics exhibited, self-efficacy and readiness to change characteristics of the member, etc. In one embodiment, the intervention may include additional questionnaires or interviews to acquire more specific information associated with diabetes from the individual. Other forms of intervention include one on one counseling to convince the member of the seriousness of diabetes, the risk of acquiring diabetes associated with them, the ability to delay or prevent the onset of diabetes by changing specified lifestyle characteristics, and the specific actions the member may take to modify specific aspects of their lifestyle associated with the pre-detectable characteristics. For example, if dietary issues are causing the member to be overweight, the intervention may include, suggested changes to dietary consumption, cookbooks directed towards the desired diet, or even corporate sponsored diet counseling or involvement in a commercial diet control program. The specific intervention recommended may be based on the likelihood of acquiring diabetes the person has, the members willingness to change their diet and belief that they will be successful in long term dietary change, and how much of a factor dietary issues were in establishing this particular members likelihood of acquiring diabetes.

Once the intervention recommendation is provided additional monitoring may occur to determine if the member followed through with the recommendation (including why they did or didn't follow through), whether the intervention helped reduce the targeted characteristic (e.g., the targeted pre-detectable characteristic), and when the intervention did reduce the targeted characteristics, whether the ultimate occurrence of diabetes was either delayed (which may be a subjective determination) or prevented altogether. The results of this monitoring may then be used to update the established relationships. In addition, as incidents of diabetes occur, the health related characteristics of effected member may be used to further refine the established predictive relationship. In this manner, the health of the population may be analyzed and managed relative to diabetes. The system can receive data from electronic medical records (EMRs), activity data from patient watches and wearable devices, population demographic information from govt databases, consumer profile information from credit card companies or consumer sales companies, provider (doctor, dentist, caregiver) entered information, one or more output registry databases. The EMRs may span multiple applications, multiple providers, multiple patients, multiple conditions, multiple venues, multiple facilities, multiple organizations, and/or multiple communities. Embodiments of the EMRs may include one or more data stores of healthcare records, which may include one or more computers or servers that facilitate the storing and retrieval of the healthcare records. In some embodiments, one or more EMRs may be implemented as a cloud-based platform or may be distributed across multiple physical locations. Example embodiments of the EMRs may include hospital, ambulatory, clinic, health exchange, and health plan records systems. The EMRs may further include record systems, which store real-time or near real-time patient (or user) information, such as wearable, bedside, or in-home patient monitors, for example. It is further contemplated that embodiments of the EMRs may use distinct clinical ontologies, nomenclatures, vocabularies, or encoding schemes for clinical information, or clinical terms. Further, in some embodiments, the EMRs may be affiliated with two or more separate health care entities and/or venues that use two or more distinct nomenclatures. In embodiments, the EMRs described herein may include healthcare data. As used herein, healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives. In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

In embodiments, activity data can refer to health actions or activities performed by a patient outside of, or remote from, a healthcare environment. Embodiments of activity data may include one or more data stores of activity data, which may include one or more computers or servers that facilitate the storing and retrieval of the activity data. In some embodiments, the activity data may be implemented as a cloud-based platform or may be distributed across multiple physical locations. Example embodiments of the activity data may include nutrition information and/or exercise information for a patient. In certain embodiments, at least a portion of the activity data may be recorded utilizing a personal fitness tracker, a smart phone, and/or an application provided by a smart phone. In various embodiments, the activity data may include data obtained from a patient's car. For example, in such embodiments, the activity data include data on the amount of driving the patient does versus the amount of walking the patient does. In one or more embodiments, the activity data may be submitted by a patient, a third party associated with a personal fitness tracker and/or smart phone (such as a software developer or device manufacturer), a care provider, a payer, etc. In certain embodiments where the activity is being submitted by anyone other than the patient, the patient may be required to approve of such submission and/or may opt-in to or opt-out of having such healthcare data being submitted.

The patient and/or population demographic information may include age, gender, date of birth, address, phone number, contact preferences, primary spoken language, technology access (e.g., internet, phone, computer, etc.), transportation (e.g., common modes of transportation), education level, motivation level, work status (student, full-time, retired, unemployed, etc.), and/or income. In certain embodiments, the patient and/or population demographic information may include community resource information, which may include, but is not limited to, fitness facility information, pharmacy information, food bank information, grocery store information, public assistance programs, homeless shelters, etc. In embodiments, the motivation level can include the level of motivation a particular patient has for maintaining their health, which may be derived from other information (e.g., data from personal fitness tracker, indication the patient regularly visits a clinician for check-ups, consumer profile information, etc.). Embodiments of the patient and/or population demographic information may include one or more data stores of demographic information which may include one or more computers or servers that facilitate the storing and retrieval of the demographic information. In some embodiments, the patient and/or population demographic information may be implemented as a cloud-based platform or may be distributed across multiple physical locations. In embodiments, the patient and/or population demographics may be obtained through any source known to one skilled in the art. For example, in certain embodiments, at least a portion of the patient and/or population demographic information may be submitted by a third party that relies on census data. In various embodiments, the patient and/or population demographic information may be obtained from more than one source. In one embodiment, the patient may submit any or all of the patient and/or population demographic information. In certain embodiments, all or a portion of the patient and/or population demographic information may be anonymized using techniques known to one skilled in the art. In one or more embodiments, the consumer profile information may include any or all of the spending habits of one or more patients within a population. For instance, in certain embodiments, the consumer profile information may include information associated with grocery store purchases, athletic or exercise equipment purchases, restaurant purchases, and/or purchases of vitamins and/or supplements. Embodiments of the consumer profile information may include one or more data stores of consumer profile information which may include one or more computers or servers that facilitate the storing and retrieval of the consumer profile information. In some embodiments, the consumer profile information may be implemented as a cloud-based platform or may be distributed across multiple physical locations. In one embodiment, a patient may provide the consumer profile information, for example, by linking checking account and/or checking account purchase information to at least a portion of the population health management system and/or to a health insurance carrier. The care provider information may include any information relating to a particular care provider or healthcare facility. In one embodiment, the care provider information may include information relating to the number of healthcare providers and their specialties at a particular care provider location. In the same or alternative embodiments, the care provider information may include information relating to non-personnel type resources at a particular care provider location, such as the amount and types of medications and/or the amount and types of surgical or other medical equipment. In one embodiment, the care provider information may include one or more of address and contact information, accepted payer information, status on accepting new patients, transactional systems, primary spoken language, hospital affiliations, and/or care delivery models. In embodiments, the care provider information may include information relating to the availability of any or all resources at a particular healthcare facility including personnel and/or non-personnel resources. Embodiments of the care provider information may include one or more data stores of care provider information which may include one or more computers or servers that facilitate the storing and retrieval of the care provider information. In some embodiments, the care provider information may be implemented as a cloud-based platform or may be distributed across multiple physical locations. In one embodiment, the care provider information can be provided by a healthcare provider, and/or a third party, such as an insurance provider or management entity. Information in the output registry databases may be categorized or classified according to, for example, claims, diagnoses, wellness, satisfaction, population directories, and the like. In various embodiments, each output registry may be used by, for example, a healthcare organization to manage the health of a population segment. In one or more embodiments, each output registry may be condition specific. By way of example, a healthcare organization or clinician may manage diabetic patients within a proscribed geographic area. The condition in this example is diabetes mellitus and the output registry may help the healthcare organization manage a population segment with this condition. The output registry may, in one aspect, include identified patients within a population segment who have this condition or have risk factors that may lead to the development of diabetes, for example. The output registry may further include grouped patients within an identified segment by degree of severity or risk, such as those grouped by the grouping component of the population health server. The grouped patients in an output registry may facilitate the generation of interventions or action workflows designed to reduce disease severity or risk and to improve outcome. Additional uses for the output registries are to measure outcomes related to treatment interventions and also to attribute patients within the identified segment to appropriate healthcare providers (e.g., primary care physicians, care managers health coaches, specialists such as endocrinologists, podiatrists, and the like).

In embodiments, the plurality of EMRs may be associated with a plurality of healthcare providers, a plurality of patients, a plurality of medical conditions, a plurality of healthcare venues and/or facilities, a plurality of organizations, and/or a plurality of communities. In certain embodiments, in addition to or in place of the healthcare data, the system can receive activity data from fitness devices, demographic information, e.g., the patient and/or population demographic information; consumer information, e.g., the consumer profile information; and provider information, e.g., the care provider information. The system can identify a population of patients based on a set of criteria, which may, in one example, be received from a clinician device such as a blood pressure unit, among others. In one or more embodiments, the set of criteria may include one or more medical conditions. In the same or alternative embodiments, the set of criteria may include demographic information of one or more patients, such as age, gender, race, and/or location of residence. In one or more embodiments, the system may utilize any or all of the information and data such as:

healthcare data, e.g., the healthcare data present in one or more EMRs; activity data; demographic information, e.g., the patient and/or population demographic information; consumer profile information; and care provider information. In certain embodiments, to identify as many people as possible in a population that may have or have a particular medical condition of interest, the system may utilize clinical data, such as lab test results, in combination with other healthcare data. In such embodiments, the particular medical condition can be any condition where specific types of clinical information, e.g., lab test results, may be used to identify one or more patients that have or may have that condition. Exemplary conditions may include, but are not limited to, diabetes and heart disease. For example, in embodiments, the system may utilize diagnostic information, medication information, and/or one or more lab test results to identify a patient as having or potentially having diabetes. In such embodiments, by using information from one or more lab test results, the system may identify one or more patients that have diabetes or may have diabetes, even if they have not been formally diagnosed with diabetes or have not been prescribed diabetes medication. In the same or alternative embodiments, the system may utilize lab test results in combination with other healthcare data to identify pre-condition patients, which may allow early intervention to prevent a patient from developing a particular condition. In one or more embodiments, the system can identify subsets of a population not based on a medical condition. For instance, in such embodiments, the system can identify subsets of a population based on aspects of one or more patients in a population of patients, e.g., age, gender, primary spoken language, income level, healthcare motivation level, education level, technology access (e.g., phone, computer, etc.), contact preferences, work status (student, full-time, unemployed, retired, etc.), healthcare facility visit history and frequency, advanced directives, and/or consumer profile information. In various embodiments, the system can identify subsets of a population based on non-medical aspects of patients, specific care provider information, and/or population and/or community based resources in order to enable actions and care planning, measure compliance, improve care transitions, optimize utilization of resources, and contain costs.

In one or more embodiments, the system can group a population of patients based on a clinically relevant data from the EMRs. For example, in embodiments, the clinical data may include one or more of medication information, laboratory values, diagnostics, clinical narratives, and clinician assessments. In the same or alternative embodiments, the clinical data may include data obtained from the natural language processing of one or more clinical assessments and/or clinical narratives. In certain embodiments, the system can group a population of patients based on diagnostic codes, intervention codes, insurance claims, and/or medication information associated with each patient. The system can also group patients using substantially similar attributes can include one or more of disease risk levels and/or scores, one or more disease stages, and/or one or more healthcare objectives. For example, in certain embodiments, the system can group a population of patients, such as a population of patients identified as having or potentially having diabetes, into at least two groups corresponding to Type I and Type II diabetes. The system can group based on venue location, specialty, spoken language, readmission rate, medical and/or prescription compliance level, socioeconomic status, address, employment status, marital status, education level, age, sex, dependents, race, ethnicity, insurance status, and primary spoken language, associated healthcare support system, and/or utilization level of healthcare facilities (including pharmacies). The grouping can finely classify individual patients as having a low, medium, or high medication compliance risk based on information related to the ability to access a pharmacy, the ability to pay for medications, and/or the presence of medication gaps in the healthcare record. In other embodiments, individual patients may be grouped based on the number of appointments made, the number of appointments scheduled, the number of appointments attended, the number of missed appointments, the type of appointment, the date and time of the appointment, the visit location, the venue, and whether or not the patient acknowledged the appointment (e.g., was the patient aware of the appointment). The system can predict patients as having a low, medium, or high level of compliance with filling prescriptions based, at least in part, on the number of prescriptions written, the number of prescriptions filled, and the date and time the prescriptions were filled.

The information includes genetic data. The system can model diseases as the result of multiple genetic mutations interacting with environmental factors, diet and lifestyle choices, microbiome differences and metabolic responses. In one embodiment, the medical data includes sequenced body fluid samples containing circulating tumor cells (CTCs) and cell-free DNA (cfDNA). CTCs have an intact, viable nucleus; express cytokeratins, which demonstrate epithelial origin; have an absence of CD45, indicating the cell is not of hematopoietic origin; and have morphology consistent with cancer, often larger cells with irregularity cell or subcellular morphology. Cytokeratin negative (CK−) CTCs are cancer stem cells or cells undergoing epithelial mesenchymal transition (EMT). CK-CTCs may be the most resistant and most prone to metastasis; express neither cytokeratins nor CD45; have morphology similar to a cancer cell; and have gene or protein expression or genomics associated with cancer. Apoptotic CTCs are traditional CTCs that are undergoing apoptosis (cell death). Measuring traditional CTC to apoptotic CTCs ratio from baseline to therapy provides clues to a therapy's efficacy in targeting and killing cancer cells. Small CTCs are cells that are cytokeratin positive and CD45 negative but have a size and shape similar to white blood cells. Importantly, small CTCs have cancer specific biomarkers that identify them as CTCs. Small CTCs have been implicated in progressive disease and differentiation into small cell carcinomas which often require a different therapeutic course. CTC Clusters are made up of two or more individual circulating tumor cells bound together. The CTC cluster can be made up of traditional, small or CK− CTCs. CTC clusters have cancer specific biomarkers that identify them as CTCs and are associated with increased metastatic risk and poor prognosis.

In another embodiment, the medical data is captured from sequenced from microvesicles isolated from a sample taken of a bodily fluid from a subject. As used herein, a "bodily fluid" refers to a sample of fluid isolated from anywhere in the body of the subject, preferably a peripheral location, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, bronchoalveolar lavage (BAL), cyst fluid, tumor cyst fluid, amniotic fluid and combinations thereof. Preferably, the bodily fluid is plasma, serum, cerebrospinal fluid, ascites fluid, bronchoaveolar lavage, or cyst fluid. In some embodiments, it is preferable that the bodily fluid sample is within the range of 2-20 ml. In some aspects, it may be preferable to use a larger volume of sample for increased accuracy in detecting rare genetic mutations, such as the BRAF mutation described herein. In some aspects, the bodily fluid sample is within the range of 1 to 25 ml, for example, from 2 to 25 ml, from 2 to 20 ml, from 2 to 15 ml, from 2 to 10 ml, from 4 to 25 ml, from 4 to 20 ml, from 4 to 15 ml, from 4 to 10 ml, from 6 to 25 ml, from 6 to 20 ml, from 6 to 15 ml, from 6 to 10 ml, from 8 to 25 ml, from 8 to 20 ml, from 8 to 15 ml, from 10 to 25 ml, from 10 to 20 ml, from 10 to 15 ml, from 15 to 25 ml or from 15 to 20 ml.

Following the isolation of microvesicles from a biological sample, nucleic acid may be extracted from the isolated or enriched microvesicle fraction. Nucleic acid molecules can be isolated from a microvesicle using any number of procedures, which are well-known in the art, the particular isolation procedure chosen being appropriate for the particular biological sample. The extracted nucleic acids can be DNA and/or RNA. In some embodiments, the DNA is extracted. In some embodiments, RNA is extracted. In some embodiments, both DNA and RNA are extracted. The RNA can be messenger RNA, transfer RNA, ribosomal RNA, small RNAs, non-coding RNAs.

In one embodiment, the extracted nucleic acid is RNA. RNAs are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR). The analysis of nucleic acids present in the microvesicles is quantitative and/or qualitative. For quantitative analysis, the amounts (expression levels), either relative or absolute, of specific nucleic acids of interest within the microvesicles are measured with methods known in the art (described below). For qualitative analysis, the species of specific nucleic acids of interest within the microvesicles, whether wild type or variants, can be identified.

The system can capture 'omics data, including genomics, transcriptomics, proteomics, and metabolomics data, to understand the biology of an organism and its response to environmental stimuli or genetic perturbation. Metabolome refers to the complete set of small-molecule metabolites (such as metabolic intermediates, hormones and other signaling molecules, and secondary metabolites) found in a sample. Analytes in a metabolomic sample comprise highly complex mixture. This complex mixture can be simplified prior to detection by separating some analytes from others. For analysis by mass spectrometry the analytes are transferred to the gas phase using electron ionization (EI), chemical ionization (CI), or electrospray ionization (ESI), among others. Identification leverages the distinct patterns in which analytes fragment which can be thought of as a mass spectral fingerprint; libraries exist that allow identification of a metabolite according to this fragmentation pattern. Alternatively, nuclear magnetic resonance (NMR) spectroscopy does not rely on separation of the analytes, and the sample can thus be recovered for further analyses.

Once metabolic composition is determined, data reduction techniques can be used to elucidate patterns and connections. A principal component analysis (PCA) can be used to efficiently reduce the dimensions of a dataset to a few which explain the greatest variation. When analyzed in the lower-dimensional PCA space, clustering of samples with similar metabolic fingerprints can be detected. This clustering can elucidate patterns and assist in the determination of disease biomarkers—metabolites that correlate most with class membership. Metabolic profiling (especially of urine or blood plasma samples) detects the physiological changes caused by toxic insult of a chemical (or mixture of chemicals). In many cases, the observed changes can be related to specific syndromes, e.g. a specific lesion in liver or kidney. Metabolomics can be used for determining the phenotype caused by a genetic manipulation, such as gene deletion or insertion. Nutrigenomics is a generalised term which links genomics, transcriptomics, proteomics and metabolomics to human nutrition. In general a metabolome in a given body fluid is influenced by endogenous factors such as age, sex, body composition and genetics as well as underlying pathologies. Metabolomics can be used to determine a biological endpoint, or metabolic fingerprint, which reflects the balance of all these forces on an individual's metabolism. The system can also be used to study environmental metabolomics to characterize the interactions of organisms with their environment.

In one embodiment, metabolites and immune cell function correlating with exercise can be tracked. Blood draws and resting echocardiogram are taken. The patient exercises on a treadmill for approximately 15 minutes, followed by another echocardiogram. After the exercise and echocardiograms, periodic blood draws are done over the course of several hours. The metabolites with elevated levels are correlated with echocardiogram, electrocardiogram, VO2 max testing, and vascular ultrasound evaluation to identify metabolites associated with exercise and they are tracked over time to predict the patient's fitness level.

The system can monitor disease (e.g. cancer) progression or recurrence in a subject. These methods include isolating microvesicles from a bodily fluid of an individual and analyzing nucleic acid within the microvesicles to create a genetic profile of the microvesicles. The presence/absence of a certain genetic aberration/profile is used to indicate the presence/absence of the disease (e.g. cancer) in the subject. For example, the process includes detecting the presence or absence of one or more mutations in the extracted DNA and RNA, and the presence of the one or more mutations in the extracted DNA and RNA indicates the presence of a disease or other medical condition in the subject or a higher predisposition of the subject to develop a disease or other medical condition.

The liquid biopsy process is performed periodically over time, and the results reviewed, to monitor the progression or regression of the disease, or to determine recurrence of the disease. Put another way, a change in the genetic profile indicates a change in the disease state in the subject. The period of time to elapse between sampling of microvesicles from the subject, for performance of the isolation and analysis of the microvesicle, will depend upon the circumstances of the subject, and is to be determined by the skilled practitioner. For example, a gene which is targeted by the therapy can be monitored for the development of mutations which make it resistant to the therapy, upon which time the therapy can be modified accordingly. The monitored gene may also be one which indicates specific responsiveness to a specific therapy.

The data processed by the system is reflective of a large population by including participants from diverse social, racial/ethnic, and ancestral populations living in a variety of geographies, social environments, and economic circumstances, and from all age groups and health statuses. One embodiment applies precision medicine treatment to many diseases, including common diseases such as diabetes, heart disease, Alzheimer's, obesity, and mental illnesses like depression, bipolar disorder, and schizophrenia, as well as rare diseases. Importantly, the system can focus on ways to increase an individual's chances of remaining healthy throughout life.

In an implementation, social network information may be maintained in a computer graph structure with nodes and edges such that each node represents a user or an organization in the network and each edge represents a known direct connection between two nodes. A number of attributes described within social networks may be stored in a database, associated with each user (also referred to herein as nodes) and strength of influence (also referred to herein as edges or distances). In some embodiments, the engine may be further configured to determine distances to one or more of the patient members closest to a current patient's biological data with a diameter of at least one grouping and to indicate that the new patient is associated with the grouping based on the comparison. In various embodiments, the engine is further configured to determine if the distance to one or more of the patient members closest to the new patient's filtered biological data is greater than a diameter of each grouping and to indicate that the new patient is not associated with each grouping based on the comparison. The medical characteristic may comprise a clinical outcome.

In one implementation, nodes may comprise attributes that include but are not limited to: a unique identifier assigned such as a user's name, address and/or other items of information; unique identifiers for the node in each external social network containing the node, statistical summaries of the node's network, and pointers to the user's medical data. In an implementation, edges of the social network may comprise attributes that include but are not limited to the unique identifiers of the two nodes that are connected by the edge, the source of the node's information (i.e. the external social network), the assigned social influence from the first node to the second node, and the assigned social influence from the second node to the first node, and statistical summaries of the edge's contribution to the network.

The above mentioned examples are not intended to be limiting, and it is intended that any medical data is included within the scope of this disclosure. In an implementation, a user may be able to designate which health provider sites or medical sites that may be desirable to obtain information from, or the sites may be automatically selected. The social health content may be presented to the user or alternatively to a health professional for assessment. For example, a user may be presented with a list of all of her medical connections from her health history sites. In such an example the user may wish to select all of the available connections, or may wish to limit the selection to only a certain number of connections. A user may be asked to assign a strength of influence (for example, a numerical value) for each of the connections received from the social networks. In an implementation, the method will receive user influence information (data) by asking the user to assign a strength of influence for a connection that represents the user's similarity to another user. Likewise, the method will receive user influence information (data) by asking the user to assign a strength of influence for a connection that represents the medical influence that any other user may have over the user herself. The strength of influence information may be recorded into memory as an influence metric. Influence metrics may be discussed in the terms of distance, even though an actual distance may not exist between the points of social data used in the method. A list of recommendations may be created for the user base on his medical neighborhood and the behavior of others within the health/medical neighborhood. For example, if influential patients of the neighborhood are using and talking about certain medication or treatment modalities, it is likely that the user may desire to apply the same medication/treatment. As such, a timely recommendation from a research would prove beneficial to both the treating professional and the patient/user.

Exemplary systems and methods for disease management are provided. In various embodiments, a method comprises identifying similar patient clusters, generating groups and interconnections of the groups, each group having one or more members that share medical similarities, each interconnection interconnecting groupings that share at least one common member, determining whether a new member shares medical similarities with the one or more members of each group and associating the new member with one or more groups. The similarities may represent similarities of measurements of gene expressions or similarities of sequencing.

In one embodiment, the system includes cluster the data based on a metric, and display the groupings and the interconnections based on the clusters. The filtering function may be a density estimation function. The metric may be a Pearson correlation.

Additionally, the system can monitor biomarkers for individual diseases such as high blood pressure or diabetes. A biomarker is "a characteristic that is objectively measured and evaluated as an indicator of normal biological processes, pathogenic processes, or pharmacologic responses to a therapeutic intervention." A biomarker may be measured on a biosample (as a blood, urine, or tissue test), it may be a recording obtained from a person (blood pressure, ECG, or Holter), or it may be an imaging test (echocardiogram or CT scan). Biomarkers can indicate a variety of health or disease characteristics, including the level or type of exposure to an environmental factor, genetic susceptibility, genetic responses to exposures, markers of subclinical or clinical disease, or indicators of response to therapy. Thus, a simplistic way to think of biomarkers is as indicators of disease trait (risk factor or risk marker), disease state (preclinical or clinical), or disease rate (progression). 16 Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). In one embodiment, blood testing is done to determine different components of the immune system as well as lipids and glucose metabolism. An ultrasound image is created by placing a transducer which sends sound waves and receives reflections from inside the body. Those reflections are computerized to recreate a picture of the arteries of the neck. The thickness of the carotid artery called intima-media thickness is a reflection of early cholesterol build-up in the carotid arteries. The ultrasound of the femoral arteries is also done to measure arterial stiffness, a good measure of vascular health. Ultrasound of the abdominal aorta is used to screen for abdominal aortic aneurysms.

The endothelium is the inner lining of blood vessels. The endothelium regulates blood flow and maintains vessel health. Several studies have shown that endothelial dysfunction is a risk factor for cardiovascular disease. Peripheral arterial tonometry is a method to assess endothelial function using a device positioned at the fingertips and a blood pressure cuff (response after deflation of the blood pressure cuff). An echocardiogram is a diagnostic test which generates images of the heart by bouncing high frequency sound off the structures of the heart and recording the returned echoes and processing them into images. The sound is transmitted and received with a transducer placed upon the chest. For example, biomarkers for use in distinguishing, or aiding in distinguishing, atherosclerotic subjects from non-atherosclerotic subjects include 3-methylhistidine, p-cresol sulfate, mannose, glucose, and/or gluconate, and combinations thereof. In one aspect biomarkers for use in methods relating to atherosclerosis using plasma samples from a subject include one or more of 3-methylhistidine, p-cresol sulfate, mannose, glucose, gluconate, among others. In one embodiment, cardiovascular disease (CVD) biomarkers are processed by the system. For example, CVD related biomarkers can be tracked such as ADMA, asymmetrical dimethyl arginine; Apo B, apolipoprotein B; CETP, cholesterol ester transfer protein; GPX1, glutathione peroxidase; IL, interleukin; IMT, intimal-medial thickness; Lp(a), lipoprotein a; LpPLA2, lipoprotein-associated phospholipase A2; LV, left ventricle; LVH, LV hypertrophy; MMP, matrix metalloproteinase; MPO, myeloperoxidase; SAA, serum amyloid A; sCD40L, soluble CD40 ligand; sICAM, soluble intercellular adhesion molecule; PAI-1, plasminogen activator inhibitor 1; PET, positron emission tomography; TIMP, tissue inhibitor of matrix metalloproteinases; and TPA, tissue plasminogen activator.

Generally, people with type 1 diabetes present with acute symptoms of diabetes and markedly elevated blood glucose levels. Because of the acute onset of symptoms, most cases of type 1 diabetes are detected soon after symptoms develop. Type 2 diabetes is frequently not diagnosed until complications appear, and approximately one-third of all people with diabetes may be undiagnosed. Individuals at high risk should be screened for diabetes and pre-diabetes. In one embodiment, the system analyzes clinical risk models that include individuals who are overweight (BMI≥25 kg/m2*) and have additional risk factors including: are habitually physically inactive, have a first-degree relative with diabetes, are members of a high-risk ethnic population (e.g., African American, Latino, Native American, Asian American, Pacific Islander), have delivered a baby weighing >9 lb or have been diagnosed with GDM, are hypertensive (≥140/90 mmHg), have an HDL cholesterol level <35 mg/dl (0.90 mmol/l) and/or a triglyceride level >250 mg/dl (2.82 mmol/l), have PCOS, on previous testing, had IGT or IFG, have other clinical conditions associated with insulin resistance (e.g., PCOS or acanthosis nigricans), have a history of vascular disease. The system can monitor urinary protein associated with diabetes mellitus. They include defense proteins (al-antitrypsin, Complement factor H, C3, B, I, C7, 9), Alpha-1-antichymotrypsin precursor, Antithrombin-III, Alpha-2-glycoprotein 1, zinc, Ig gama 1 chain C region, Alpha and beta-2-microglobulin, Alpha-2-antiplasmin precursor, Vitronectin precursor); Transport (Serotransferrin precursor, Ceruloplasmin precursor, Hemopexin, AMBP protein, Albumin, Haptoglobin precursor, Transthyretin precursor, VDBP); Metabolism (ApoA-1, ApoA-II precursor, Apo-D, Alpha-1B-glycoprotein, Beta-2-glycoprotein 1 precursor, Prostaglandin H2 D-isomerase precursor, Alpha-2-HS-glycoprotein precursor, E-cadherin, Dystroglycan precursor, Fibrinogen beta chain precursor); Signal transduction (Kininogen precursor, B-factor, properdin, Clusterin, Angiotensinogen, Sulfated glycoprotein 2, retinol-binding protein 4, Epidermal growth factor) and cell development protein such as Lumican precursor. The system can track proteins in human serum of patients having diabetes mellitus such as:

a. Cytokines and cytokine-related proteins Leptin, TNF-alpha, IL-6
b. Immune-related proteins MCP-1
c. Proteins involved in fibrinolytic system PAI-1
d. Tissue factor
e. Complement and complement-related proteins Adipsin (complement factor D), ASP, Adiponectin Lipids and proteins for lipid metabolism or transport Lipoprotein lipase (LPL), Apolipoprotein E, Apolipoprotein A1, Apolipoprotein A2, Apolipoprotein B+, Apolipoprotein H, Apolipoprotein C1, C2, NEFAs, Cholesterol ester transferase protein (CETP),
f. Inflammatory proteins C-reactive protein (CRP), α-tumor necrosis factor (αTNF)

Individuals at high risk for developing diabetes are made aware of the many benefits of modest weight loss and participating in regular physical activity. The system can generate recommendations and track patient compliance. Follow-up counseling is important for success and a coach can be assigned to help the patient. Monitoring for the development of diabetes in those with pre-diabetes is performed regularly using mobile fitness devices. The system can also recommend appropriate treatment given for, other CVD risk factors (e.g., tobacco use, hypertension, dyslipidemia). Because of possible side effects and cost, there is insufficient evidence to support the use of drug therapy. An intensive lifestyle modification program has been shown to be very effective (~58% reduction after 3 years). Use of the pharmacologic agents metformin, acarbose, orlistat, and rosiglitazone has also been shown to decrease incident diabetes to various degrees. Of note, however, each of these drugs may cause side effects of varying severity in a small number of individuals. Physical activity and behavior modification are important components of weight loss programs and are most helpful in maintenance of weight loss. Thus, lifestyle change should be the primary approach to weight loss. The system recommends and monitors structured programs that emphasize lifestyle changes, including education, reduced energy and fat (~30% of total energy) intake, regular physical activity, and regular participant contact to achieve produce long-term weight loss on the order of 5-7% of starting weight. Saturated fat intake should be <7% of total calories. Intake of trans fat should be minimized. The system monitors carbohydrate, whether by carbohydrate counting, exchanges, camera detection or experience-based estimation, for glycemic control. The methods and systems as disclosed herein may comprise, or comprise the use of, predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof. The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias. Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia greata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's diseasevDercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditisvHenoch-Schonlein purpuravherpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Meniere's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods and systems as provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants. The methods and systems as disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods and systems as disclosed herein may identify fetal mutations or genetic abnormalities. The methods and systems as disclosed herein can enable detection of extra or missing chromosomes, particularly those typically associated with birth defects or miscarriage. The methods and systems as disclosed herein may comprise, or comprise the use of, the diagnosis, prediction or monitoring of autosomal trisomies (e.g., Trisomy 13, 15, 16, 18, 21, or 22) and may be based on the detection of foreign molecules. The trisomy may be associated with an increased chance of miscarriage (e.g., Trisomy 15, 16, or 22). Alternatively, the trisomy that is detected is a liveborn trisomy that may indicate that an infant may be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes. Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXXY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

The methods and systems as disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. Additional pathogens include, but are not limited to, *Mycobacterium tuberculosis, Streptococcus, Pseudomonas, Shigella, Campylobacter,* and *Salmonella*. The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot. The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis. The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*). The methods and systems as disclosed herein may comprise, or comprise the use of, treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications. Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof. The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, anti-malarial, anti-tuberculosis drug, anti-leprotic, or anti-protozoal. Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole. The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin. Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin. In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection. Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx). Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin. Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Such antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body. Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™ etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (emtricitabine, rilpivirine, and tenofovir disoproxil fumarate). Herpes viruses, best known for causing cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir. In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc). Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, immunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peg-interferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism. Antiparasitics are a class of medications which are indicated for the treatment of infection by parasites, such as nematodes, cestodes, trematodes, infectious protozoa, and amoebae. Like antifungals, they must kill the infecting pest without serious damage to the host.

Various dietary chemicals act on the human genome, either directly or indirectly, to alter gene expression or structure. Nutrients may act directly as ligands for transcription factor receptors; may be metabolized by primary or secondary metabolic pathways, thereby altering concentrations of substrates or intermediates involved in gene regulation or cell signaling; or alter signal transduction pathways and signaling. The degree to which diet influences the balance between healthy and disease states depends on an individual's genetic makeup. The system includes monitoring nutrigenomics and metabolomics using mass spectroscopic techniques to identify multiple analytes in parallel and detect gene expression in response to an environment. In one embodiment, proteomics workflows identify the proteins in a sample. In shotgun proteomics, the sample's proteins are solubulized and digested into short peptides of 10-20 amino-acids using a proteolytic enzyme. The resulting peptide mixture is separated in time according to the peptides' physical and chemical properties using liquid chromatography and analyzed in real-time by the mass-spectrometer. As the peptides with similar physicochemical properties elute from the column, the mass spectrometer acquires survey scans to identify and select the most abundant peptide ions for analysis by tandem mass-spectrometry. Mass spectrometry measures the mass of molecules and atoms. The molecules to be analyzed are transformed into charged, gas-phase ions which can be manipulated and detected by the mass spectrometer. One embodiment is a quantum dot mass spectrometer with an array of different dots each filtering specific wavelengths of light. Each dot only lets through a certain wavelength of light and the dots are so small they can be printed onto a thin film and can be placed on top of a camera or they can be deposited onto each camera pixel sensor.

Various open-source and commercial tandem mass-spectrometry search engines can be used including Mascot from company Matrix Science, and SEQUEST available from Thermo Fisher, or open source software such as X!Tandem and OMSSA. The automated acquisition of tandem mass spectra in conjunction with liquid-chromatography can be done, and tandem mass-spectrometry search engines analyze these shotgun proteomics datasets to identify the sample's proteins. The search engines match the tandem mass spectra with peptide sequences from a protein sequence database and use the identified peptides to infer the protein content of the sample. A mass analyzer uses electrical, magnetic, and RF fields to separate the gas-phase ions in time or space before they are counted and detected.

The system recommends dietary intervention based on knowledge of nutritional requirement, nutritional status, and genotype (i.e., "individualized nutrition") can be used to prevent, mitigate or cure chronic disease. In another preferred embodiment the physiological data includes epigenetic data, genetic data, genomic data, and nutrigenomic data. In a further preferred embodiment, the physiological data comprises measurements of heart rate, breathing rate and volume and blood pressure. In a still further preferred embodiment, the physiological data includes measurements of weight, BMI, HDL, LDL, cholesterol, glucose, lipids, HbA1c, blood pressure, biomarkers of inflammation, TNF-α, HsCRP, leukotrienes, prostaglandins, and hormones. In a more preferred embodiment, the hormones comprise insulin, glucagon, and leptins. In another preferred embodiment the physiological data is collected before and after consumption of a food item. In a yet further preferred embodiment the disease or disorder is selected from type 2 diabetes. mellitus (T2DM), obesity, metabolic syndrome, Alzheimer's disease, cardiovascular disease, and cancer. In a most preferred embodiment, the disease or disorder is type 2 diabetes mellitus. Candidate genes include:

| Gene | Function | Effect |
|---|---|---|
| HNF-4α, HNF-1β IPF-1, NeuroD1 | Transcription Factors | ↓Insulin Secretion |
| HNF-1α, | Transcription Factor | ↓Insulin Secretion |
| Glucokinase | Glucose Metabolism | ↓Insulin Secretion |
| Calpain-10 | Protease | Unknown |
| PPARγ | Transcription Factor | ↓Insulin Sensitivity |
| Insulin Receptor | Transmits Insulin Signals into cells | ↓Insulin Secretion and Sensitivity |
| IRS1 and -2 | Insulin Signaling | ↓Insulin Sensitivity |
| Akt2 | Insulin Signaling | ↓Insulin Sensitivity |
| 11-β-HSD | Glucocorticoid Synthesis | ↑Blood Lipid, ↓Insulin Secretion |
| UCP2 | ↓ATP Synthesis | ↓Insulin Secretion |
| Resistin | Fat Cell "hormone" | ↓Insulin Sensitivity |
| Adiponectin | Fat Cell "hormone" | ↓Insulin Sensitivity |

Candidate coronary syndromes include:

| Plaque | Unstable plaque | Plaque rupture | Thrombosis | Ischemia | Necrosis | LV remodeling |
|---|---|---|---|---|---|---|
| LDL | MMP-9 | sCD40L | PAI-1 | IMA | cTNT | BNP |
| ox LDL | MPO | PlGF | sCD40L | FFA | cTNI | NT-ProBNP |
| CRP | ICAM | PAPP-A | VwF | Choline | CK-MB | MMP |
| IL-6 | VCAM | VCAM | D-dimer | BNP | Myg | |
| IL-10 | | | | ?IL-6/TF | | |
| IL-18 | | | | | | |
| Fbg | | | | | | |
| TNF- | | | | | | |

Biomarkers that may be elevated at each phase of coronary disease are displayed in the above sequence, where sCD40L indicates soluble CD40 ligand; Fbg, fibrinogen; FFA, free fatty acid; ICAM, intercellular adhesion molecule; IL, interleukin; IMA, ischemia modified albumin; MMP, matrix metalloproteinases; MPO, myeloperoxidase; Myg, myoglobin; NT-proBNP, N-terminal proBNP; Ox-LDL, oxidized low-density lipoprotein; PAI-1, plasminogen activator inhibitor; PAPP-A, pregnancy-associated plasma protein-A; P1GF, placental growth factor; TF, tissue factor; TNF, tumor necrosis factor; TNI, troponin I; TNT, troponin T; VCAM, vascular cell adhesion molecule; and VWF, von Willebrand factor.

252. FIG. 13 shows an exemplary patient monitoring system. The system can operate in a home, a care facility, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/ stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 1, for transmitting data from the appliances 8 to the local hub or receiving station or base station server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network. More details of the mesh network is shown in FIG. 7 and discussed in more detail below. An interoperability protocol supports the automatic configuration of an appliance with the base station. When the user operates a new appliance, the appliance announces its presence and the base station detects the presence and queries the device for its identity. If the device is not recognized, the base station determines where to find the needed software, retrieves the software, install the support software for the appliance, and then ran the device's default startup protocol that came in the downloaded installation package. The protocol allows remotely located systems or users to authenticate the identity (and possibly credentials) of the persons or organizations with whom they are interacting and ensures the privacy and authenticity of all data and command flowing between the appliances and any internal or external data storage devices. A public key infrastructure or cryptographic mechanism for facilitating these trusted interactions is used to support a global e-medicine system infrastructure. The protocol allows independently designed and implemented systems to locate each other, explore each other's capabilities (subject to each station's access control rules), to negotiate with each other and with the networks that they will use to determine how a given session will be run (for example, what Quality of Service requirements will be levied and what resources will be leased from each other), and to then conduct collaborative operations. The protocol contains instructions regarding the kinds of components that are needed to support the protocol's operation, the ways in which these components need to be interconnected, and events that are to be monitored during the time that the protocol is active.

253. A plurality of monitoring cameras 10 may be placed in various predetermined positions in a home of a patient 30. The cameras 10 can be wired or wireless. For example, the cameras can communicate over infrared links or over radio links conforming to the 802X (e.g. 802.11A, 802.11B, 802.11G, 802.15) standard or the Bluetooth standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliance 8 detects that the user needs assistance or that an emergency had occurred.

254. The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

255. The patient 30 may wear one or more wearable patient monitoring appliances such as wrist-watches or clip on devices or electronic jewelry to monitor the patient. One wearable appliance such as a wrist-watch includes sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch. In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters. The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission. In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure. In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm. The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

The exemplary devices 8, 10, and 40 include a layer of device-specific software (application interface) which supports a common language (such as, for example, the Extension Markup Language (XML)) to interface with the base station or local server 20. The base station 20 acts as a gateway or moderator to coordinate the devices 8, 10 and 40 in a local network neighborhood. The base station 20 supports multiple communication protocols and connectivity standards so that it may talk to other devices in one language (e.g., XML) but using different protocols and/or connectivity standards (such as, for example, Hypertext Transfer Protocol (HTTP), File Transfer Protocol (FTP), Simple Network Management Protocol (SNMP), Internet Inter-Orb Protocol (HOP) in Common Object Request Broken Architecture (CORBA), Simple Object Access Protocol (SOAP) with Extension Markup Language (XML), Ethernet, Bluetooth, IEEE 802.11a/b/g (WiFi), 802.16 (WiMAX), ZigBee, Infrared Detection and Acquisition (IrDA), General Packet Radio Service (GPRS), Code Division Multiplexed Access (CDMA), and Global System for Mobile Communication (GSM), or any other appropriate communications protocol or connectivity standard). The base station 20 performs device registration, synchronization, and user authentication and authorization. The application interface provides a simplified way of communicating with the base station 40 which provides a seamless integration and synchronization among the devices 8, 10 and 40 for example. Hence, instead of connecting individual devices directly (point-to-point) to a network, such as, for example, the Internet, to obtain services, the base station 20 runs a "middleware" software that hides protocol and connectivity details from the device. Consequently, services from the Internet, for example, may be provided without being concerned about future development of new protocols, services, and connectivity.

268. To obtain services from external sources, the base station 20 makes a request based on the information collected from the multiple devices and issues the request to the remote server 200. The remote server 200 acts as a proxy/gateway to request, consume, and/or distribute web services from a variety of content sources. In this regard, the communications between the base station 20 and the server 200 are encrypted to protect patient identifiable information and other private details of the person. Also, a variety of services may be aggregated and cached, thus providing a faster response time and better use of network bandwidth. The server 200 may store information regarding the devices and/or service providers. In this regard, the server 200 may include a user profile database that maintains an updated copy of the user profile and application data so that intelligent content services and synchronization among different devices may be provided. In a wireless network environment, availability may not always be guaranteed so that another mechanism, such as, for example, a queue structure, may be required to save the data, profiles, and results for later retrieval.

269. The devices 8, 10 and 40 register with the base station 20 and provide information regarding the capabilities of the device, including, for example, device type (EKG, EMG, blood pressure sensor, etc.) memory size, processing capacity, and supported protocols and connectivity. The base station 20 processes service requests from the devices and may enhance the service requests and/or combine them collectively before issuing the requests in response to queries from a requester such as a doctor who polls the server 200 on the status of the patient. Upon receiving the request from the doctor through the server 200, the base station 20 "tailors" the request to suit the proper device capability before relaying it the appropriate device. Hence, the devices 8, 10 and 40, issue requests on behalf of themselves and receive responses individually according to their particular capabilities while the base station 40 customizes and combines requests/responses to simplify and/or improve communication efficiency. Data is automatically synchronized to maintain a consistent state of the devices, regardless, for example, of network availability and/or unreliable networks.

Next, an exemplary process for providing interoperability between two devices within the base station network (such as devices 8, 10 and 40) is described. Pseudo-code for the device interoperability process is as follows:

271. Device requests registration with base station (S2)
272. Base station registers devices with remote server on their behalf (S4)
273. Device requests application data from base station (S6)
274. Base station searches for a responsive device from its registration list and forwards request to responsive device over preferred communication channel (S8)
275. Responsive device replies to base station with data (S10)
276. Base station reformats data to match requesting data's preference (S12)
277. Base station forwards formatted data to requesting device on requesting device's communication channel (S14)

In the next example, an exemplary process for providing interoperability between a device within the base station network (such as one of devices 8, 10 and 40) and an external device (such as a cell phone) is described. Pseudo-code for the device interoperability process is as follows:

279. Cell phone and In-Network Devices requests registration with base station (S22)
280. Base station registers devices with remote server on their behalf (S24)
281. Cell phone requests application data from base station (S26)
282. Base station searches for a responsive device from its registration list and forwards request to responsive device over preferred communication channel (S28)
283. Responsive device replies to base station with data (S30)
284. Base station reformats data to match cell phone's preference, in this example SMS (S32)
285. Base station forwards SMS formatted data to cell phone over cellular channel (S34).

In S24, the base station registers the devices, including their connectivity and protocol capabilities. During the registration, the base station determines, for example, that the EKG monitor device supports IEEE 802.15.4 connectivity standard (ZigBee) and the cellular telephone supports Bluetooth and SMS messaging. In S26, the cell phone may trigger an application supported by the EKG device. In S28, the base station receives the request and searches for a registered device that supports that application. For example, base station searches a device table and finds that the cellular telephone is able to process SMS messages and the EKG monitoring device can communicate over ZigBee and stores data in the OpenEKG format. In step S28, the base station relays the application request to the EKG monitoring device. The monitoring device captures EKG data from the patient and sends the data to the base station. In S32, the base station reformats data to SMS message format and to send the SMS message to the requesting cell phone. In this regard, the exemplary system may provide a transparent SMS service to the cell phone from a Zigbee device. Hence, from a receiving device perspective, the cell phone thinks that the EKG monitoring device is sending and receiving SMS messages, but the EKG monitoring device is not able to perform SMS messaging by itself. The translation is transparently and automatically done by the base station.

In the following example, an exemplary process for providing interoperability between a device within the base station network (such as one of devices 8, 10 and 40) and an external device at a clinic or hospital is described. Pseudo-code for the device interoperability process is as follows:

288. Hospital/Clinic devices and In-Network devices requests registration with remote server (S42)
289. Remote server forwards registration request to all base stations, which in turn register hospital/clinic device (S44)
290. Hospital device requests application data from server, which in turn forwards request to base station (S46)
291. Base station searches for a responsive device from its registration list and forwards request to responsive device over preferred communication channel (S48)
292. Responsive device replies to base station with data (S50)
293. Base station reformats data to match requestor's preference (S52)
294. Base station forwards formatted data to hospital/clinic device through the remote server (S54)

In one implementation, a Bluetooth device discovery can be done by having one device initiating queries that are broadcast or unicast addressed. Service discovery is the process whereby services available on endpoints at the receiving device are discovered by external devices. Service means the interfaces described by means of Device Descriptors set. Service discovery can be accomplished by issuing a query for each endpoint on a given device, by using a match service feature (either broadcast or unicast) or by having devices announce themselves when they join the network. Service discovery utilizes the complex, user, node or power descriptors plus the simple descriptor further addressed by the endpoint (for the connected application object). The service discovery process enables devices to be interfaced and interoperable within the network. Through specific requests for descriptors on specified nodes, broadcast requests for service matching and the ability to ask a device which endpoints support application objects, a range of options are available for commissioning universal healthcare applications that interact with each other and are compatible.

Next a logical interface between two connected systems, a Manager (typically a host/BCC) and an Agent (typically a device/DCC) is detailed. The interface is generally patterned after the International Organization for Standardization's Open Systems Interconnection (OSI-ISO) seven-layer communications model. That model was created to foster interoperability between communicating systems by isolating functional layers and defining their abstract capabilities and the services relating adjacent levels. The four so-called "lower" OSI layers are the (1) physical, (2) data link, (3) network, and (4) transport layers. Layers 5, 6, and 7—the session, presentation, and application layers—are known as "upper" layers. Layers 1-4, the "lower" layers, constitute the transport system, which provides reliable transport of data across different media. The session layer includes services for connection and data transfer (e.g., session connect, session accept, and session data transfer). The Presentation Layer holds services for negotiating abstract syntax, such as Medical Device Data Language (MDDL) over CMDISE ASN., and transfer syntax, which are basic encoding rules (BER) or optimized medical device encoding rules (MDER). MDERs are abstract message definitions that include primitive data types such as FLOAT (floating-point numeric) or 32-bit integer, and the way they are encoded as bits and bytes for communication over the transport. The association control service element or ACSE (ISO/IEC 8650) provides services used initially to establish an association between two communicating entities, including association request and response, association release, association abort, and others. The ROSE or remote operation service element (ISO/IEC 9072-2) provides basic services for performing operations across a connection, including remote operation invoke, result, error, and reject. The CMDISE or common medical device information service element, is based on CMIP (the common management information protocol; ISO/IEC 9596-1) and provides basic services for managed objects, including the performance of GET, SET, CREATE, DELETE, ACTION, and EVENT REPORT functions. These services, invoked using ROSE primitives, represent the basic means for interacting with the medical data information base (MDIB). The medical data information base supplies an abstract object-oriented data model representing the information and services provided by the medical device. The data originate in the device agent (the right side in FIG. 1) and are replicated during connection on the Manager side of the system. Objects include the medical device system (MDS), virtual medical device (VMD), channels, numerics, real-time sample arrays, alerts, and others. Application Processes. This layer represents the core software on both the host (BCC) and device (DCC) sides of the connection that either creates or consumes the information that is sent across the link.

To provide orderly system behavior, a finite-state-machine model for the life cycle of a BCC-DCC interaction is used. After a connection is made at the transport level, the DCC proceeds to associate with the managing BCC system and configure the link. Once configuration has been completed, the communication enters the normal operating state in which, in accordance with the profile that is active, data may be exchanged between the two systems. If the device is reconfigured—for example, if a new plug-in module is added—it can transition through the reconfiguration state, in which the Manager is notified of the changes in the Agent's MDIB data model, and then cycle back to the operating state. The interactions between an Agent (DCC) system and a Manager (BCC) system begins once the Manager transport layer indicates that a connection has been made, the Manager application, using ACSE PDUs, initiates the association-establishment process, which results on the Agent side in the association-request event being generated. Association being accomplished, the Agent notifies the Manager that the MDS object has been created. This MDS-create-notification event report includes static information about the device's manufacturer, its serial number, and other configuration data. At this point, the Manager can create a context scanner within the device's MDIB. A scanner is a tool that collects information of various kinds from the device's MDIB and sends it to the Manager in event-report messages. A periodic scanner will examine a set list of data items in the MDIB (for example, in an infusion pump, this list might include the parameters "volume infused" and "volume to be infused"), and send an update at regular intervals of every few seconds.

In one example with an infusion-pump, a context scanner is used to report the object-model containment tree to the Manager system. This way, the Manager can "discover" the data that are supported by a given device. Because the MDIB contains a finite set of object types (MDS, VMD, channel, numeric, alert, battery, etc.), a Manager does not need to know what an infusion device looks like, it can simply process the containment tree retrieved from the context scanner and configure itself accordingly. Once the containment tree has been sent to the Manager system and the Agent has received a confirmation reply, the MDS object indicates that it has entered the configured state and automatically passes to the operating state, ready to begin regular data communications. A set of base station-to-device interfaces are provided and include those that enable appliances, medical instruments, patient record cards, and user interface components, among others, to be added to and removed from the station in a plug-and-play fashion.

The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format. The appliances can communicate data conforming to the interoperable format over one of: cellular protocol, ZigBee protocol, Bluetooth protocol, WiFi protocol, WiMAX protocol, USB protocol, ultrawideband protocol. The appliances can communicate over two or more protocols. The first medical appliance can transmit the first vital information over a first protocol (such as Bluetooth protocol) to a computer, wherein the computer transmits the first vital information to the second medical appliance over a second protocol (such as ZigBee protocol). The computer can then transmit to a hospital or physician office using broadband such as WiMAX protocol or cellular protocol. The computer can perform the interoperable format conversion for the appliances or devices, or alternatively each appliance or device can perform the format conversion. Regardless of which device performs the protocol conversion and format conversion, the user does not need to know about the underlying format or protocol in order to use the appliances. The user only needs to plug an appliance into the network, the data transfer is done automatically so that the electronic "plumbing" is not apparent to the user. In this way, the user is shielded from the complexity supporting interoperability.

Another exemplary process for monitoring a patient is discussed next. The process starts with patient registration (1000) and collection of information on patient (1002). Next, the process selects a treatment template based on treatment plan for similar patients (1004). The process generates a treatment plan from the template and customizes the treatment plan (1006). The system considers the following factors: medical condition, amount of weight to lose, physician observations regarding mental state of the patient. In the event the patient has extensive or contraindicating medical history or information, the system alerts the doctor to manually review the patient file and only generate recommendations with authorization from a doctor. The doctor subsequently reviews and discusses the customized plan with the patient. In one embodiment, during the discussion, the doctor offers the patient the opportunity to enroll in the automated monitoring program. For a monthly or yearly fee, the system would provide the patient with periodic encouragements or comments from the system or the physician. In one embodiment, the doctor can provide the patient with an optional monitoring hardware that measures patient activity (such as accelerometers) and/or vital signs (such as EKG amplifiers). Upon user enrollment, the system's workflow helps the doctor with setting goals with the patient, establishing a bond of trust and loyalty, and providing positive feedback for improving compliance. Loyalty to the practitioner initially produces higher compliance, emphasizing that establishing a close relationship helps. By providing rapid feedback through instant messaging or emails, the system helps doctors earn the patient's respect and trust, set goals together with the patient, and praise progress when it occurs. Once enrolled, the system collects data on patient compliance with a treatment plan (1008). This can be done using mobile devices with sensors such as MEMS devices including accelerometer and others as described more fully below. Alternatively, the system periodically requests patient data will be weighed, measured, body fat calculated, blood pressure, resting heart rate and overall well-being. In one embodiment, the system provides a daily (7 days a week) counseling process using texting, email or social network communications. The process also accumulates reward points for patient to encourage healthy activities, such as jogging, walking, or gardening (1010). The process also compares patient progress with other patients (1012) and sends automatic encouraging messages to patients (1014). Upon patient authorization, the system announces the patient's goals and progress to a social network such as Facebook. The social network strengthens the patient's will for dieting and exercise by the "extent to which individuals perceive that significant others encourage choice and participation in decision-making, provide a meaningful rationale, minimize pressure, and acknowledge the individual's feelings and perspectives." The system supplements the treatment through social supports at home and encourages the patient to make their family and close friends aware of their condition and the expectations of diet and exercise. This will provide the patient with encouragement and accountability. Periodically, the system shows patient status to doctor (1016) and presents recommendations to doctor on preventive steps, such as check-ups and basic blood tests (1018). Automatically, the system schedules in person consultation for patient and doctor (1020). Captured progress data can be viewed by the physicians and patients using a web based system. The physician can review all interactions between the system and the patient. The physician is able to see their progress reports, interactive e mail which includes daily menus and notes between the service and the patient. The physician will be able to check on the patient's progress at any time of day or night. The system improves the Doctor-Patient relationship and influences compliance.

In one embodiment, body analysis data is determined from enrollment data, and include: body mass ratio, pounds of lean muscle mass, percentage of body fat and an optimal range for the specific individual of that percentage, pounds of body fat and an optimal range of body fat for that specific individual, and suggested pounds of body fat to lose. The body analysis includes the following: Basal Metabolic Rate (BMR) is the number of calories burned by the patient's lean body mass in a 24 hour period at complete rest using formulas such as the Harris-Benedict formula or other suitable formulas. Specific Dynamic Action of Foods (SDA) is the numbers of calories required to process and utilize consumed foods (in one case estimated at 5-15% of BMR, depending on personalization). Resting Energy Expenditure (REE) is the sum of BMR and SDA and represents the number of calories that the patient's body requires in a 24 hour period at complete rest. The system determines a Program Recommendation Total Caloric Intake as the caloric supplement required to achieve weight loss of approximately 2 pounds per week. Medications or stimulating substances (such as caffeine, gingsen, or diethylpropion) to assist in weight loss may be recommended and if so the program increases calorie consumption based on a model of the patient's response to such substances.

In one embodiment using the optional mobile monitoring hardware, the system determines Activities of Daily Living (ADL) as the number of calories burned by the patient's body during normal daily activities using accelerometers. The accelerometers can also determine the Calories Burned by Exercise as the number of calories burned by the exercises selected by the patient. Also included, is the level and intensity of the patient's activities. In one embodiment without the optional mobile monitoring hardware, the system approximates the Activities of Daily Living (ADL) as an average of calories expected to be burned by the patient's body during normal daily activities, and in one case is estimated at 20% or REE. The system can also receive averaged approximations of Calories Burned by Exercise is the number of calories burned by the exercises selected by the patient. Also included, is the level and intensity of the patient's activities. An exemplary process for monitoring patient food intake is discussed next. The process first determines and recommends optimal diet based on patient parameters (1030). To monitor progress, the process takes user entered calorie data and optionally captures images of meals using a mobile device such as a mobile camera (1032). The process then translates images of the meals into calories (1034). The patient's actual diet is then compared to with the recommended diet (1036). In one embodiment, the camera captures images of the food being served to the patient. The image is provided to an image search system such as the Google image search engine, among others. The search returns the likely type of food in the dish, and an estimation of the container volume is done. In one embodiment, the volume can be done using a 3D reconstruction using two or more images of the food found as the intersection of the two projection rays (triangulation). The two images from the 2D images are selected to form a stereo pair and from dense sets of points, correspondences between the two views of a scene of the two images are found to generate a 3D reconstruction is done to estimate the 3D volume of each food item. The system determines and looks up a database that contains calorie per unit volume for the dish being served, and multiplies the food volume estimate with the calorie per unit volume for the type of food to arrive at the estimated total calorie for the dish. The user is presented with the estimate and the details of how the estimation was arrived at are shown so the user can correct the calorie estimation if needed.

Recognition of Exercise Pattern and Tracking of Calorie Consumption

Figure 16A:
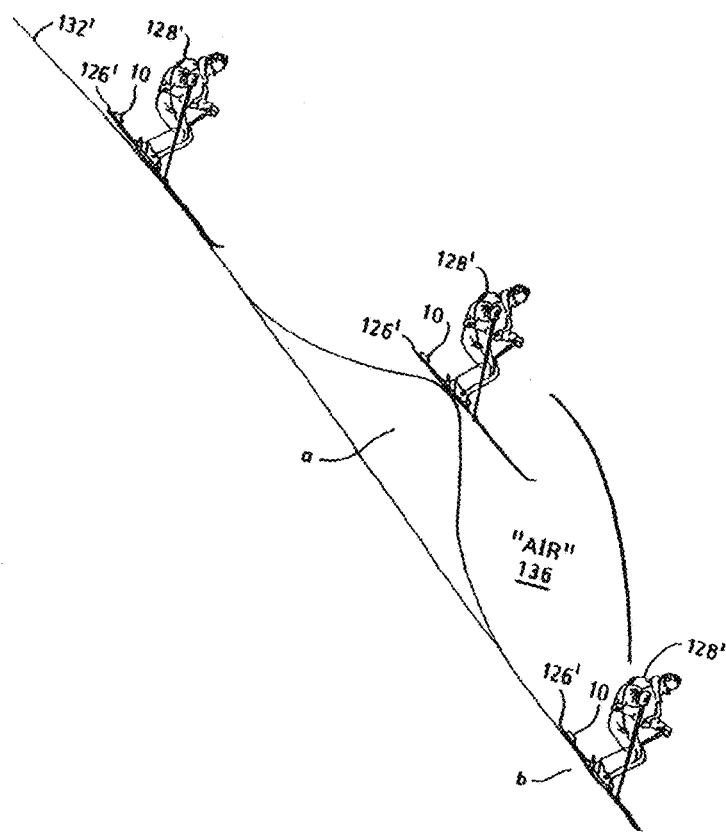

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 16B:
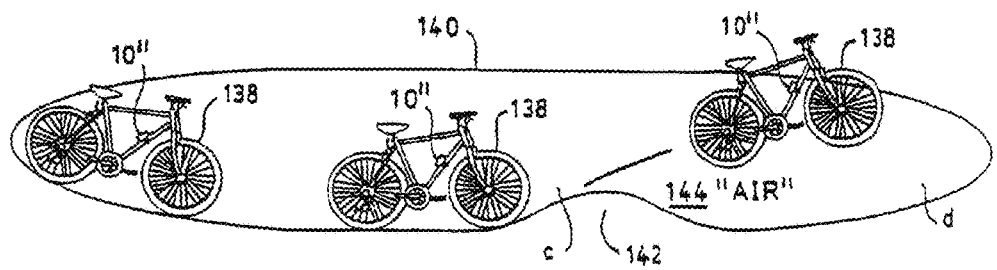
Figure 16C:
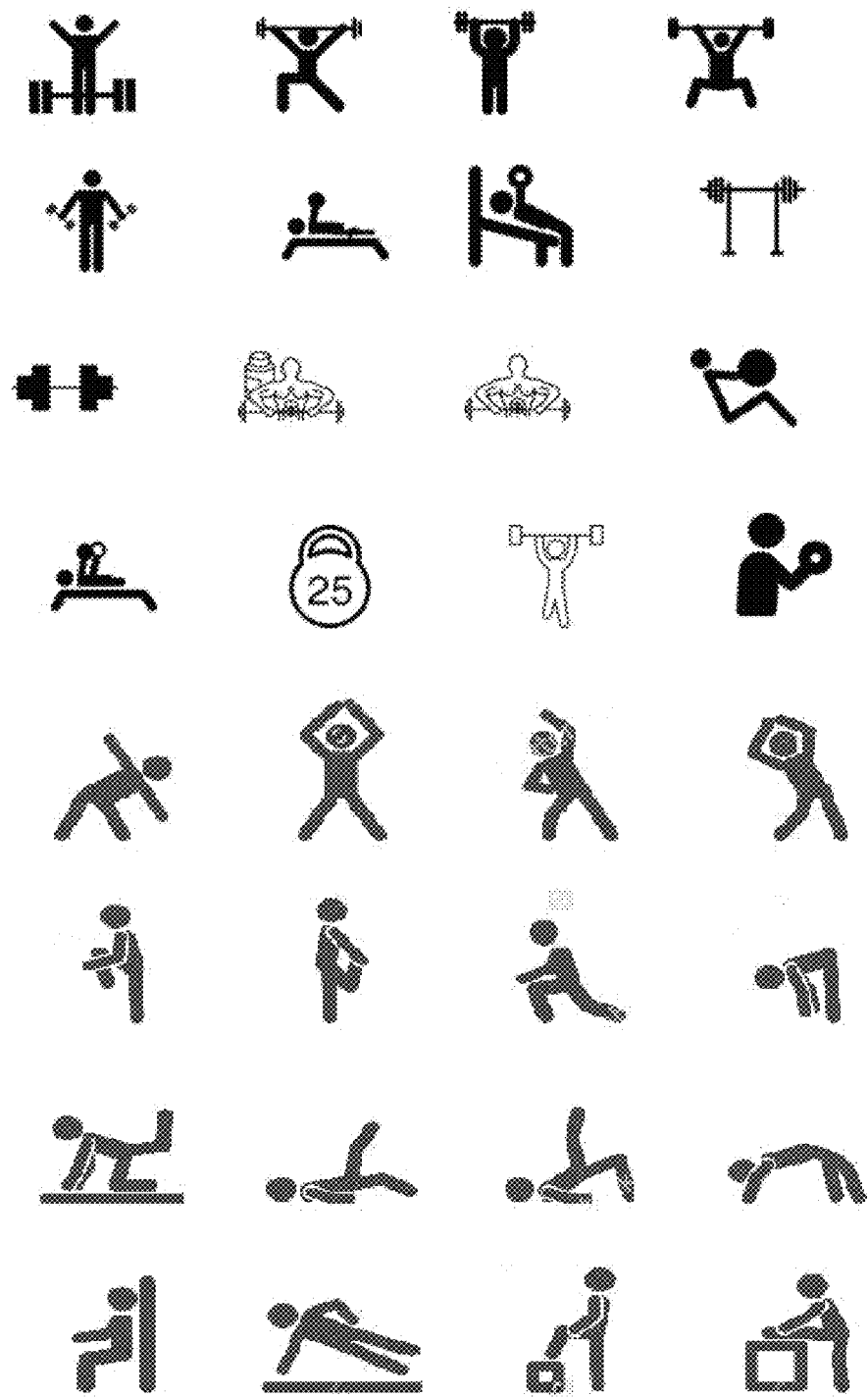

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
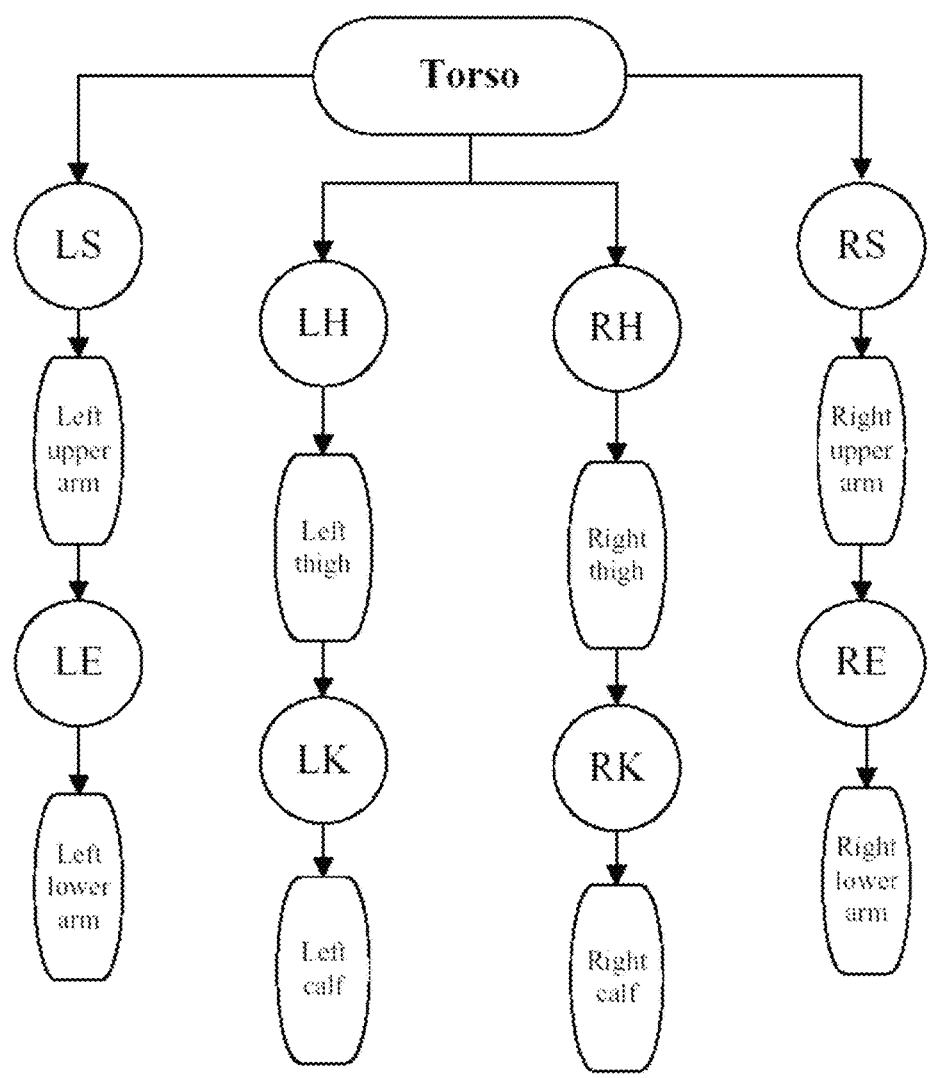
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
  Chest: Barbell Bench Presses, Barbell Incline Presses, Dumbbell Bench Presses, Dumbbell Incline Presses, Dumbbell Flyes, Cable Crossovers
  Back: Pull-Ups, Wide-Grip Lat Pulldowns, One-Arm Dumbbell Rows, Seated Cable Rows, Back Extensions, Straight Arm Pulldowns Shoulders: Seated Dumbbell Presses, Front Raises, Lateral Raises, Reverse Flyes, Upright Cable Rows, Upright Barbell Rows Biceps: Alternate Dumbbell Curls, Barbell Curls, Preacher Curls, Concentration Curls, Cable Curls, Hammer Curls Triceps: Seated Triceps Presses, Lying Triceps Presses, Triceps Kickbacks, Triceps Pushdowns, Cable Extensions, Bench Dips Lower Body Quadriceps: Barbell Squats, Leg Presses, Leg Extensions Hamstrings: Dumbbell Lunges, Straight-Leg Deadlifts, Lying Leg Curls Calves: Seated Calf Raises, Standing Heel Raises Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or sport enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the sport enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the sport enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the sport enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first x min and considered to be the start of the first brushstroke. The first maximum x value following the first minimum x value is located and construed to be the middle of the first exercise stroke (where exercise motion changes from one direction to the other). The next x min value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (x max and x min) are determined. The Y-direction lengths, Ly1 and Ly2, between the data points just before and just after each of x max and x min (x max+1, x max−1, and X min+1, x min−1) are then determined. The length Lx along the x axis, between x max and x min, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, sport enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Sport enthusiasts with pure motor hemiparesis present with face, arm, and leg weakness. This condition usually affects the extremities equally, but in some cases it affects one extremity more than the other. The most common stroke location in affected sport enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Sport enthusiasts with clumsy-hand dysarthria syndrome experience unilateral hand weakness and dysarthria. The dysarthria is often severe, whereas the hand involvement is more subtle, and sport enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)—suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the sport enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the sport enthusiast to get to a resting place or a notification to a nurse or caregiver to render timely assistance. The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Features of the auto-detection of exercise include the following:

1. An exercise system, comprising:
    a processor running the motion analyzer and coupled to a wireless transceiver;
    an accelerometer coupled to the processor; and
    a kinematic motion analysis module executed by the processor to detect exercise type.
2. The system of claim 1, comprising a plurality of smart modules mounted on an exerciser forming a mesh network.
3. The system of claim 1 where the electronic components, sensors, and interconnects of the system monitor, record, process and/or transmit events of interest (such as accelerometers and gyroscopes for impact events, temperature sensors for temperature and/or temperature gradients, pressure sensors, moisture sensors, chemical sensors).
4. The system of claim 1 comprised for sensing and/or monitoring impact events where the sensors are accelerometers, gyroscopes, and/or pressure sensors.
5. The system of claim 1 comprised for sensing and/or monitoring and/or controlling ongoing events where the sensors monitor temperature, temperature gradients, motion, position, environmental or chemical levels, or other such information.
6. The system of claim 1 comprised for sensing events or other information including mounting multiple distributed sensors for obtaining spatial and/or temporal distribution in the data and/or multiple sensors sensing different information and data.
7. The system of claim 1 comprising a camera and an image recognition module to determine kinematic movement.
8. The system of claim 1 including a statistical recognizer to determine kinematic movement.
9. The system of claim 8, comprising a model-state that contains the extracted features of body signatures and other associated characteristics of body signatures.
10. The system of claim 1 comprising links connecting a root node (torso) with connected joint, left shoulder (LS), right shoulder (RS), left hip (LH), and right hip (RH), and left elbow (LE), right elbow (RE), left knee (LK), and right knee (RK) connect upper and lower extremities.
11. The system of claim 1 comprising a posture detection module.
12. The system of claim 1, comprising a module to detect a lying down state and a standing state.
13. The system of claim 1, comprising a hidden markov model module to detect muscle movement and exercise pattern.
14. The system of claim 1 comprising optimizing tennis shots to improve serve, groundstroke, volley, half volley, smash, forehand, backhand, flat, side spin, block, slice, topspin shot, lob, passing shot, dropshot, crosscourt shot, down-the-line shot.
15. The system of claim 1, comprising an electromyography (EMG) sensor to detect muscle strength or weakness.
16. The system of claim 1, comprising an emotion detector wherein an exercise can be increased, decreased, or stopped based on detected emotion.
17. The system of claim 17, wherein the detector comprises video detection of faces or a GSR sensor.
18. The system of claim 1 comprising a cloud storage to receive sensor data.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor 14 can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement.

Another Internet of Things (TOT) device includes

1. An Internet of Things (TOT) device, comprising:
   a device body;
   an accelerometer coupled to the body to detect acceleration;
   a camera coupled to the body to detect a distance of an object from the body;
   a wireless transceiver; and
   a processor coupled to the transceiver, the accelerometer and the camera.
2. The device of claim 1, comprising a module to detect emotional health based on frequency and content of messaging and social network usage.
3. The device of claim 1, comprising a sensor to capture omic data relating to genomic, proteomic, transcriptomic, nutrigenomic, or metabolomic conditions from a user.
4. The device of claim 3, comprising a module to correlate emotional health with omic changes for one of genomic, proteomic, transcriptomic, nutrigenomic, metabolomic condition; and to generate a treatment for people with similar emotional states.
5. The device of claim 3, comprising a module to detect omic changes with genomic, proteomic, transcriptomic, nutrigenomic and metabolomic analysis, and to track omic changes to physiological changes in the subject over time.
6. The device of claim 1, comprising a decision support module to apply genetic clinical data to a subject, and in case of an adverse event for a drug or treatment, generating a drug safety signal to alert a doctor or a manufacturer, wherein the DSS includes rule-based alerts on pharmacogenetics, oncology drug regimens, wherein the module performs ongoing monitoring of actionable genetic variants.
7. The device of claim 1, comprising a module for:
   mining the clinical database and health database for one or more markers associated with one or more health conditions and for patients sharing similarity with the subject;
   identifying at least one similar health conditions and identifying one or more corrective actions previously taken in the repository and the result of each corrective action for the one or more health conditions;
   presenting the corrective action and result to a doctor and recommending an action to reduce risk from the predicted health condition.
8. The device of claim 1, comprising a module to identify similar patients based on at least one of a gene, affected pathway, tumor type, and treatment for a patient's cancer.
9. The device of claim 1, comprising a module for:
   aggregating genetic information, environmental information, treatment data, and treatment response from a patient population;
   applying a learning machine to predict disease risks based on the aggregated genetic information, treatment data, and treatment response from a patient population; and
   recommending lifestyle modification to mitigate the disease risks.
10. The device of claim 1, comprising a module for:
    providing a network to communicate cancer treatment information relating to the community;
    capturing genetic information including gene alterations and alteration quantities from one or more gene sequencers;
    linking one or more oncology consultant computers to the network;
    linking one or more treating professional computers coupled to the network; and
    storing genetic information for each patient and facilitating secured cancer treatment collaboration by the community through a server.
11. A method, comprising:
    receiving subject fitness data and omic information on a device having:
    an accelerometer coupled to the body to detect acceleration;
    a camera coupled to the body to capture a subject image;
    a wireless transceiver; and a processor coupled to the transceiver, the accelerometer and the camera; and
    based on genetic sequence data, predicting treatment response of the subject to a therapeutic intervention; and
    recommending subject lifestyle modification to mitigate a disease.
12. The method of claim 11, comprising predicting the development of tumors.
13. The method of claim 11, comprising analyzing distant metastases.
14. The method of claim 11, comprising:
    aggregating genetic information, environmental information, treatment data, and treatment response from a patient population;
    applying a learning machine to predict disease risks based on the aggregated genetic information, treatment data, and treatment response from a patient population; and
    recommending lifestyle modification based on the aggregated population data.
15. The device of claim 11, comprising correlating emotional health with omic changes for one of genomic, proteomic, transcriptomic, nutrigenomic, metabolomic condition and generating a treatment for people with similar emotional states.
16. The method of claim 11, comprising detecting omic changes with genomic, proteomic, transcriptomic, nutrigenomic and metabolomic analysis, and tracking omic changes to physiological changes in the subject over time.
17. The method of claim 11, comprising correlating emotional health with omic changes for one of genomic, proteomic, transcriptomic, nutrigenomic, metabolomic condition; and to generate a treatment for people with similar emotional states.
18. The method of claim 11, comprising:
    mining the clinical database and health database for one or more markers associated with one or more health conditions and for patients sharing similarity with the subject;
    identifying at least one similar health conditions and identifying one or more corrective actions previously taken in the repository and the result of each corrective action for the one or more health conditions;
    presenting the corrective action and result to a doctor and recommending an action to reduce risk from the predicted health condition.
19. The method of claim 11, comprising detecting emotional health based on frequency and content of messaging and social network usage.

20. The device of claim 19, comprising a module for:
obtaining clinical data and genetic data from one or more clinical laboratory test equipment;
storing genetic markers including germ line data and somatic data over time in a clinical database;
obtaining clinical data from a physician database or from an emergency room database;
correlating the emotional health with the clinical data and genetic data to detect health changes in a subject.

1. A method of providing healthcare management services to a subject, comprising:
obtaining clinical data from one or more laboratory test equipment;
obtaining clinical data from one or more omic equipment;
obtaining clinical data from a primary care physician database;
obtaining clinical data from a specialist physician database;
obtaining clinical data from an in-patient care database or from an emergency room database;
saving the clinical data into a clinical data repository;
obtaining health data from fitness devices or from mobile phones;
obtaining behavioral data from social network communications and mobile device usage patterns;
saving the health data and behavioral data into a health data repository separate from the clinical data repository;
mining the clinical data repository and health data repository for one or more markers associated with one or more health conditions and for patients sharing similarity with the subject;
identifying at least one similar health conditions and identifying one or more corrective actions previously taken in the repository and the result of each corrective action for the one or more health conditions;
presenting the corrective action and result to the subject and recommending an action to reduce risk from the predicted health condition; and
monitoring the health condition using updates in the clinical data repository and health data repository.

2. The method of claim 1, comprising analyzing markers over a period of time for each phase of coronary disease including soluble CD40 ligand; fibrinogen; free fatty acid; intercellular adhesion molecule; interleukin; ischemia modified albumin; matrix metalloproteinases; myeloperoxidase; myoglobin; N-terminal proBNP; oxidized low-density lipoprotein; plasminogen activator inhibitor; pregnancy-associated plasma protein-A; placental growth factor; tissue factor; tumor necrosis factor; troponin I; troponin T; vascular cell adhesion molecule; von Willebrand factor.

3. The method of claim 1, comprising
detecting emotional health using email, mobile phone usage pattern including frequency of messaging, and social network communications;
correlating the emotional health with omic changes relating to genomic, proteomic, transcriptomic, nutrigenomic, metabolomic conditions, and
generating treatment plan from a treatment template for people with similar emotional states and customizing the treatment plan; and
tracking omic changes to emotional health changes in the subject over time.

4. The method of claim 1, comprising detecting omic changes with genomic, proteomic, transcriptomic, nutrigenomic and metabolomic analysis, and tracking omic changes to physiological changes in the subject over time.

5. The method of claim 4, comprising determining dynamic trends related directly to the physiological states of the subject during healthy and diseased states by correlating patterns over time and unusual events.

6. The method of claim 4, comprising normalizing the omic data for identifying common trends and features, searching for spike events, and clusterizing the data to determine similar subjects.

7. The method of claim 4, normalizing omic data for identifying common trends and features, assessing non-randomness of the time-series, searching for spike events, and clusterizing the data to determine similar patient patterns for diabetes, stroke, myocardial infarction, heart failure, and renal disease.

8. The method of claim 1, comprising:
analyzing from the clinical repository blood pressure, obesity, insulin resistance, potassium intake, and calcium intake;
analyzing from the health repository alcohol intake, salt intake, sedentary lifestyle, and stress; and
presenting analytics and coaching the subject to reduce blood pressure.

9. The method of claim 7, comprising predicting risk for high blood pressure by analyzing gene mutations at an angiotensinogen locus or a renin-angiotensin system.

10. The method of claim 7, comprising analyzing emotion, obesity and alcohol consumption data using a wearable device.

11. The method of claim 1, comprising monitoring drug response or drug resistance based on omic data.

12. The method of claim 11, comprising analyzing from the clinical repository blood pressure, obesity, insulin resistance, potassium intake, and calcium intake, and analyzing from the health repository sugar intake, sedentary lifestyle, and stress and presenting analytics and coaching the subject to reduce blood pressure.

13. The method of claim 1, wherein the marker classifies the subject as insulin resistant, insulin impaired, or insulin sensitive.

14. The method of claim 13, comprising determining changes between two or more test periods with level of 2-hydroxybutyrate, linoleoyl LPC, oleoyl LPC, oleate, linolenate, linoleate, glycerophosphorylcholine (GPC), and stearate.

15. The method of claim 1, comprising applying one or more markers to detect atherosclerosis or cardiomyopathy.

16. The method of claim 15, wherein the marker comprises ADMA, asymmetrical dimethyl arginine; Apo B, apolipoprotein B; CETP, cholesterol ester transfer protein; GPX1, glutathione peroxidase; IL, interleukin; IMT, intimal-medial thickness; Lp(a), lipoprotein a; LpPLA2, lipoprotein-associated phospholipase A2; LV, left ventricle; LVH, LV hypertrophy; MMP, matrix metalloproteinase; MPO, myeloperoxidase; SAA, serum amyloid A; sCD40L, soluble CD40 ligand; sICAM, soluble intercellular adhesion molecule; PAI-1, plasminogen activator inhibitor 1; PET, positron emission tomography; TIMP, tissue inhibitor of matrix metalloproteinases; and TPA, tissue plasminogen activator.

17. The method of claim 1, comprising providing automatic messaging to a client on behalf of a healthcare treatment professional, further comprising:

setting up one or more computer implemented agents with rules to respond to a client condition, wherein each agent communicates with another computer implemented agent, the client or the treatment professional; during run-time, receiving a communication from the client and in response selecting one or more computer implemented agents to respond to the communication;

automatically formatting a response to be rendered on a client mobile device to encourage healthy behavior.

18. The method of claim 1, comprising monitoring nutrigenomics and metabolomics using mass spectroscopy to identify multiple analytes in parallel and detect gene expression in response to an environment.

19. A method of providing healthcare management services to a subject, comprising:

obtaining clinical data from one or more laboratory test equipment;

obtaining clinical data from one or more omic equipment;

obtaining clinical data from a primary care physician database;

obtaining clinical data from a specialist physician database;

obtaining clinical data from an in-patient care database or from an emergency room database;

saving the clinical data into a clinical data repository;

obtaining health data from fitness devices or from mobile phones;

obtaining behavioral data from social network communications and mobile device usage patterns;

saving the health data and behavioral data into a health data repository separate from the clinical data repository;

mining the clinical data repository and health data repository for one or more markers associated with one or more health conditions and for patients sharing similarity with the subject;

identifying at least one similar health conditions and identifying one or more corrective actions previously taken in the repository and the result of each corrective action for the one or more health conditions;

presenting the corrective action and result to the subject and recommending an action to reduce risk from the predicted health condition;

monitoring the health condition using updates in the clinical data repository and health data repository; and when the health condition exceeds a threshold, preemptively scheduling the subject for a medical appointment for early treatment of the health condition; and identifying one or more doctors with cancellations or availability to treat the subject to minimize treatment delay and improve doctor office utilization.

20. A method providing healthcare management services to a subject, comprising:

receiving a subject's medical and family historical data;

performing omic analysis on a sample of the subject;

identifying markers indicative of a subject health; and periodically updating information including medical and family historical data, omic update and marker update, and predicting a progression of the subject's health based on updated information.

21. The method of claim 20, comprising:

detecting dietary health using email, mobile phone camera, and social network communications;

correlating the dietary health with omic changes relating to genomic, proteomic, transcriptomic, nutrigenomic, metabolomic conditions, and tracking omic changes to dietary health changes in the subject over time and suggesting dietary changes to improve health based on diet intake and omic changes.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Although embodiments of the present inventions have been described in detail, it should be understood that the various changes, substitutions, and alterations could be made hereto without departing from the spirit and scope of the invention.

What is claimed is:

1. A device, comprising:
a device body;
an accelerometer coupled to the body to detect acceleration;
a sensor coupled to the body;
a wireless transceiver; and
a processor coupled to the transceiver, the accelerometer, the sensor and a blockchain, wherein data linked to a secured transaction is stored in the block chain and where the processor inserts additional data in the block chain for a transaction with a smart contract.

2. The device of claim 1, comprising a module to compare a third party behavior with a user behavior.

3. The device of claim 1, wherein the blockchain stores data on a ledger for a tangible thing or an intangible thing in an exchange.

* * * * *